US012753200B2

(12) United States Patent
Liu et al.

(10) Patent No.: US 12,753,200 B2
(45) Date of Patent: Oct. 6, 2026

(54) GLUCOSE TRIPTOLIDE CONJUGATES AND USES THEREOF

(71) Applicants: The Johns Hopkins University, Baltimore, MD (US); Shanghai Institute of Organic Chemistry, Chinese Academy of Sciences, Shanghai (CN)

(72) Inventors: Jun O. Liu, Baltimore, MD (US); Emmanuel Datan, Baltimore, MD (US); Martin Gilbert Pomper, Baltimore, MD (US); Il Minn, Baltimore, MD (US); Peng Xu, Shanghai (CN); Biao Yu, Shanghai (CN)

(73) Assignees: The Johns Hopkins University, Baltimore, MD (US); Shanghai Institute of Organic Chemistry, Chinese Academy of Sciences, Shanghai (CN)

( * ) Notice: Subject to any disclaimer, the term of this patent is extended or adjusted under 35 U.S.C. 154(b) by 903 days.

(21) Appl. No.: 17/801,509

(22) PCT Filed: Mar. 2, 2021

(86) PCT No.: PCT/US2021/020520

§ 371 (c)(1),
(2) Date: Aug. 22, 2022

(87) PCT Pub. No.: WO2021/178437

PCT Pub. Date: Sep. 10, 2021

(65) Prior Publication Data

US 2023/0134986 A1 May 4, 2023

Related U.S. Application Data

(60) Provisional application No. 62/984,181, filed on Mar. 2, 2020.

(51) Int. Cl.

| | |
|---|---|
| ***C07H 15/26*** | (2006.01) |
| ***A61K 45/06*** | (2006.01) |
| ***A61K 47/54*** | (2017.01) |
| ***A61P 35/00*** | (2006.01) |
| ***C07H 1/00*** | (2006.01) |

(52) U.S. Cl.
CPC ............. *C07H 15/26* (2013.01); *A61K 45/06* (2013.01); *A61K 47/549* (2017.08); *A61P 35/00* (2018.01); *C07H 1/00* (2013.01)

(58) Field of Classification Search
CPC ........ C07H 15/26; A61K 47/549; A61P 35/00
See application file for complete search history.

(56) References Cited

U.S. PATENT DOCUMENTS

| | | | |
|---|---|---|---|
| 6,218,367 | B1 | 4/2001 | Jacob |
| 6,569,893 | B2 | 5/2003 | Dai et al. |
| 6,620,843 | B2 | 9/2003 | Fidler et al. |
| 7,695,738 | B2 | 4/2010 | Lin et al. |
| 9,150,600 | B2 | 10/2015 | Georg et al. |
| 10,040,790 | B2 | 8/2018 | Sun et al. |
| 10,695,319 | B2 | 6/2020 | Liu et al. |
| 2005/0130240 | A1 | 6/2005 | Lin et al. |
| 2017/0166564 | A1 | 6/2017 | Sun et al. |
| 2019/0038596 | A1 | 2/2019 | Liu et al. |

FOREIGN PATENT DOCUMENTS

| | | | | | |
|---|---|---|---|---|---|
| CN | 110498829 | A | * | 11/2019 | ............. A61P 35/02 |
| WO | WO 2010/078427 | A1 | | 7/2010 | |
| WO | WO-2017136739 | A1 | * | 8/2017 | ........... A61K 31/365 |

OTHER PUBLICATIONS

Boothroyd, S.; et al. “Why Do Some Molecules Form Hydrates or Solvates?” Cryst. Growth Des. 2018, vol. 18, pp. 1903-1908. (Year: 2018).*
English language machine translation of CN110498829A; translated Jul. 26, 2025. (Year: 2019).*
Hamada et al., “Chemo-enzymatic Synthesis of Propionyl-ester-linked Taxol-monosaccharide Conjugate and its Drug Delivery System Using Hybrid-Bio-nanocapsules Targeting Brain Glioma Cells”, Clinical Medicine Insights: Women’s Health, 2013, vol. 6, pp. 71-75.
International Search Report and Written Opinion received for PCT Patent Application No. PCT/US2017/016527, on Jun. 6, 2017, 9 pages.
Liu et al., “Highly water-soluble platinum(II) complexes as GLUT substrates for targeted therapy: improved anticancer efficacy and transporter-mediated cytotoxic properties”, Chemical Communications, Mar. 25, 2013, vol. 49, No. 24, pp. 2421-2423.
Liu et al., “Synthesis of 2'-paclitaxel methyl 2-glucopyranosyl succinate for specific targeted delivery to cancer cells”, & Medicinal Chemistry Letters, Jan. 19, 2007, vol. 17, No. 3, pp. 617-620.

(Continued)

*Primary Examiner* — Andrea Olson
*Assistant Examiner* — Benjamin M Brandsen
(74) *Attorney, Agent, or Firm* — DLA Piper LLP (US)

(57) ABSTRACT

A major hurdle in the treatment of cancer is chemoresistance induced under hypoxia that is characteristic of tumor microenvironment. Triptolide, a potent inhibitor of eukaryotic transcription, possesses potent antitumor activity. However, its clinical potential has been limited by toxicity and water solubility. To address those limitations of triptolide, the present disclosure designed and synthesized glucose-triptolide conjugates (glutriptolides) and demonstrated their antitumor activity in vitro and in vivo. The glutriptolides disclosed herein possess improved stability in human serum, greater selectivity towards cancer over normal cells and increased potency against cancer cells. Importantly, the glutriptolides are more potent against cancer cells under hypoxic conditions in contrast to existing cytotoxic drugs. These glutriptolides also exhibit sustained antitumor activity, prolonging survival in a prostate cancer metastasis animal model. Together, these findings suggest a new strategy to overcome chemoresistance through conjugation of cytotoxic agents to glucose.

21 Claims, 26 Drawing Sheets

(56) References Cited

OTHER PUBLICATIONS

Partial European Search Report received for EP Patent Application No. 17748283.3, mailed on Aug. 19, 2019, 12.
PCT International Search Report and Written Opinion in International Application No. PCT/US2021/020520, dated May 6, 2021, 10 pages.
Pubchem Open Chemistry Database, Compound Summary for CID 101239577, "(14-S)-14-O-beta-D-Glucopyranosyltriptolide" (Create Date: Dec. 18, 2015, Modify Date Mar. 18, 2017), 10 pages, National Institutes of Health, U.S. National Library of Medicine.
Supplementary European Search Report and Search Opinion received for EP Patent Application No. 17748283.3, on Nov. 20, 2019, 10 pages.
Yang et al. Molecular Cancer Therapeutics (2003), vol. 2, pp. 65-72.
Zhou et al., "Conjugating glucosamine to triptolide to enhance its protective effect against renal ischemia-reperfusion injury and reduce its toxicity", Journal of Drug Targeting, vol. 22, No. 3, Oct. 7, 2014, pp. 200-210.
Datan et al., "A Glucose-Triptolide Conjugate Selectively Targets Cancer Cells under Hypoxia," *iScience* (2020), 23(9):1-13.
Liu et al., "The Effect of Triptolide-Loaded Exosomes on the Proliferation and Apoptosis of Human Ovarian Cancer SKOV3 Cells," *BioMed Res. Int.* (2019), 2019:1-14.
Bhatnagar et al. AEG-1 promoter-mediated imaging of prostate cancer. Cancer Res., (2014), pp. 5772-5781, vol. 74.
Datan et al. A glucose-triptolide conjugate selectively targets cancer cells under hypoxia. iScience., (2020), pp. 1-13, vol. 23.
Li et al. Involvement of endoplasmic reticulum stress in all-trans-retinal-induced retinal pigment epithelium degeneration. Toxicological Sciences., (2015), pp. 196-208, vol. 143.
Liu et al. The effect of triptolide-loaded exosomes on the proliferation and apoptosis of human ovarian cancer SKOV3 cells. BioMed Research International., (2019), pp. 1-14.
Sullivan et al. Essentials of biostatistics for public health. Johnes & Bartlett., (2017), ed. 3.
Titov et al. XPB, a subunit of TFIIH, is a target of the natural product triptolide. Nat Chem Biol., (2011), pp. 182-188, vol. 7.

* cited by examiner compound 10 compound 10L
(high general toxicity)

TPL compound 1 compound 1L
(lower general toxicity)

TPL

GLUCOSE TRIPTOLIDE CONJUGATES AND USES THEREOF

CROSS-REFERENCE TO RELATED APPLICATIONS

This application is a 35 USC § 371 National Stage application of International Application No. PCT/US2021/020520 filed Mar. 2, 2021, which claims the benefit under 35 USC § 119 (e) to U.S. Application Ser. No. 62/984,181 filed Mar. 2, 2020, now expired. The disclosure of each of the prior applications is considered part of and is incorporated by reference in the disclosure of this application.

GOVERNMENT SUPPORT

This invention was made with government support under GM008763, TR001079 and CA006973 awarded by the National Institutes of Health. The government has certain rights in the invention.

BACKGROUND OF THE INVENTION

Field of the Disclosure

The present invention relates generally to small molecules and more specifically to use of small molecules for cancer therapeutics.

Background Information

Despite its fundamental role in cell proliferation and survival, there exist far fewer inhibitors of eukaryotic transcription in comparison to those of translation. Triptolide ((1S,2S,4S,5S,7R,8R,9S,11S,13 S)-8-hydroxy-1-methyl-7-propan-2-yl-3,6,10,16 tetraoxaheptacyclo[11.7.0.02,4.02,9.05,7.09,11.014,18]icos-14(18)-en-17-one), an active ingredient from the traditional Chinese medicinal plant Thunder God Vine (also known as Lei Gong Teng), has emerged as one of the few specific inhibitors of eukaryotic transcription mediated by RNA polymerase II (RNAPII). Known for its potent immunosuppressive and antiinflammatory activity, extracts of Thunder God Vine with enriched triptolide have been used as a powerful immunosuppressant for treating a wide variety of autoimmune disorders for centuries. Triptolide also exhibits potent antiproliferative activity in almost all cancer cell lines tested to date. The molecular mechanism underlying the antiproliferative activity of triptolide has been investigated for decades. Although a number of putative triptolide-binding proteins have been reported, most cannot account for its antiproliferative and pro-apoptotic activity. The identification and validation of the XPB subunit of the general transcription factor TFIIH as the physiological target of triptolide offered a plausible molecular explanation for the broad anticancer activity of triptolide.

Triptolide forms a covalent adduct with Cys342 in the active site of XPB, leading to the inhibition of the DNA-dependent ATPase activity of XPB, effectively blocking transcriptional initiation by RNAPII. We have shown that mutation of Cys342 to a threonine residue in a single remaining allele of the XPB gene produces a viable, albeit slow-growing, HEK293T cells that became nearly completely resistant to triptolide. In addition to the Cys342 residue, a number of other residues in both XPB and its regulatory subunit p52 seem to play important roles in the interaction between TFIIH and triptolide, as their mutations also caused resistance, albeit to different degrees, to triptolide among the mutant-expressing cell lines. The effect of triptolide on transcription did not seem to be caused solely by the inhibition of the ATPase activity of TFIIH, as the binding of triptolide to XPB subsequently causes degradation of the catalytic subunit of RNAPII, exacerbating the inhibitory effect of triptolide on RNAPII-mediated transcription. Recent work has implicated the CDK7 kinase as part of the pathway leading to the ubiquitylation and proteasome-mediated degradation of RNAPII induced by triptolide. The precise mechanism by which triptolide triggers the degradation of the RPB1 subunit of RNAPII, however, still remains to be completely elucidated. Thus, triptolide inhibits eukaryotic transcription by a unique two-step mechanism, inhibition of XPB to prevent RNAPII-mediated transcription initiation followed by degradation of RNAPII itself.

SUMMARY

Disclosed herein is a glucose-triptolide conjugate with the structure of Formula (I), or a pharmaceutically acceptable salt or solvate, a stereoisomer, a diastereoisomer or an enantiomer thereof.

Formula (I)

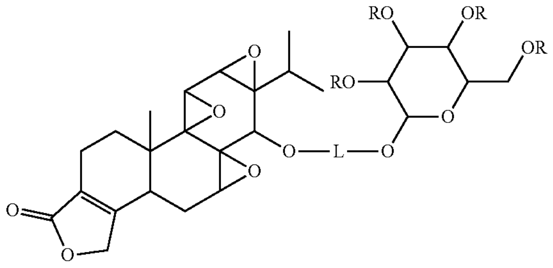

In some embodiments, L can be selected from $-CO(CR_1R_2)_nCO-$, $-(CR_1R_2)_nCO-$, $-CO(CR_1R_2)_n-$, $-(CR_1R_2)_nSO-$, $-(CR_1R_2)_nSO_2-$, $-SO(CR_1R_2)_n-$, $-SO_2(CR_1R_2)_n-$, $-SO(CR_1R_2)_nSO-$, $-SO_2(CR_1R_2)_nSO_2-$,

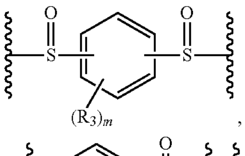
,
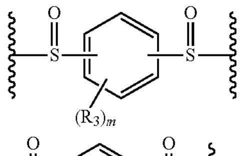
,
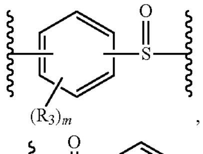
,
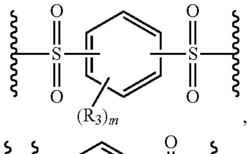
,
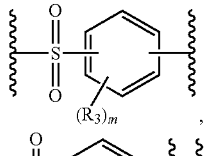
,
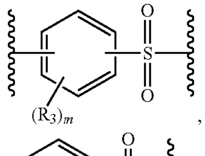
,
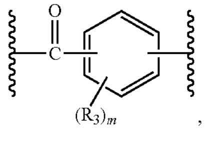
,
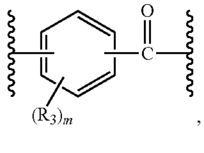
, and -continued

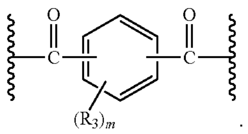

Each n can be an integer selected from 0 to 6. m can be an integer selected from 0 to 4. Each $R_1$ and $R_2$ can be independently selected from hydrogen, methyl, ethyl, and halogen. $R_3$ can be selected from hydrogen, methyl, ethyl, propyl, amino, nitro, cyano, trifluoromethyl, alkoxy, azido, and halogen.

Also disclosed herein is a glucose-triptolide conjugate with the structure of Formula (II), or a pharmaceutically acceptable salt or solvate, a stereoisomer, a diastereoisomer or an enantiomer thereof.

Formula (II)

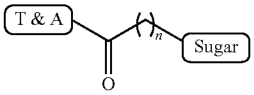

In some embodiments, n can be an integer selected from 0 to 10. In some embodiments, n can be 3. T & A moiety can be triptolide or one of its analogs. In some embodiments, T & A moiety can be selected from

TA1

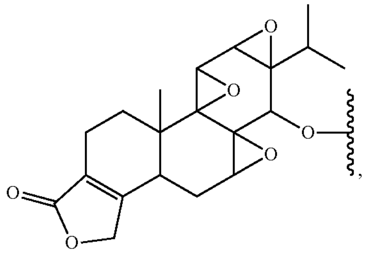

TA2

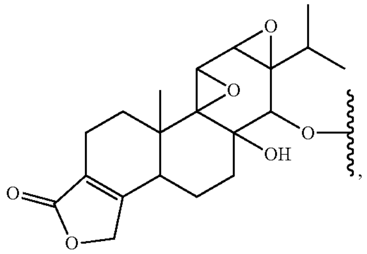

TA3

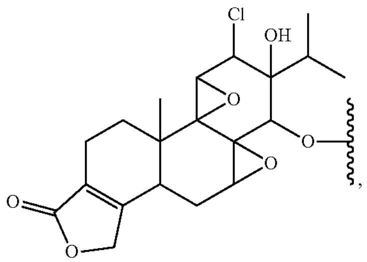

-continued

TA4

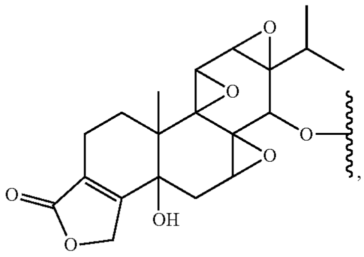

TA5

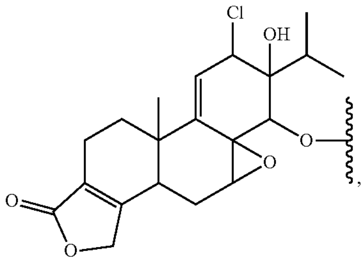

TA6

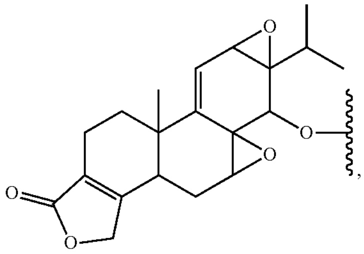

TA7

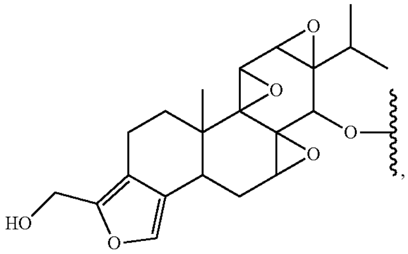

TA8

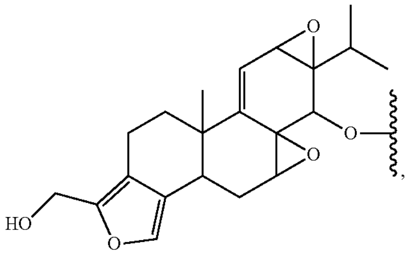

TA9

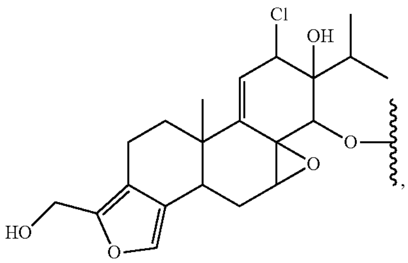

-continued
TA10
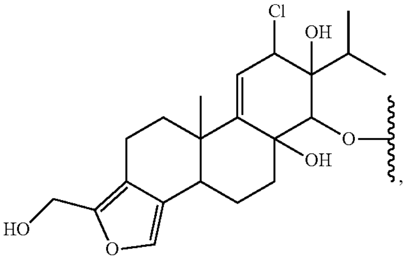
TA11
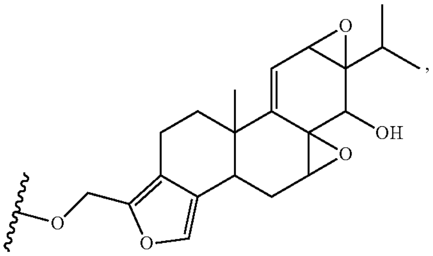
TA12
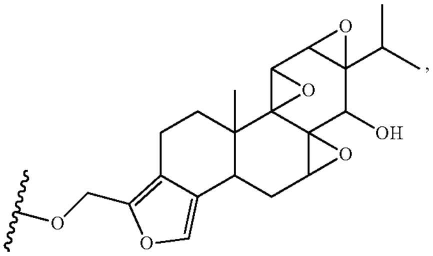
TA13
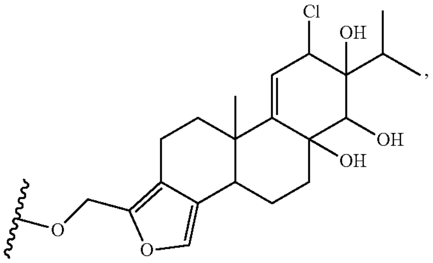
TA14
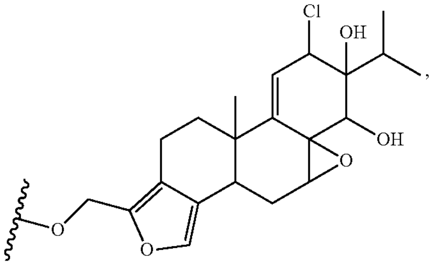
TA15
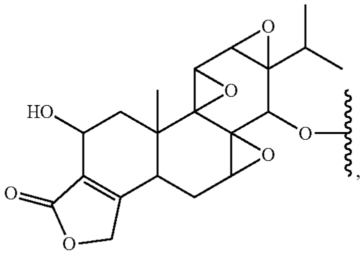
-continued
TA16
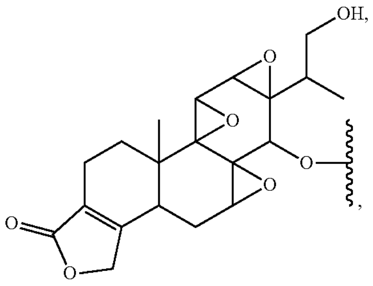
TA17
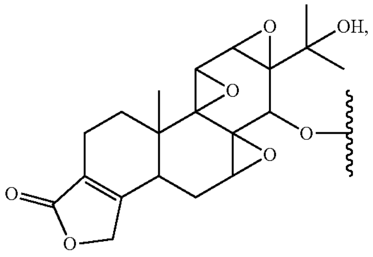
and a pharmaceutically acceptable salt or solvate, a stereoisomer, a diastereoisomer or an enantiomer thereof.
In some embodiments, Sugar moiety can be selected from
sugar 1
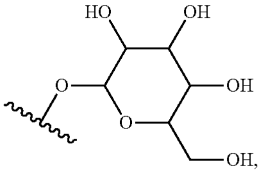
sugar 2
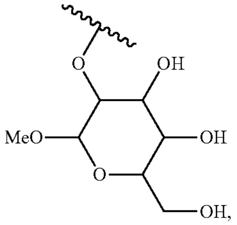
sugar 3
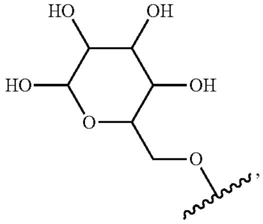
sugar 4
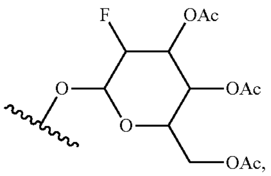

-continued
sugar 5
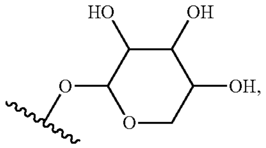
sugar 6
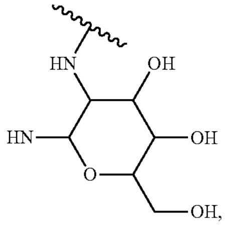
sugar 7
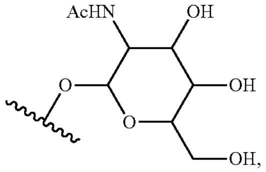
sugar 8
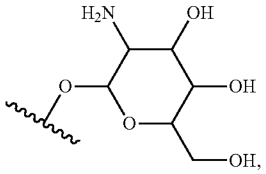
sugar 9
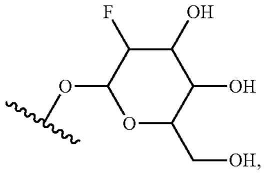
sugar 10
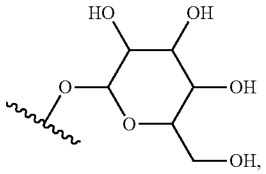
sugar 11
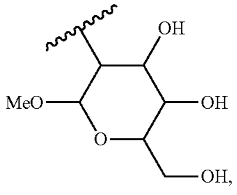
sugar 12
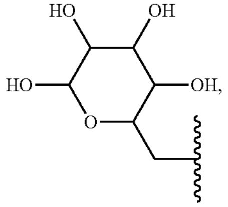
-continued
sugar 13
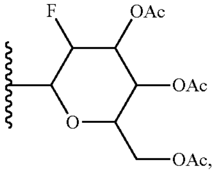
sugar 14
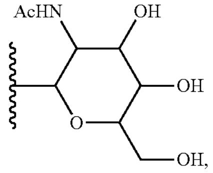
sugar 15
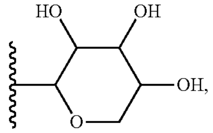
sugar 16
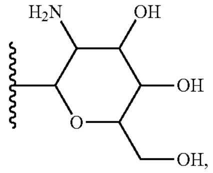
sugar 17
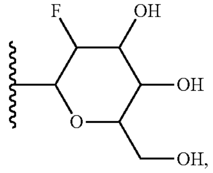
sugar 18
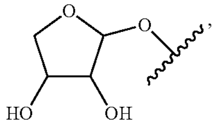
sugar 19
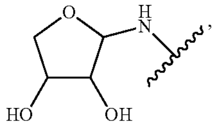
sugar 20
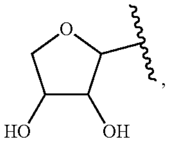
and a pharmaceutically acceptable salt or solvate, a stereoisomer, a diastereoisomer or an enantiomer thereof.

In some embodiments, the glucose-triptolide conjugate in the present disclosure is compound 1 with the following structure:

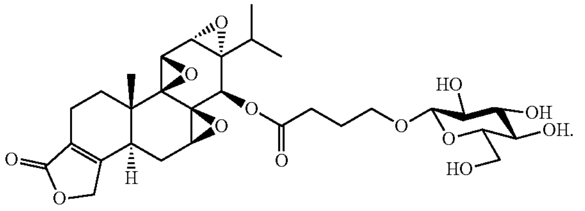

Also disclosed is a pharmaceutical formulation, which can include a compound with the structure of Formula (I), Formula (II), or compound 1, and a pharmaceutically acceptable carrier.

Further disclosed herein is a method of synthesizing a glucose-triptolide conjugate, or a pharmaceutically acceptable salt or solvate, a stereoisomer, a diastereoisomer or an enantiomer thereof. The method can include

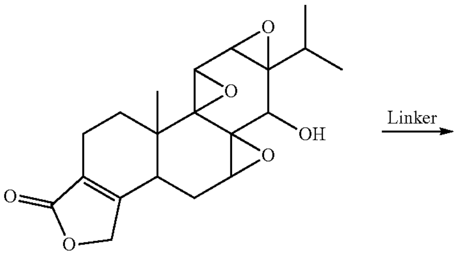

Triptolide

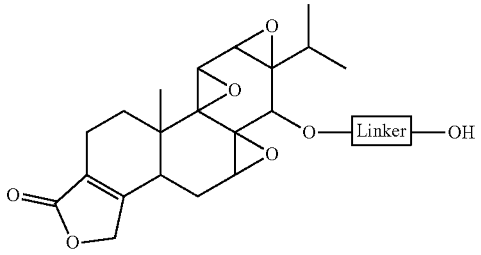

T1

(a) conjugating triptolide with a Linker selected from 4-hydroxybutanoic acid, phthalic acid, 1,5-pentanedioic acid, and succinic acid to form a triptolide Linker derivative T1;

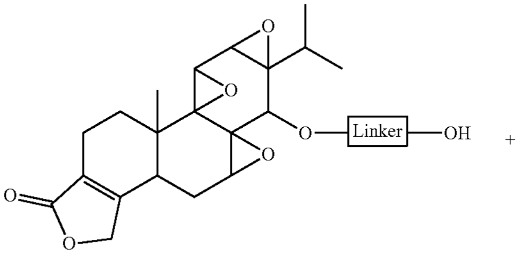

T1

-continued

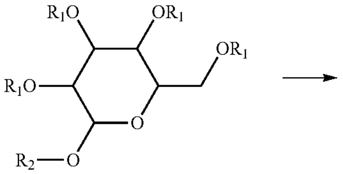

T2

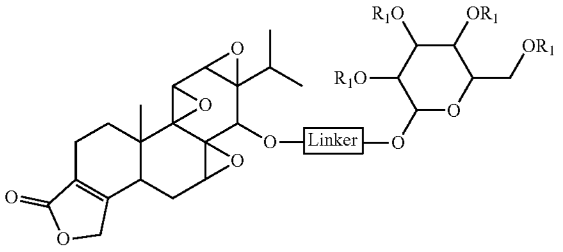

T3

(b) reacting T1 with a sugar intermediate T2 to get intermediate T3, wherein $R_1$ is selected from the group consisting of para-methoxylbenzyl, 1-chloroacetyl protective group, triethylsilyl, and benzyl; and $R_2$ is hydrogen or $CNHCCl_3$; and

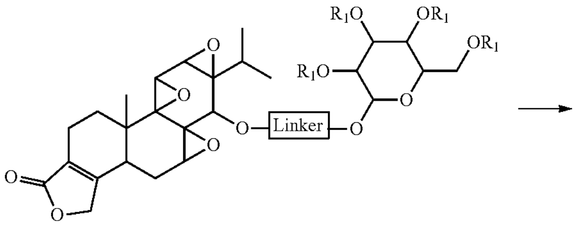

T3

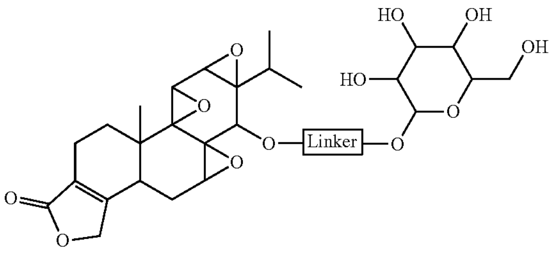

T4

(c) deprotecting the intermediate T3 to obtain the glucose-triptolide conjugate T4.

T3 can also be synthesized by following the steps provided below:

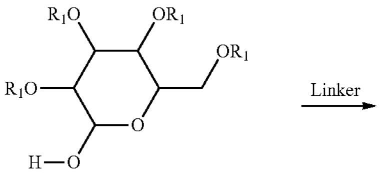

T5

-continued

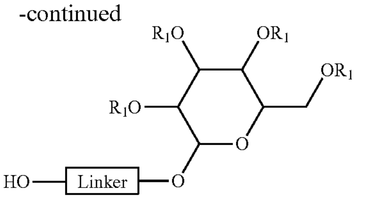

T6 conjugating a glucose T5 with a Linker selected from 4-hydroxybutanoic acid, phthalic acid, 1,5-pentanedioic acid, and succinic acid to form a glucose Linker derivative T6, wherein X is O, $R_1$ is selected from para-methoxylbenzyl, 1-chloroacetyl protective group, triethylsilyl, and benzyl; and

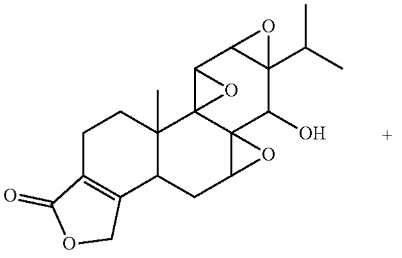

Triptolide

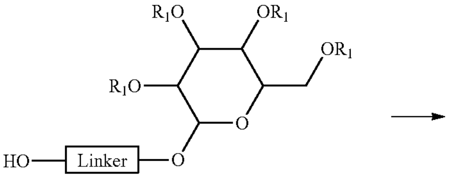

T6

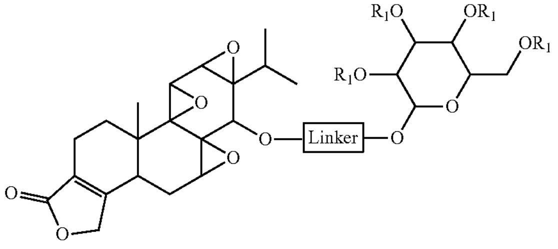

T3 reacting the glucose Linker derivative T6 with triptolide to get an intermediate T3.

In some embodiments, $R_1$ is para-methoxylbenzyl (PMB). In some embodiments, $R_2$ is $CNHCCl_3$. In some embodiments, the deprotecting reaction is achieved by trifluoroacetic acid (TFA).

Further disclosed herein is a method of treating a disease in a subject, include administering an effective amount of the compound with a structure of Formula (I), Formula (II), or compound 1. In some embodiments, the disease can be cancer, the type of cancer can be selected from the group consisting of central nervous system (CNS) cancer, lung cancer, breast cancer, colorectal cancer, prostate cancer, stomach cancer, liver cancer, cervical cancer, esophageal cancer, bladder cancer, Non-Hodgkin lymphoma, leukemia, pancreatic cancer, kidney cancer, endometrial cancer, head and neck cancer, lip cancer, oral cancer, thyroid cancer, brain cancer, ovary cancer, renal cancer, melanoma, gallbladder cancer, laryngeal cancer, multiple myeloma, nasopharyngeal cancer, Hodgkin lymphoma, testis cancer and Kaposi sarcoma. In some embodiments, the method can further include administering a chemotherapeutic agent, the compound can be administered prior to, simultaneously with or following the administration of the chemotherapeutic agent. In some embodiments, the compound can be administered subcutaneously (s.c.), intravenously (i.v.), intramuscularly (i.m.), intranasally, orally, or topically. In some embodiments, the compound can be formulated in a delayed release preparation, a slow release preparation, an extended release preparation, or a controlled release preparation. In some embodiments, the compound can be provided in a dosage form selected from an injectable dosage form, infusible dosage form, inhalable dosage form, edible dosage form, oral dosage form, topical dosage form, and combinations thereof.

BRIEF DESCRIPTION OF THE DRAWINGS

In order to facilitate a full understanding of the present disclosure, reference is now made to the accompanying drawings. These drawings should not be construed as limiting the present disclosure, but are intended to be illustrative only.

DETAILED DESCRIPTION

Figure 1:
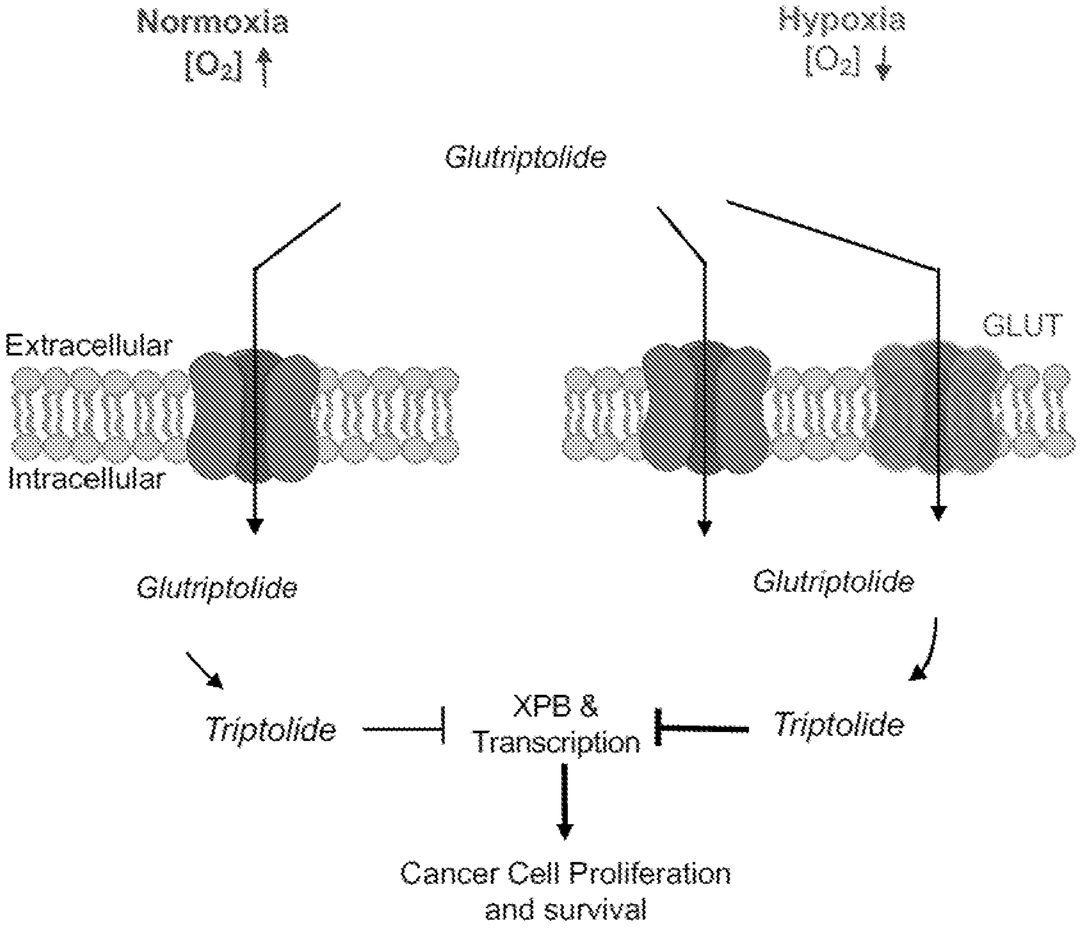
FIG. 1 is a proposed scheme illustrating how increased levels of glucose transporter under hypoxic conditions result in increased uptake of the glucose-triptolide conjugate and increased inhibition of the proliferation of a cancer cell, according to some embodiments of the present disclosure.

A major hurdle in the treatment of cancer is chemoresistance induced under hypoxia that is characteristic of tumor microenvironment. Triptolide, a potent inhibitor of eukaryotic transcription, possesses potent antitumor activity. However, its clinical potential has been limited by toxicity and water solubility. To address those limitations of triptolide, we designed and synthesized glucose-triptolide conjugates (glutriptolides) and demonstrated their antitumor activity in vitro and in vivo. Herein, we identified compound 1 with an altered linker structure. Compound 1 possessed improved stability in human serum, greater selectivity toward cancer over normal cells, and increased potency against cancer cells. Compound 1 exhibits sustained antitumor activity, prolonging survival in a prostate cancer metastasis animal model. Importantly, we found that compound 1 was more potent against cancer cells under hypoxia than normoxia. Together, this work provides an attractive glutriptolide drug lead and suggests a viable strategy to overcome chemoresistance through conjugation of cytotoxic agents to glucose.

Extensive efforts have been made to develop triptolide and its analogs as immunosuppressive and anticancer drugs in the past few decades. One of the major hurdles is the general toxicity of triptolide, most likely attributed to its inhibition of transcription. Another is its limited water solubility. To date, two derivatives of triptolide remain in clinical development. One analog, (5R)-5-hydroxytriptolide, is undergoing clinical trial as an immunosuppressant. The other, Minnelide, a phosphorylated form of triptolide with increased solubility, is undergoing human trials for treating pancreatic and other types of cancer. Given the mechanism-based toxicity of triptolide, it is difficult to separate the antitumor activity and intrinsic toxicity of triptolide with existing triptolide analogs, calling for a radically different approach to addressing the problem. Recently, we designed a different class of triptolide analogs by conjugating it to glucose in hopes to target glucose-addicted tumor cells over normal cells. Moreover, the high water solubility of glucose would significantly increase the solubility of the resultant glucose-triptolide conjugates (refer to hereafter as glutriptolides). One of the lead compounds from our first-generation glutriptolide (compound 10) indeed exhibited higher solubility and tumor cell selectivity over triptolide and was shown to possess sustained antitumor activity in vivo. Unfortunately, an obligate degradation intermediate, triptolide-succinate (also known as F60008), has undergone early human clinical study and was found to be lethal to two patients. In addition, compound 10 suffers from instability in human serum, ruling it out as a viable drug candidate.

To identify glutriptolide analogs with improved pharmacological properties and reduced toxicity, we embarked on the design and synthesis of a series of second-generation glucose-triptolide conjugates by altering the linker structure and accompanying linkage between the linkers and glucose. Screening of these second-generation glutriptolide analogs identified compound 1 with a glycosidic linkage between the linker and glucose that upon degradation, would release an alcohol-containing intermediate. Compound 1 was found to be 4-foldmore potent against cancer cells in vitro and exhibited greater selectivity against cancer cells over normal cells than compound 10. Compound 1 was also found to have much greater stability in human serum. Unlike triptolide, compound 1 had little effect on the ATPase activity of TFIIH in vitro. Similar to triptolide, however, compound 1 inhibited the proliferation of multiple cancer cell lines, induced apoptosis, and caused degradation of the catalytic subunit of RNAPII in an XPB-dependent manner. Using compound 1 as a probe, we also investigated its effects on cancer cells under hypoxic conditions and found that compound 1 is more effective against cancer cells under hypoxic than normoxic conditions. In light of the key role of hypoxia in chemoresistance against almost all known anticancer drugs, our finding with compound 1 raised the exciting possibility of overcoming hypoxia-induced drug resistance through conjugation of drugs to glucose.

When ranges of values are disclosed, and the notation "from n1 . . . to n2" or "between n1 . . . and n2" is used, where n1 and n2 are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.). When n is set at 0 in the context of "0 carbon atoms", it is intended to indicate a bond or null.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety where the atom attached to the carbonyl is carbon. An "acetyl" group refers to a $—C(O)CH_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon group having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH═CH—), (—C::C—)]. Examples of suitable alkenyl groups include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether group, wherein the term alkyl is as defined below. Examples of suitable alkyl ether groups include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl group containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl groups include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene ($—CH_2—$). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) group wherein the term alkyl is as defined above and wherein the sulfur may be singly or doubly oxidized. Examples of suitable alkyl thioether groups include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched-chain hydrocarbon group having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl groups include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C amido" as used herein, alone or in combination, refers to a $C(=O)NR_2$ group with R as defined herein. The term "N amido" as used herein, alone or in combination, refers to a RC(=O)NH group, with R as defined herein. The term "acylamino" as used herein, alone or in combination, embraces an acyl group attached to the parent moiety through an amino group. An example of an "acylamino" group is acetylamino ($CH_3C(O)NH—$).

The term "amino," as used herein, alone or in combination, refers to NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl group derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent group C6H4=derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O carbamyl" as used herein, alone or in combination, refers to a OC(O)NRR' group with R and R' as defined herein.

The term "N carbamyl" as used herein, alone or in combination, refers to a ROC(O)NR' group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O carboxy" group refers to a RC(O)O— group, where R is as defined herein. A "C carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl group having the meaning as defined above wherein one or more hydrogens are replaced with a halogen. Specifically embraced are monohaloalkyl, dihaloalkyl and polyhaloalkyl groups. A monohaloalkyl group, for one example, may have an iodo, bromo, chloro or fluoro atom within the group. Dihalo and polyhaloalkyl groups may have two or more of the same halo atoms or a combination of different halo groups. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene. (—CFH—), difluoromethylene ($—CF_2—$), chloromethylene (—CHCl—) and the like.

The term "heteroalkyl," as used herein, alone or in combination, refers to a stable straight or branched chain, or cyclic hydrocarbon group, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, $—CH_2—NH—OCH_3$.

The term "heteroaryl," as used herein, alone or in combination, refers to a 3 to 7 membered unsaturated heteromonocyclic ring, or a fused monocyclic, bicyclic, or tricyclic ring system in which at least one of the fused rings is aromatic, which contains at least one atom selected from the group consisting of O, S, and N. In certain embodiments, said heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently selected from the group consisting of nitrogen, oxygen, and sulfur In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, which may be optionally substituted as provided.

The term "lower heteroaryl," as used herein, alone or in combination, means either: 1) monocyclic heteroaryl comprising five or six ring members, of which between one and four said members may be heteroatoms selected from the group consisting of O, S, and N; or 2) bicyclic heteroaryl, wherein each of the fused rings comprises five or six ring members, comprising between them one to four heteroatoms selected from the group consisting of O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms selected from the group consisting of O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to NRR', wherein R and R' are independently selected from the group consisting of hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —$NO_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer to the —$SO_3H$ group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —$S(O)_2$—.

The term "N sulfonamido" refers to a $RS(=O)_2NR'$ group with R and R' as defined herein.

The term "S sulfonamido" refers to a $S(=O)_2NRR'$, group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N thiocarbamyl" refers to an ROC(S)NR'— group, with R and R' as defined herein.

The term "O thiocarbamyl" refers to a —OC(S)NRR', group with R and R' as defined herein.

The term "thiocyanato" refers to a —CNS group.

The term "trihalomethanesulfonamido" refers to a $X_3CS(O)_2NR$— group with X is a halogen and R as defined herein.

The term "trihalomethanesulfonyl" refers to a $X_3CS(O)_2$— group where X is a halogen.

The term "trihalomethoxy" refers to a $X_3CO$— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and $R_a$ where n=(1, 2, 3, . . . n), every substituent, and every term should be understood to be independent of every other in terms of selection from a group. Should any variable, substituent, or term (e.g., aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the disclosure encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present disclosure includes all cis, trans, syn, anti, entgegen (E), and zusammen (Z) isomers as well as the appropriate mixtures thereof. Additionally, compounds may exist as tautomers; all tautomeric isomers are provided by this disclosure. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "optically pure stereoisomer" refers to stereoisomeric, such as enantiomeric or diastereomeric excess or the absolute difference between the mole fraction of each enantiomer or diastereomer.

Pharmaceutically acceptable salts of compounds described herein include conventional nontoxic salts or quaternary ammonium salts of a compound, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. In other cases, described compounds may contain one or more acidic functional groups and, thus, are capable of forming pharmaceutically acceptable salts with pharmaceutically acceptable bases. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Disclosed herein is a glucose-triptolide conjugate with the structure of Formula (I), or a pharmaceutically acceptable salt or solvate, a stereoisomer, a diastereoisomer or an enantiomer thereof.

Formula (I)

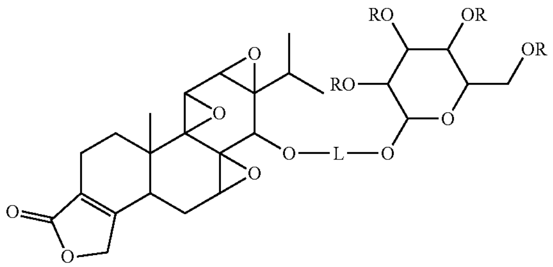

In some embodiments, L can be selected from —X—Y—Z—, wherein X and Z can individually and independently be a direct bond, —$CH_2$—, —C(O)—, —SO—, —$SO_2$—, —OPO—, —$OPO_2$—, and wherein Y is a direct bond, a substituted or unsubstituted —($C_1$-$C_6$)alkyl-, substituted or unsubstituted —$(CH_2)_n$O($C_1$-$C_6$)alkyl-, substituted or unsubstituted —$(CH_2)_n$C(O)($C_1$-$C_6$)alkyl-, substituted or unsubstituted —$(CH_2)_n$C(O)O($C_1$-$C_6$)alkyl-, substituted or unsubstituted —$(CH_2)_n$NH($C_1$-$C_6$)alkyl-, substituted or unsubstituted —$(CH_2)_n$C(O)NH($C_1$-$C_6$)alkyl-, substituted or unsubstituted —$(CH_2)_n$S(C1-C6)alkyl-, substituted or unsubstituted —$(CH_2)_n$C(O)$(CH_2)_n$S($C_1$-$C_6$)alkyl-, substituted or unsubstituted —($C_2$-$C_6$)alkenyl-, substituted or unsubstituted —$(CH_2)_n$O($C_2$-$C_6$)alkenyl-, substituted or unsubstituted —$(CH_2)_n$C(O)($C_2$-$C_6$)alkenyl-, substituted or unsubstituted —$(CH_2)_n$C(O)O($C_2$-$C_6$)alkenyl-, substituted or unsubstituted —$(CH_2)_n$NH($C_2$-$C_6$)alkenyl-, substituted or unsubstituted —$(CH_2)_n$C(O)NH($C_2$-$C_6$)alkenyl-, substituted or unsubstituted —$(CH_2)_n$S($C_2$-$C_6$)alkenyl-, substituted or unsubstituted —$(CH_2)_n$C(O)$(CH_2)_n$S($C_2$-$C_6$)alkenyl-, substituted or unsubstituted —($C_2$-$C_6$)alkynyl-, substituted or unsubstituted —$(CH_2)_n$O($C_2$-$C_6$)alkynyl-, substituted or unsubstituted —$(CH_2)_n$C(O)($C_2$-$C_6$)alkynyl-, substituted or unsubstituted —$(CH_2)_n$C(O)O($C_2$-$C_6$)alkynyl-, substituted or unsubstituted —$(CH_2)_n$NH($C_2$-$C_6$)alkynyl-, substituted or unsubstituted —$(CH_2)_n$C(O)NH($C_2$-$C_6$)alkynyl-, substituted or unsubstituted —$(CH_2)_n$S($C_2$-$C_6$)alkynyl-, substituted or unsubstituted —$(CH_2)_n$C(O)$(CH_2)_n$S($C_2$-$C_6$)alkynyl-, wherein each alkyl, alkenyl and alkynyl group may be optionally substituted with alkyl, alkoxy, amino, hydroxyl, oxo, aryl, heteroaryl, carboxyl, cyano, nitro, azido, or trifluoromethyl. n can be an integer selected from 0 to 6. Each R can be independently selected from the group consisting of hydrogen, alkyl, and acetyl group.

In some embodiments, L can be selected from —CO$(CR_1R_2)_n$CO—, —$(CR_1R_2)_n$CO—, —CO$(CR_1R_2)_n$—, $-(CR_1R_2)_nSO-$, $-(CR_1R_2)_nSO_2-$, $-SO(CR_1R_2)_n-$, $-SO_2(CR_1R_2)_n-$, $-SO(CR_1R_2)_nSO-$, $-SO_2(CR_1R_2)_nSO_2-$,

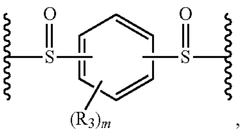 , 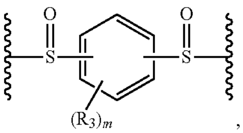 ,

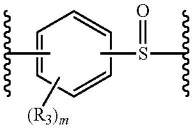 , 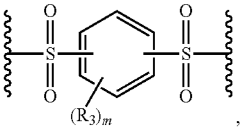 ,

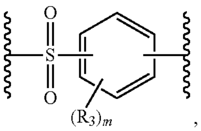 , 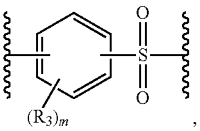 ,

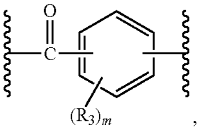 , 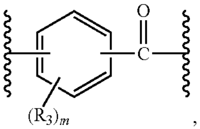 , and

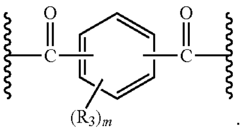 .

n can be an integer selected from 0 to 6. m can be an integer selected from 0 to 4. Each $R_1$ and $R_2$ can be independently selected from hydrogen, methyl, ethyl, and halogen. $R_3$ can be selected from hydrogen, methyl, ethyl, propyl, amino, nitro, cyano, trifluoromethyl, alkoxy, azido, and halogen.

Also disclosed herein is a glucose-triptolide conjugate with the structure of Formula (II), or a pharmaceutically acceptable salt or solvate, a stereoisomer, a diastereoisomer or an enantiomer thereof.

Formula (II)

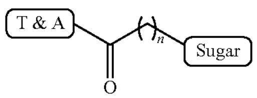

In some embodiments, n can be an integer selected from 0 to 10. In some embodiments, n can be 3. T & A moiety can be triptolide or one of its analogs. In some embodiments, T & A moiety can be selected from

TA1

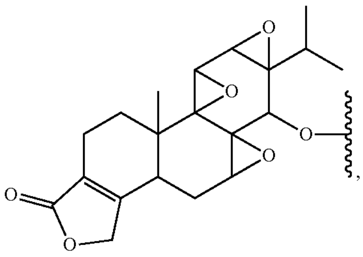

-continued

TA2

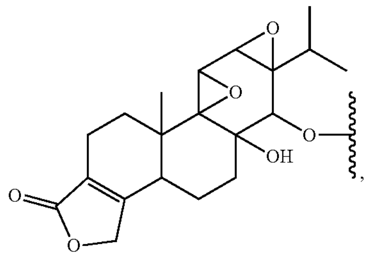

TA3

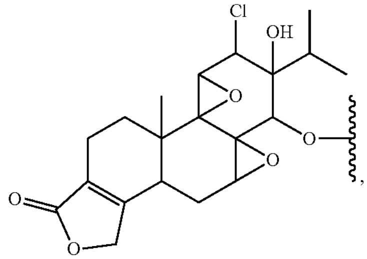

TA4

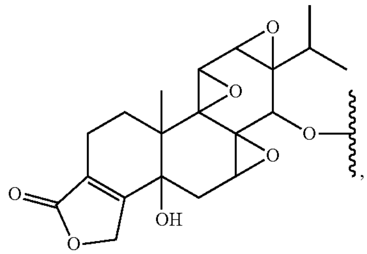

TA5

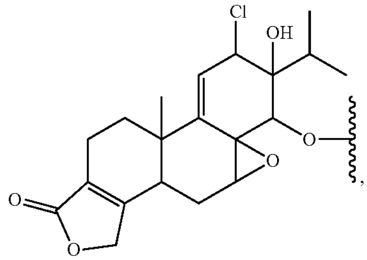

TA6

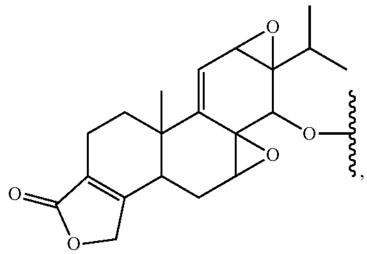

TA7

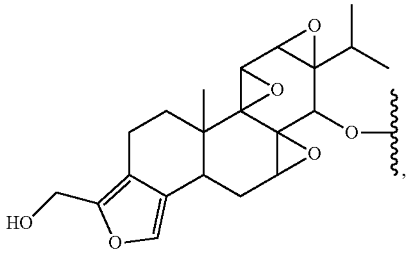

-continued
TA8
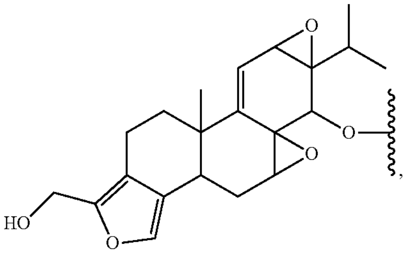
TA9
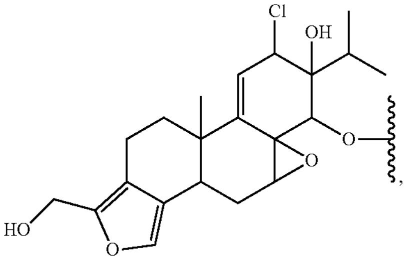
TA10
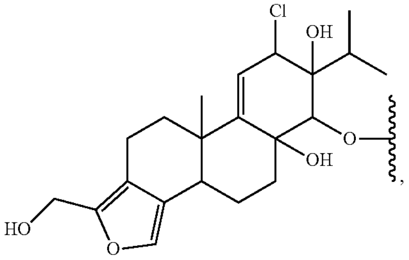
TA11
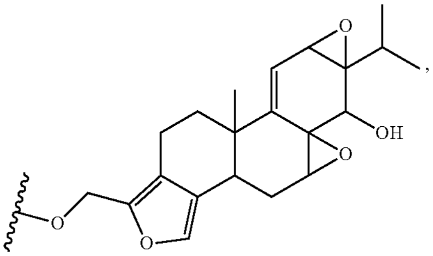
TA12
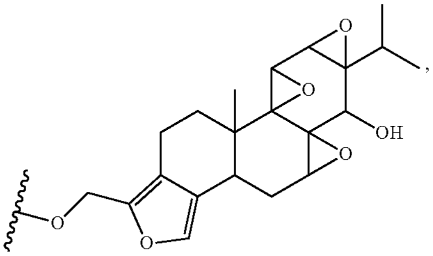
TA13
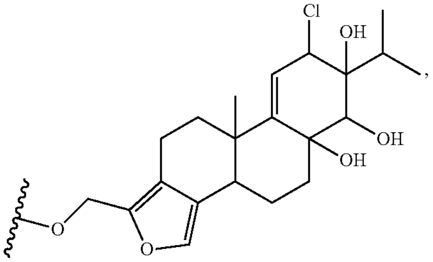
-continued
TA14
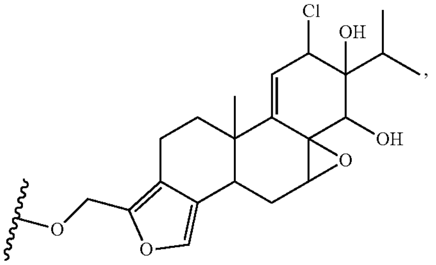
TA15
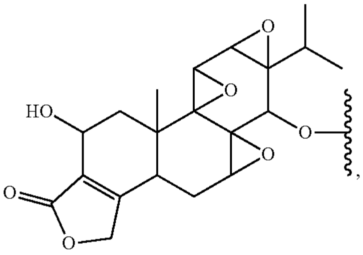
TA16
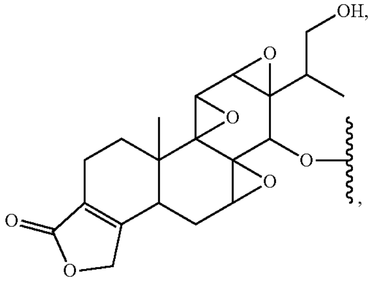
TA17
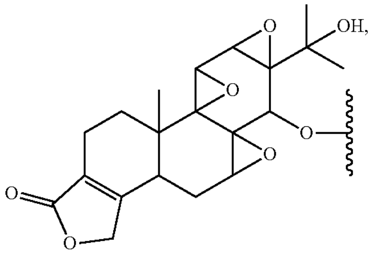
and a pharmaceutically acceptable salt or solvate, a stereoisomer, a diastereoisomer or an enantiomer thereof.
In some embodiments, Sugar moiety can be selected from
sugar 1
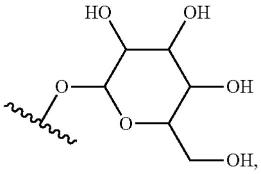

-continued
sugar 2
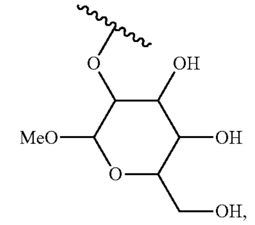
sugar 3
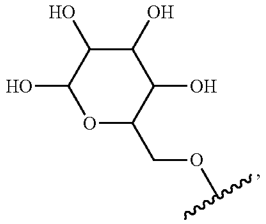
sugar 4
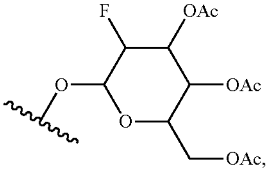
sugar 5
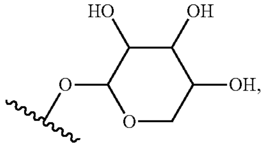
sugar 6
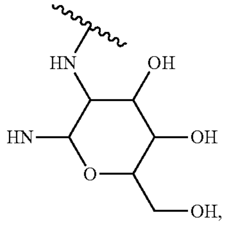
sugar 7
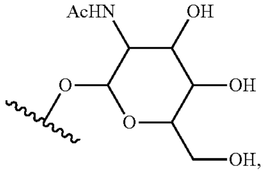
sugar 8
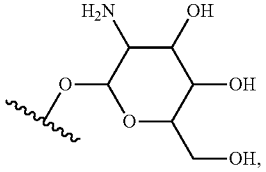
sugar 9
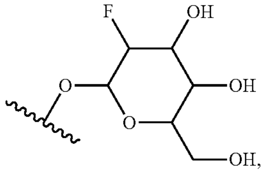
-continued
sugar 10
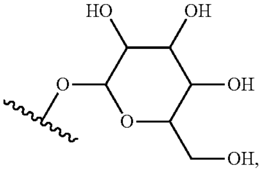
sugar 11
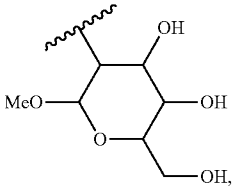
sugar 12
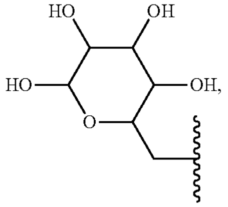
sugar 13
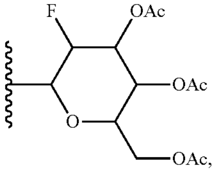
sugar 14
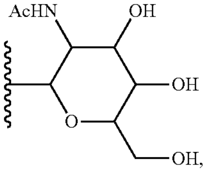
sugar 15
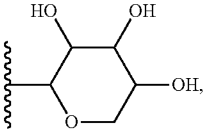
sugar 16
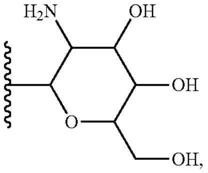
sugar 17
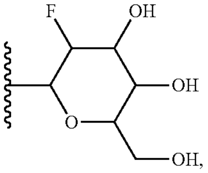
sugar 18
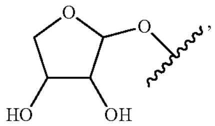

-continued sugar 19

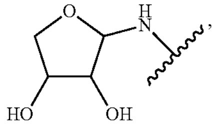

sugar 20

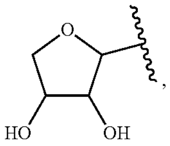

and a pharmaceutically acceptable salt or solvate, a stereoisomer, a diastereoisomer or an enantiomer thereof.

Further herein is a glucose-triptolide conjugate with the structure of Formula (III), or a pharmaceutically acceptable salt or solvate, a stereoisomer, a diastereoisomer or an enantiomer thereof.

Formula (III)

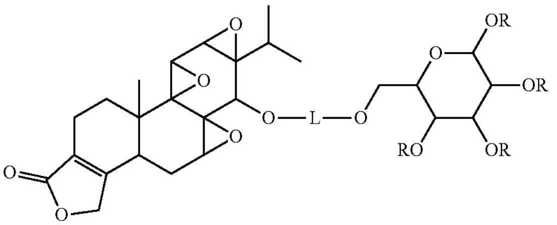

In some embodiments, L can be selected from —X—Y—Z—, wherein X and Z can individually and independently be a direct bond, —$CH_2$—, —C(O)—, —SO—, —$SO_2$—, —OPO—, —$OPO_2$—, and wherein Y is a direct bond, a substituted or unsubstituted —($C_1$-$C_6$)alkyl-, substituted or unsubstituted —$(CH_2)_n$O($C_1$-$C_6$)alkyl-, substituted or unsubstituted —$(CH_2)_n$C(O)($C_1$-$C_6$)alkyl-, substituted or unsubstituted —$(CH_2)_n$C(O)O($C_1$-$C_6$)alkyl-, substituted or unsubstituted —$(CH_2)_n$NH($C_1$-$C_6$)alkyl-, substituted or unsubstituted —$(CH_2)_n$C(O)NH($C_1$-$C_6$)alkyl-, substituted or unsubstituted —$(CH_2)_n$S(C1-C6)alkyl-, substituted or unsubstituted —$(CH_2)_n$C(O)$(CH_2)_n$S($C_1$-$C_6$)alkyl-, substituted or unsubstituted —($C_2$-$C_6$)alkenyl-, substituted or unsubstituted —$(CH_2)_n$O($C_2$-$C_6$)alkenyl-, substituted or unsubstituted —$(CH_2)_n$C(O)($C_2$-$C_6$)alkenyl-, substituted or unsubstituted —$(CH_2)_n$C(O)O($C_2$-$C_6$)alkenyl-, substituted or unsubstituted —$(CH_2)_n$NH($C_2$-$C_6$)alkenyl-, substituted or unsubstituted —$(CH_2)_n$C(O)NH($C_2$-$C_6$)alkenyl-, substituted or unsubstituted —$(CH_2)_n$S($C_2$-$C_6$)alkenyl-, substituted or unsubstituted —$(CH_2)_n$C(O)$(CH_2)_n$S($C_2$-$C_6$)alkenyl-, substituted or unsubstituted —($C_2$-$C_6$)alkynyl-, substituted or unsubstituted —$(CH_2)_n$O($C_2$-$C_6$)alkynyl-, substituted or unsubstituted —$(CH_2)_n$C(O)($C_2$-$C_6$)alkynyl-, substituted or unsubstituted —$(CH_2)_n$C(O)O($C_2$-$C_6$)alkynyl-, substituted or unsubstituted —$(CH_2)_n$NH($C_2$-$C_6$)alkynyl-, substituted or unsubstituted —$(CH_2)_n$C(O)NH($C_2$-$C_6$) alkynyl-, substituted or unsubstituted —$(CH_2)_n$S($C_2$-$C_6$) alkynyl-, substituted or unsubstituted —$(CH_2)_n$C(O)$(CH_2)_n$S($C_2$-$C_6$)alkynyl-, wherein each alkyl, alkenyl and alkynyl group may be optionally substituted with alkyl, alkoxy, amino, hydroxyl, oxo, aryl, heteroaryl, carboxyl, cyano, nitro, azido, or trifluoromethyl. n can be an integer selected from 0 to 6. Each R can be independently selected from the group consisting of hydrogen, alkyl, and acetyl group.

In some embodiments, L can be selected from —CO$(CR_1R_2)_n$CO—, —$(CR_1R_2)_n$CO—, —CO$(CR_1R_2)_n$—, —$(CR_1R_2)_n$SO—, —$(CR_1R_2)_n$$SO_2$—, —SO$(CR_1R_2)_n$—, —$SO_2$$(CR_1R_2)_n$—, —SO$(CR_1R_2)_n$SO—, —$SO_2$$(CR_1R_2)_n$$SO_2$—,

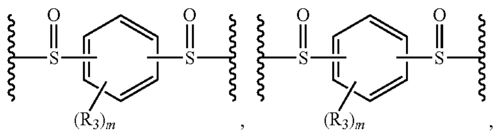

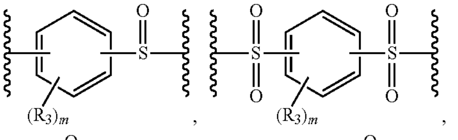

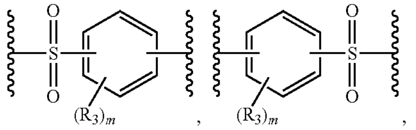

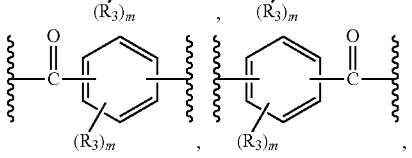

and

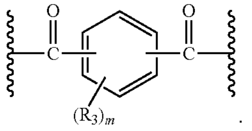

n can be an integer selected from 0 to 6. m can be an integer selected from 0 to 4. Each $R_1$ and $R_2$ can be independently selected from hydrogen, methyl, ethyl, and halogen. $R_3$ can be selected from hydrogen, methyl, ethyl, propyl, amino, nitro, cyano, trifluoromethyl, alkoxy, azido, and halogen.

Provided are compounds generated by conjugation of triptolide with glucose to form glucose-triptolide conjugates by the Linker. The Linker can be selected from 4-hydroxybutanoic acid, phthalic acid, 1,5-pentanedioic acid, succinic acid and so on. The synthetic routes are effective and could provide gram-scale glucose-triptolide conjugates. Compound 1 is very effective against cancer cells under hypoxia in contrast to most if not all existing cytotoxic drugs, likely due to the increase in GLUT expression under hypoxic conditions.

In some embodiments, the synthesis of glucose-triptolide conjugates can follow the below steps are as follows:

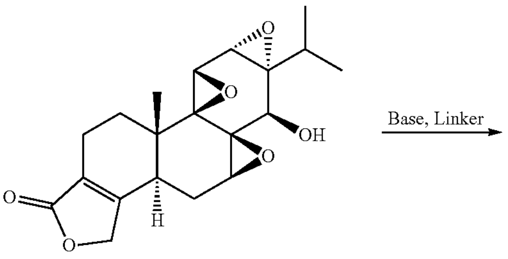

Triptolide

-continued

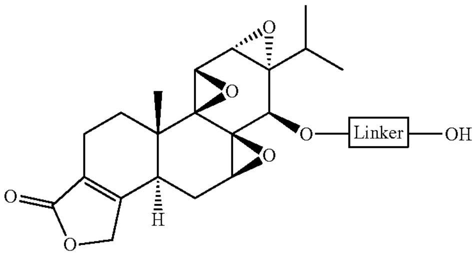

T1

Step 1: The synthesis of T1 commenced with the acylation of the C14 hydroxy group of triptolide with the Linker.

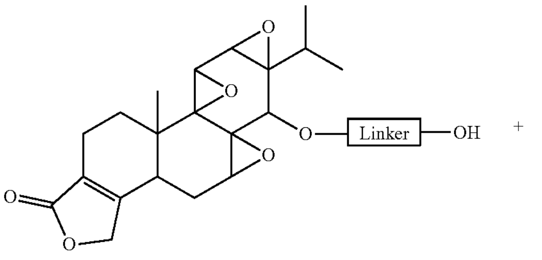

T1

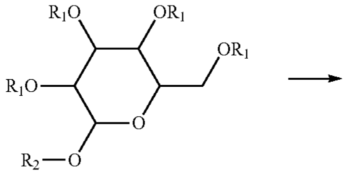

T2

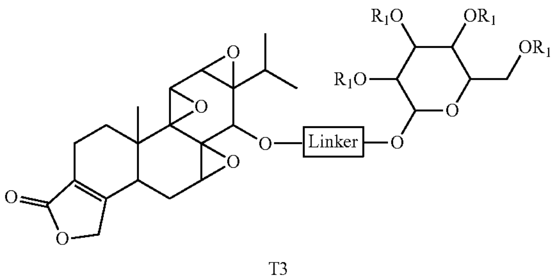

T3

Step 2: Introduction of sugar group. The synthesis of Glu-Triptolide condensated type Schmidt donor or tetra-O-protected-D-glucopyranose T2 with triptolide Linker derivative T1 to give intermediate T3. $R_1$ can be respectively selected from $C_1$-$C_6$ alkyl acyl protective group, substituted or unsubstituted benzoyl protective group, silicon-based protective group, substituted or unsubstituted benzyl protective group, substituted or unsubstituted allyl protective group and so on; $R_1$ can be preferentially selected from para-methoxylbenzyl, 1-chloroacetyl protective group, triethylsilyl, and benzyl. $R_2$ is hydrogen or $CNHCCl_3$.

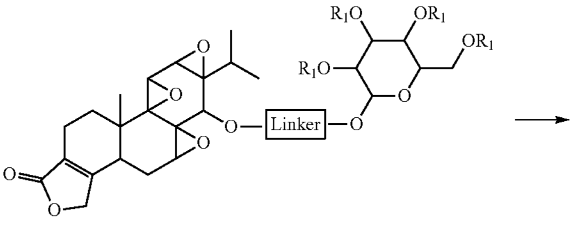

T3

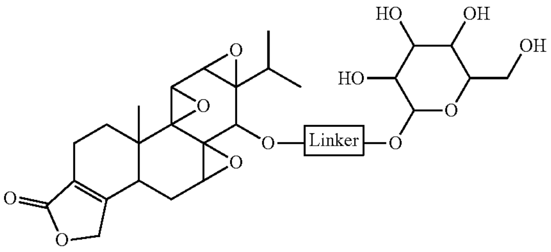

T4

Step 3: Deprotection of T3 can provides Glutriptolide T4.

Alternatively, the synthesis of glucose-triptolide conjugates can follow the below steps:

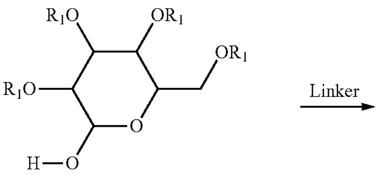

T5

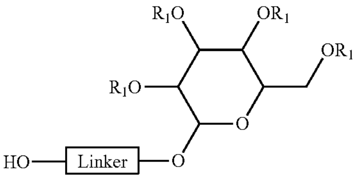

T6

Step 1: Conjugation of glucose with the Linker. The synthesis of tetra-O-protected-D-glucopyranose T6 commenced with the acylation of the hydroxy group of T6 with the Linker. $R_1$ can be respectively selected from $C_1$-$C_6$ alkyl acyl protective group, substituted or unsubstituted benzoyl protective group, silicon-based protective group, substituted or unsubstituted benzyl protective group, substituted or unsubstituted allyl protective group and so on; $R_1$ can be preferentially selected from para-methoxylbenzyl, 1-chloroacetyl protective group, triethylsilyl, and benzyl.

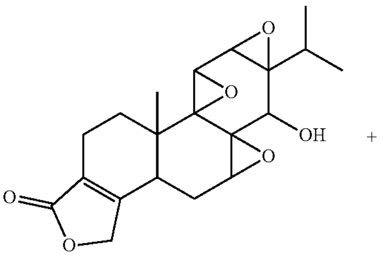

Triptolide

-continued

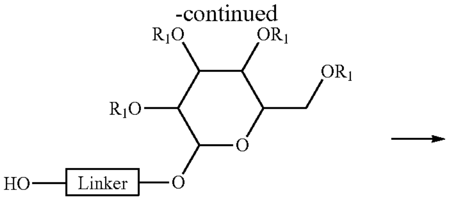

T6

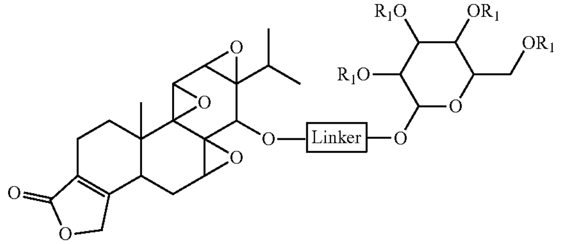

T3

Step 2: Introduction of triptolide. The synthesis of GluTriptolide condensated Glucose Linker derivative T2 with triptolide to give intermediate T3. $R^1$ can be respectively selected from $C_1$-$C_6$ alkyl acyl protective group, substituted or unsubstituted benzoyl protective group, silicon-based protective group, substituted or unsubstituted benzyl protective group, substituted or unsubstituted allyl protective group and so on; $R_1$ can be preferentially selected from para-methoxylbenzyl, 1-chloroacetyl protective group, triethylsilyl, and benzyl.

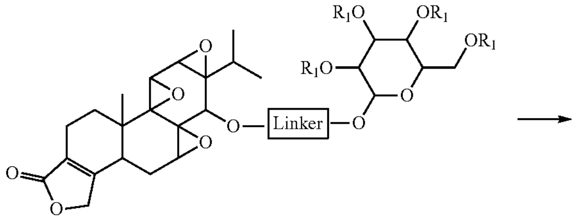

T3

-continued

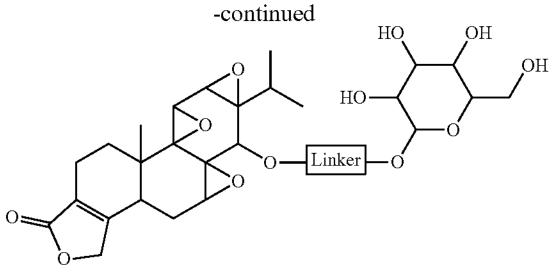

T4

Step 3: Deprotection of T3 can provides Glutriptolide T4.

Design and synthesis of compound 1 as the most potent inhibitor of cancer cell proliferation among glucose-triptolide conjugates are described as below. Glutriptolides can be divided into three structural components: glucose, triptolide and a linker. The first generation glutriptolide-1 (compound 10) contained a four-carbon succinate linker, giving rise to an activation intermediate previously shown to cause toxicity in humans. We thus selected a series of new linkers to connect glucose and triptolide (Table 1). Briefly, those linkers attached at the C2 position of glucose include γ-hydroxybutyric acid (compound 1), addition of two methyl groups to the succinate backbone (compounds 2 and 3), incorporation of a phenyl group into the succinate backbone (compounds 4 and 5), an elongation of the succinate linker by one carbon (compounds 6 and 7). In addition, we synthesized two derivatives that contained a C6 substituted glucose with succinate linkers (compounds 8 and 9). We then determined the potency of the newly synthesized glutriptolides in a HEK293T cell proliferation assay (Table 1). As expected, glutriptolides have lower potency than triptolide itself. Among the second-generation glutriptolides, compound 1 is significantly more potent than compound 10 with an $IC_{50}$ (71 nM) that is less that 13-fold higher than that for triptolide (5.6 nM). The rest of the new glutriptolide analogs were less potent than compound 10 except for compound 8. But unlike compound 1, compound 8 would release the same toxic triptolide-succinate intermediate upon activation as compound 10. Thus, the ensuing studies were focused on the characterization of compound 1.

TABLE 1

Chemical structures of triptolide (TPL) and glucose-conjugated triptolides.

| Compounds | Chemical Structure |
|---|---|
| TPL | 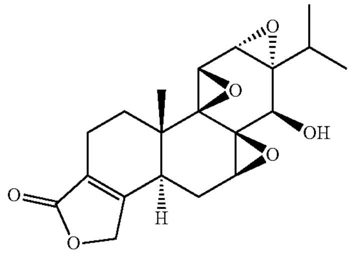 [SMILES: CC(C)[C@]12O[C@H]1[C@@H]1O[C@]13[C@]1(O[C@H]1C[C@H]1C4=C(CC[C@@]13C)C(=O)OC4)[C@@H]2O] |

TABLE 1-continued
| Chemical structures of triptolide (TPL) and glucose-conjugated triptolides. | |
|---|---|
| Compounds | Chemical Structure |
| 1 | 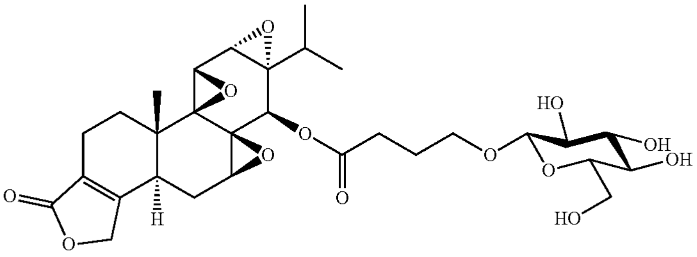 |
| 2 | 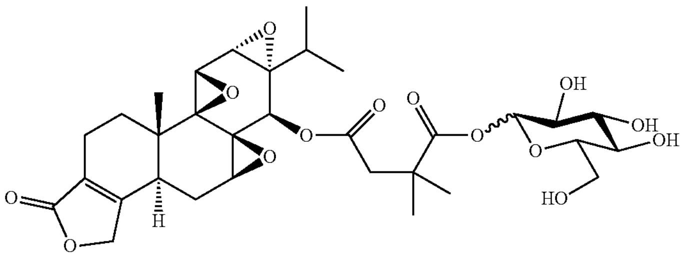 (α:β = 1.1:1.0) |
| 3 | 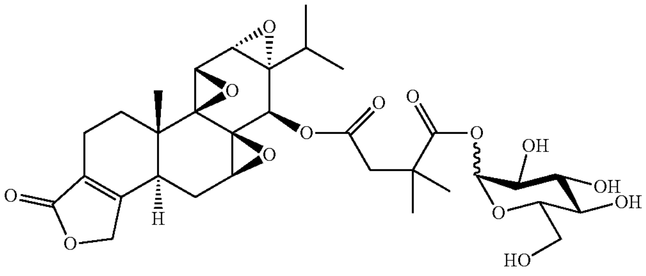 (α:β = 5.2:1.0) |
| 4 | 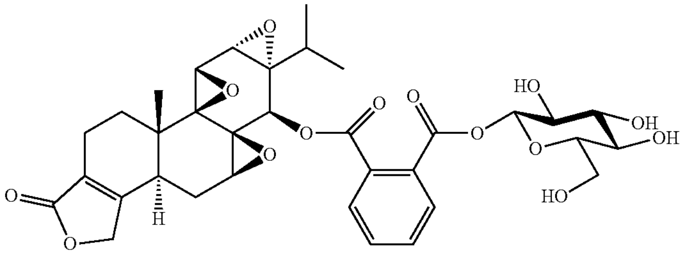 |
| 5 | 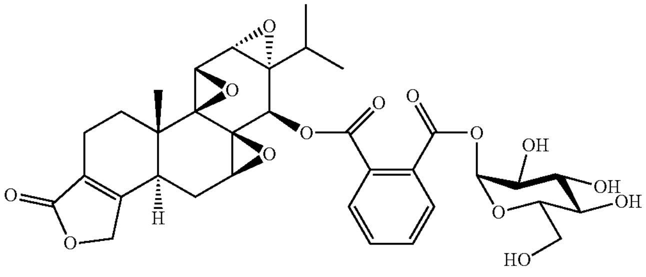 |

TABLE 1-continued

Chemical structures of triptolide (TPL) and glucose-conjugated triptolides.

| Compounds | Chemical Structure |
|---|---|
| 6 | 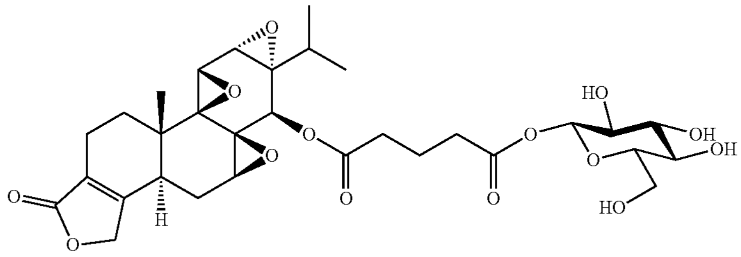 |
| 7 | 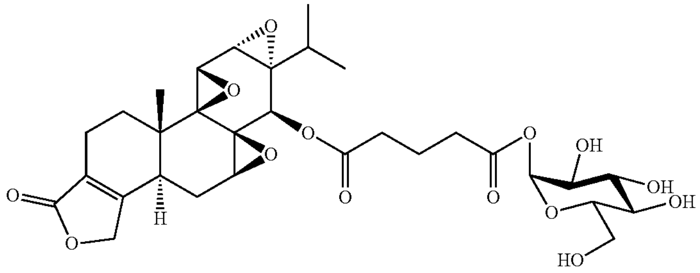 |
| 8 | 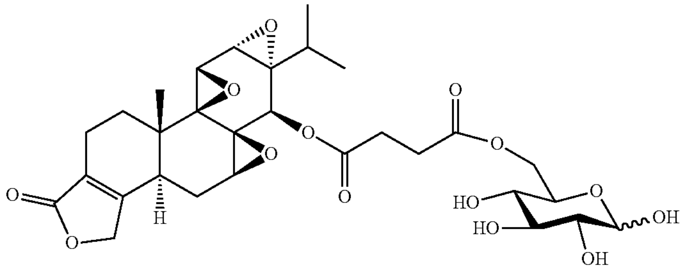 |
| 9 | 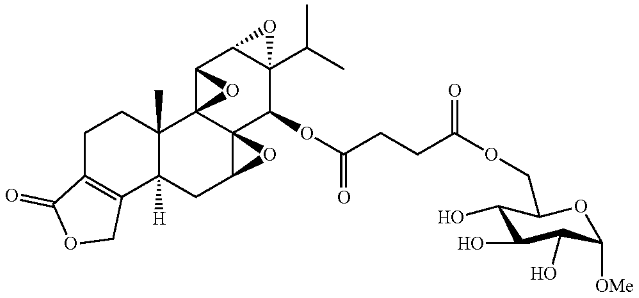 |
| 10 | 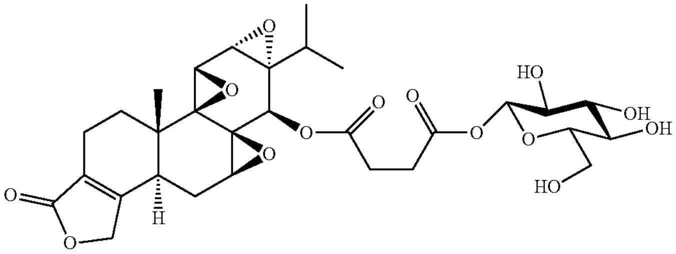 |

FIG. 1 is a proposed scheme illustrating how glutriptolides inhibit the proliferation of a cancer cell, according to some embodiments of the present disclosure.

Design and Synthesis of compound 1 as a potent inhibitor of cancer cell proliferation among glucose-triptolide conjugates. Glutriptolides can be divided into three structural components: glucose, triptolide, and a linker. The first-generation glutriptolide-1 (compound 10) contained a 4-carbon succinate linker, giving rise to an activation intermediate previously shown to be too toxic to be used in humans. We thus selected a series of alternative linkers to connect glucose and triptolide (Table 1). In brief, these linkers attached at the C2 position of glucose include g-hydroxy-butyric acid (compound 1), addition of two methyl groups to the succinate backbone (compounds 2 and 3), incorporation of a phenyl group to the succinate backbone (compounds 4 and 5), and elongation of the succinate linker by one carbon (compounds 6, 7). In addition, we also synthesized two derivatives that contained a C6-substituted glucose with succinate linkers (compounds 8, 9). We then determined the potency of the newly synthesized glutriptolides in a HEK293T cell proliferation assay (Table 1). As expected, glutriptolides have lower potency than triptolide itself. Among the second-generation glutriptolide, compound 1 is significantly more potent than glutriptolide-1 with an IC50 (71 nM) that is about 13-fold higher than that for triptolide (5.6 nM). The rest of the second-generation glutriptolide analogs were less potent than compound 10 except for compound 8. But unlike compounds 1, compound 8 would release the same toxic triptolide-succinate intermediate upon activation as compound 10. Thus, the ensuing studies were focused on the characterization of compound 1, named hereafter as compound 2.

Figure 2A:
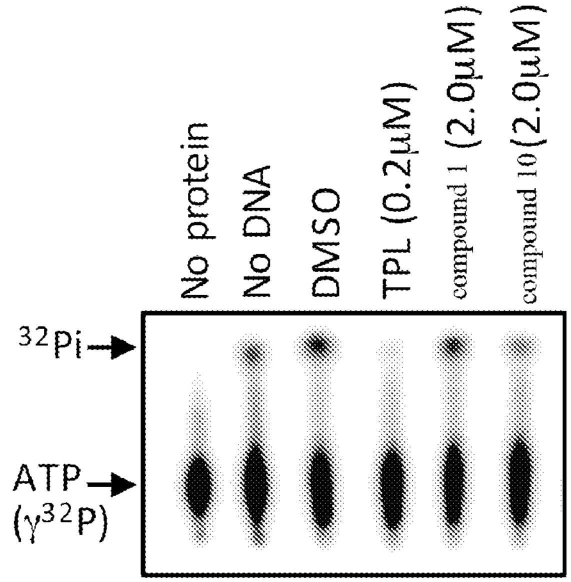
FIGS. 2A-2B show compound 1 does not inhibit the ATPase activity of TFIIH in vitro, whereas triptolide (TPL) effectively suppresses activity at a 10 fold lower concentration. Data, mean±SE of released inorganic phosphate ($^{32}Pi$) relative to DMSO (n=3)
Figure 2B:
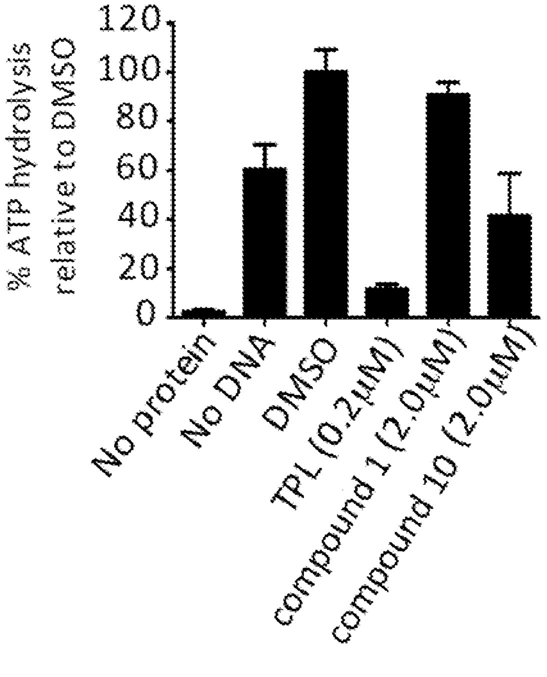
Figure 2C:
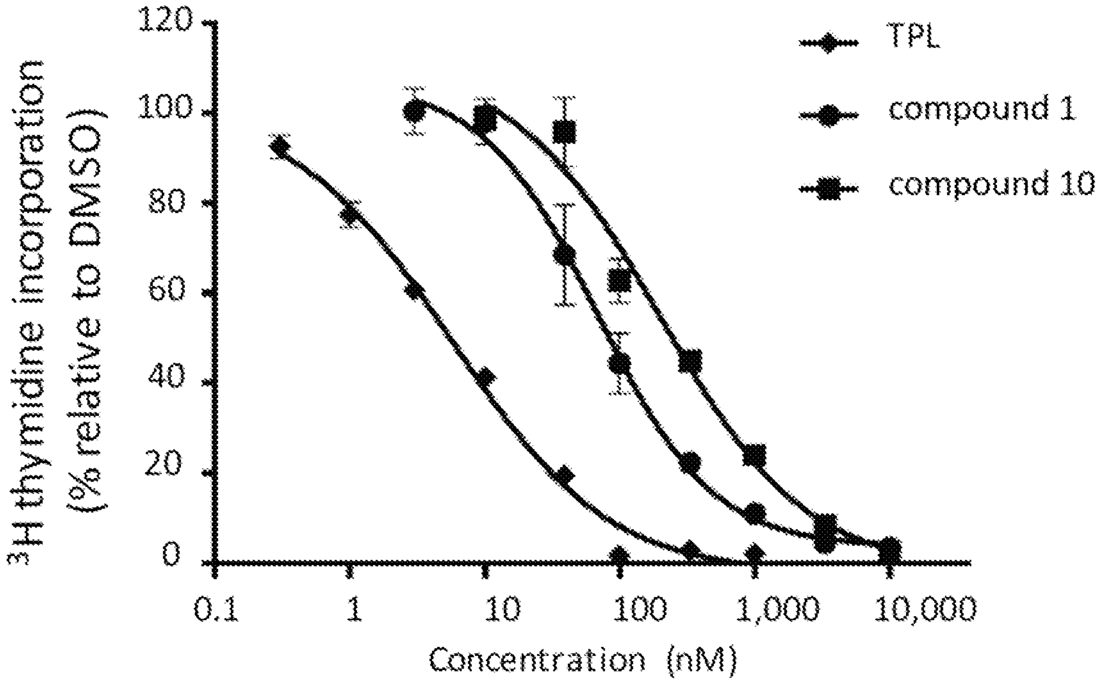
FIG. 2C shows treatment with compound 1 (circle), compound 10 (square) or TPL (diamond) inhibits cell proliferation after 24 hours.
Figure 2D:
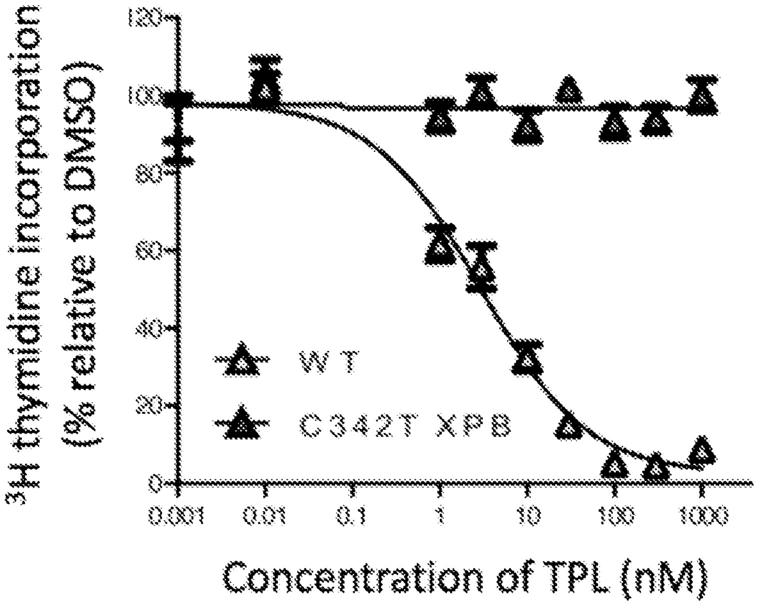
FIG. 2D shows expression of mutant XPB C342T in the knock-in cell line T7115 (dark gray triangle) leads to triptolide resistance but not in the isogenic cell line expressing wild type XPB (gray triangle). Proliferation was measured by $^{3}H$ thymidine incorporation and plotted using GraphPad prism. Data, mean±SE relative to DMSO (n=3)
Figure 2E:
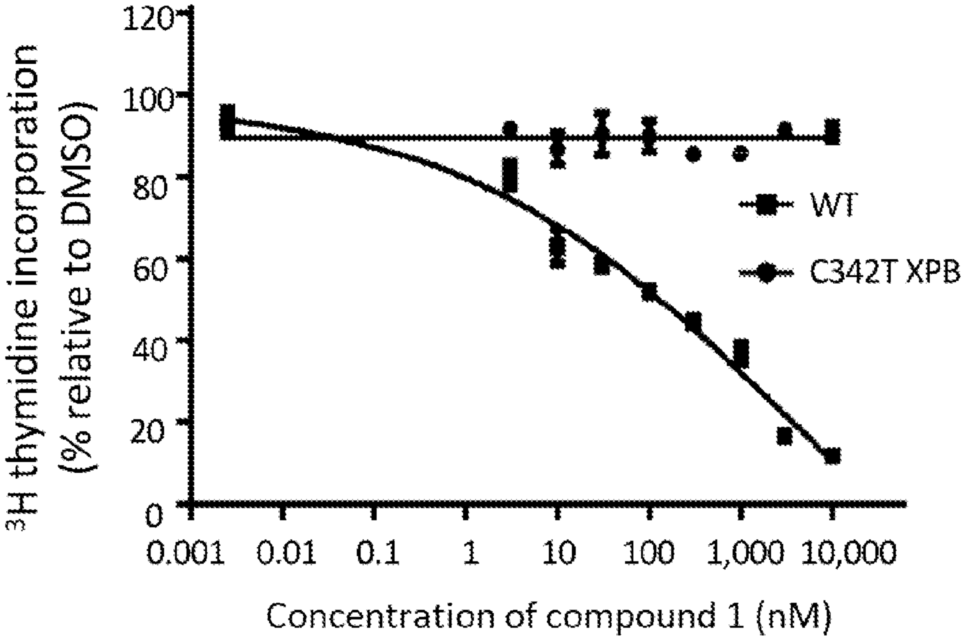
FIG. 2E shows the knock-in cell line for XPB expressing only the C342T XPB mutant is resistant to compound 1 (circle) while inhibition of proliferation is observed in the isogenic cell line expressing wild type (square) XPB. Proliferation was measured by $^{3}H$ thymidine incorporation and plotted using GraphPad prism. Data, mean±SE relative to DMSO (n=3)

Compound 1 is a prodrug that inhibits cell proliferation in an XPB-dependent manner. A premise of our original design of glutriptolides is that these conjugates will serve as prodrugs with little inhibitory effect on XPB until they enter cancer cells where the linkers are cleaved by intracellular hydrolytic enzymes to release active triptolide. We thus determined the effect of compound 1 on the DNA-dependent ATPase activity of purified TFIIH using g-[32P]-ATP as a substrate. Upon hydrolysis, the released 32Pi can be separated from the substrate using thin-layer chromatography and visualized with autoradiography. Although the ATPase activity of TFIIH is nearly completely inhibited by 200 nM triptolide, only a small fraction of the activity was affected by 2 mM compound 1 (FIGS. 2A and 2B). FIGS. 2A-2E show that compound 1 is a prodrug that requires XPB binding for its antiproliferative effect. FIGS. 2A-2B show that compound 1 does not inhibit the ATPase activity of TFIIH in vitro, whereas triptolide (TPL) effectively suppresses activity at a 10-fold lower concentration. Data are represented as mean GSE of released inorganic phosphate ($^{32}$Pi) relative to DMSO (n=3). Although compound 1 has negligible effect on the ATPase activity of recombinant TFIIH, it inhibited HEK293T cell proliferation in a dose-dependent manner, being more potent than compound 10 (FIG. 2C and Table 1). FIG. 2C shows that treatment with compound 1 (circle), compound 10 (square), or TPL (diamond) inhibits cell proliferation after 24 h. These observations suggest that compound 1 is an inactive pro-drug and can be activated inside cells. To determine if the antiproliferative effect of compound 1 is mediated through inhibition of XPB, we took advantage of an engineered mutant cell line T7115 that encodes a single allele of C342T XPB mutant, which was previously shown to be resistant to triptolide (FIG. 2D). FIG. 2D shows that XPB C342T mutation leads to resistance to triptolide. Expression of mutant XPB C342T in the knock-in cell line T7115 (dark gray triangle) leads to triptolide resistance but not in the isogenic cell line expressing wild type XPB (gray triangle). Proliferation was measured by 3H thymidine incorporation and plotted using GraphPad prism. Data represents mean±SEM relative to DMSO (n=3). Although the wild-type (WT) 293T cells were inhibited by compound 1 in a dose-dependent manner, the isogenic T7115 mutant line is resistant to compound 1, suggesting that compound 1 works through inhibition of XPB, necessitating the intracellular hydrolytic release of triptolide from compound 1 (FIG. 2E). FIG. 2E shows that the knock-in cell line for XPB expressing only the C342T XPB mutant is resistant to compound 1 (circle), whereas inhibition of proliferation is observed in the isogenic cell line expressing WT (square) XPB. Proliferation was measured by 3H thymidine incorporation and plotted using GraphPad prism. Data are represented as mean G SEM relative to DMSO (n=3).

Figure 3A:
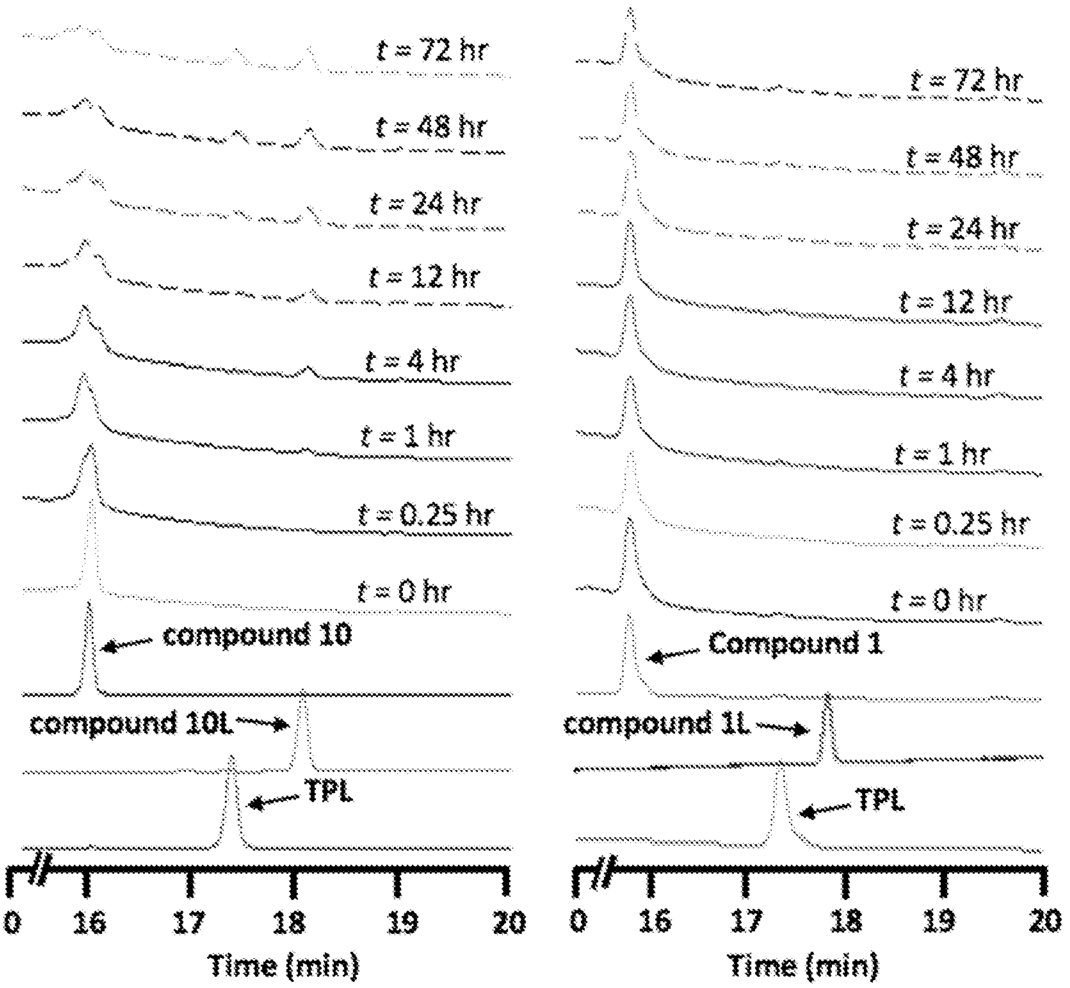
FIG. 3A shows hydrolysis of compound 10 and compound 1 at different incubation times in human serum as monitored by tandem HPLC-MS; chromatograms were taken at $A_{280}$.

Compound 1 has greater stability in human serum and higher selectivity for cancer cells over normal cells than compound 10. For glutriptolides to achieve selectivity toward glucose transporter (GLUT)-overexpressing cancer cells over their normal counterparts, it is imperative that they have sufficiently long half-lives in serum to reduce the amount of free triptolide released in blood prior to their entry into tumor cells. We determined the stability of compounds 10 and 1 by incubating them with human serum and detecting the release of free triptolide. Although compound 10 underwent degradation to produce the triptolide-succinate intermediate by 4 h with appreciable amount of free triptolide generated by 48 h (FIGS. 3A and 3B), compound 1 remained largely intact after incubation in human serum for up to 72 h (FIG. 3A). These results suggest that compound 1 is considerably more stable than compound 10 in human serum.

Figure 3B:
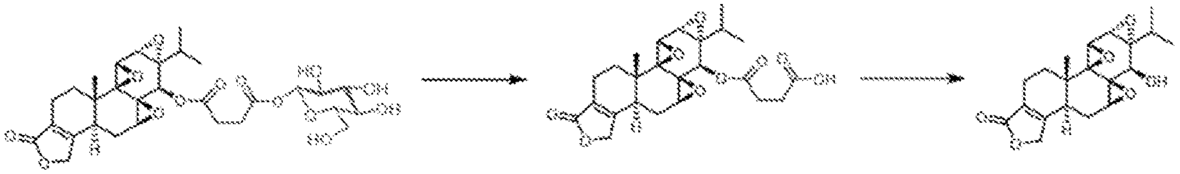
FIG. 3B shows chemical structures of compound 10 and compound 1 with hydrolysis intermediates 10 L and 1 L that can be subsequently hydrolyzed to release triptolide (TPL)
Figure 3B:
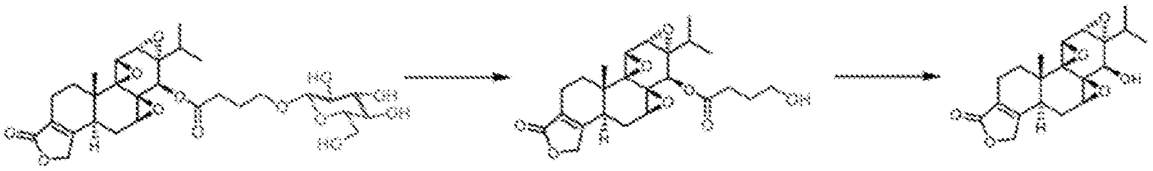

FIGS. 3A-3D show compound 1 possesses increased stability in human serum and lower general toxicity toward nonmalignant, primary cells relative to compound 10. FIG. 3A shows hydrolysis of compounds 10 and 1 at different incubation times in human serum as monitored by tandem HPLC-MS. Chromatograms were taken at $A_{218}$. FIG. 3B shows chemical structures of compounds 10 and 1 with hydrolysis intermediates 10 L and 1 L that subsequently releases triptolide (TPL).

TABLE 2

Bioactivities of compounds 1 and 10 in cancer and primary cells.

| | | | Compound 10 $IC_{50}$ (μM) | Compound 1 $IC_{50}$ (μM) |
|---|---|---|---|---|
| Cancer cell line | Prostate Cancer | PC3 | 0.50 ± 0.10 | 0.6H ± 0.18 |
| | | LNCaP | 0.56 ± 0.09 | 0.45 ± 0.33 |
| | | DU-145 | 0.40 ± 0.13 | 0.44 ± 0.19 |
| | Breast Cancer | MDA-MB-231 | 0.28 ± 0.01 | 0.26 ± 0.10 |
| | | MDA-MB-453 | 0.53 ± 0.20 | 0.53 ± 0.28 |
| | | SK-BR-3 | 1.30 + 1.84 | 2.16 ± 1.59 |
| | Head and Neck Cancer | A253 | 0.71 ± 0.47 | 0.54 ± 0.40 |
| | | Detroit 562 | 1.42 ± 0.83 | 1.24 ± 0.61 |
| | | SCC-25 | 1.26 ± 0.99 | 1.63 ± 0.78 |
| | Melanoma | SK-Mel-3 | 0.42 ± 0.34 | 0.44 ± 0.25 |
| | | SK-Mel-1 | 1.29 + 0.47 | 3.44 + 2.36 |
| | | RPMI-7951 | 2.67 ± 1.34 | 5.95 ± 2.45 |
| | Pancreatic Cancer | CfPAC-1 | 0.51 ± 0.35 | 0.47 ± 0.32 |
| | | BxPC3 | 4.15 ± 0.18 | 5.00 ± 2.83 |
| | | SW1990 | 1.52 ± 0.33 | 6.48 ± 2.79 |
| | Lung Cancer | A549 | 1.70 ± 0.79 | 2.72 ± 1.41 |
| | | NCI-H1299 | 6.40 ± 2.43 | 11.49 ± 5.51 |
| | | NCI-H1437 | N/A | N/A |
| | Liver Cancer | SNU-475 | 3.85 ± 3.26 | 4.60 ± 4.55 |
| | | SK-HEP-1 | 3.38 ± 0.71 | 5.90 ± 0.28 |
| | | SNU-387 | 15.51 ± 9.28 | 24.43 ± 8.90 |
| Primary cells | Normal Cells | Astrocyte | 5.31 ± 4.29 | 10.88 ± 9.66 |
| | | Fibroblast | 5.64 ± 1.28 | 10.61 ± 1.22 |
| | | Airway Epithelial cell | 4.12 ± 1.39 | 7.13 ± 2.84 |
| | | Renal Proximal Tubule | 4.83 ± 1.54 | 5.94 ± 2.21 |

TABLE 2-continued

Bioactivities of compounds 1 and 10 in cancer and primary cells.

| | | | |
|---|---|---|---|
| | Prostate Epithelial cell | 5.27 ± 2.29 | 4.72 ± 3.48 |
| | Mammary Epithelial cell | 2.56 ± 0.29 | 4.31 ± 1.03 |
| | HUVEC | 1.37 ± 0.73 | 3.98 ± 1.15 |
| Cell type | Cancer cell lines (n = 21) | 2.42 ± 2.00 | 3.94 ± 3.26 |
| | Sensitive lines (n = 8) | 0.49 + 0.07 | 0.47 ± 0.06 |
| | Less sensitive lines (n = 13) | 3.70 ± 2.33 | 6.25 ± 3.68 |
| | Non-malignant cells | 4.16 ± 0.93 | 6.80 ± 1.67 |

| Sample comparison T-test[a] | P value[b] |
|---|---|
| Cancer cells compound 10 vs compound 1 (all) | 0.373 |
| sensitive lines | 0.513 |
| less sensitive lines | 0.007 |
| Primary cells compound 10 vs. compound 1 | 0.009 |

Note:
Sensitive cell lines (black) have $IC_{50}$ < 1 μM while less sensitive cancer cell lines (red) have $IC_{50}$ ≥ 1 μM.
Mean $IC_{50}$ values and their standard deviation from three independent experiments are shown.
N/A indicates not applicable due to absence of sigmoidal response in dose curve.
[a]Student T-test done with unequal variance.
[b]P values of $IC_{50}$ for compound 10 versus compound 1.

Figure 3C:
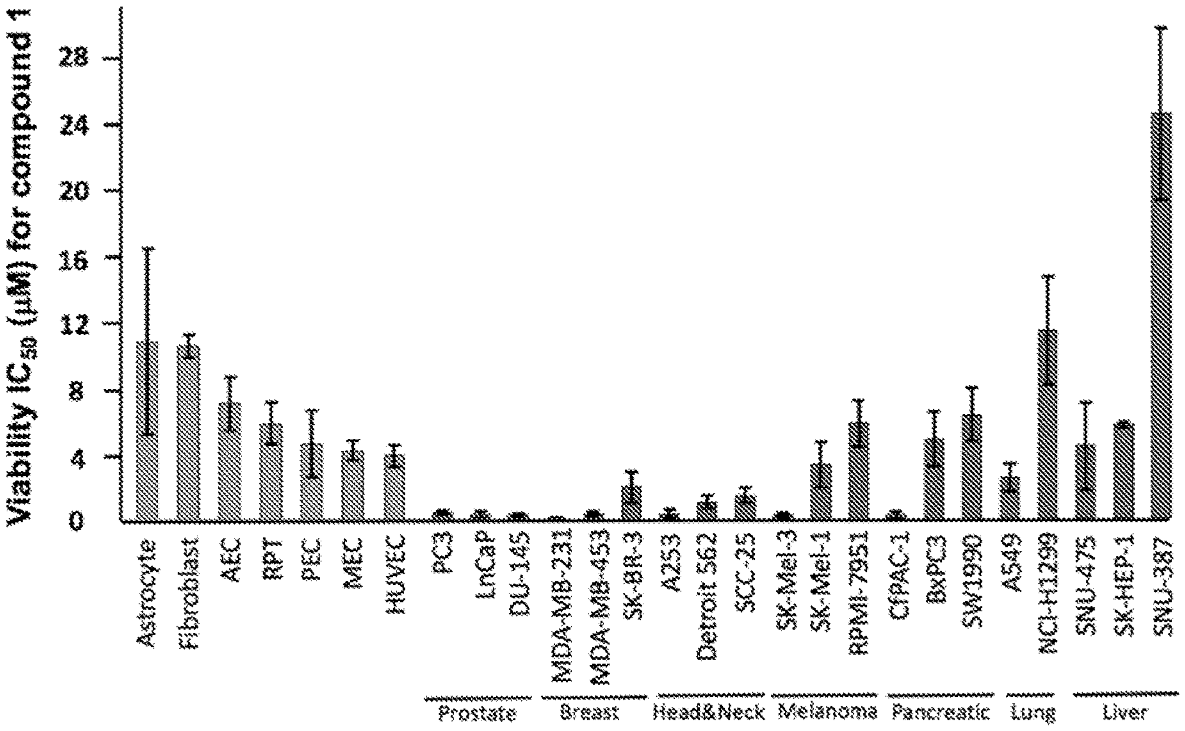
FIG. 3C shows $IC_{50}$s of compound 1 determined by measuring viability using an XTT assay in primary cells and multiple cancer cell lines. Some, liver, lung, melanoma and pancreatic cancer cell lines respond poorly to compound 1 treatment. HUVEC=Human Umbilical Vascular Endothelial Cell, MEC=Mammary Epithelial Cell, PEC=Prostate Epithelial Cell, RPT=Renal Proximal Tubule, AEC=Airway Epithelial Cell. Data, mean±SE viability relative to DMSO (n=3-7)
Figure 3D:
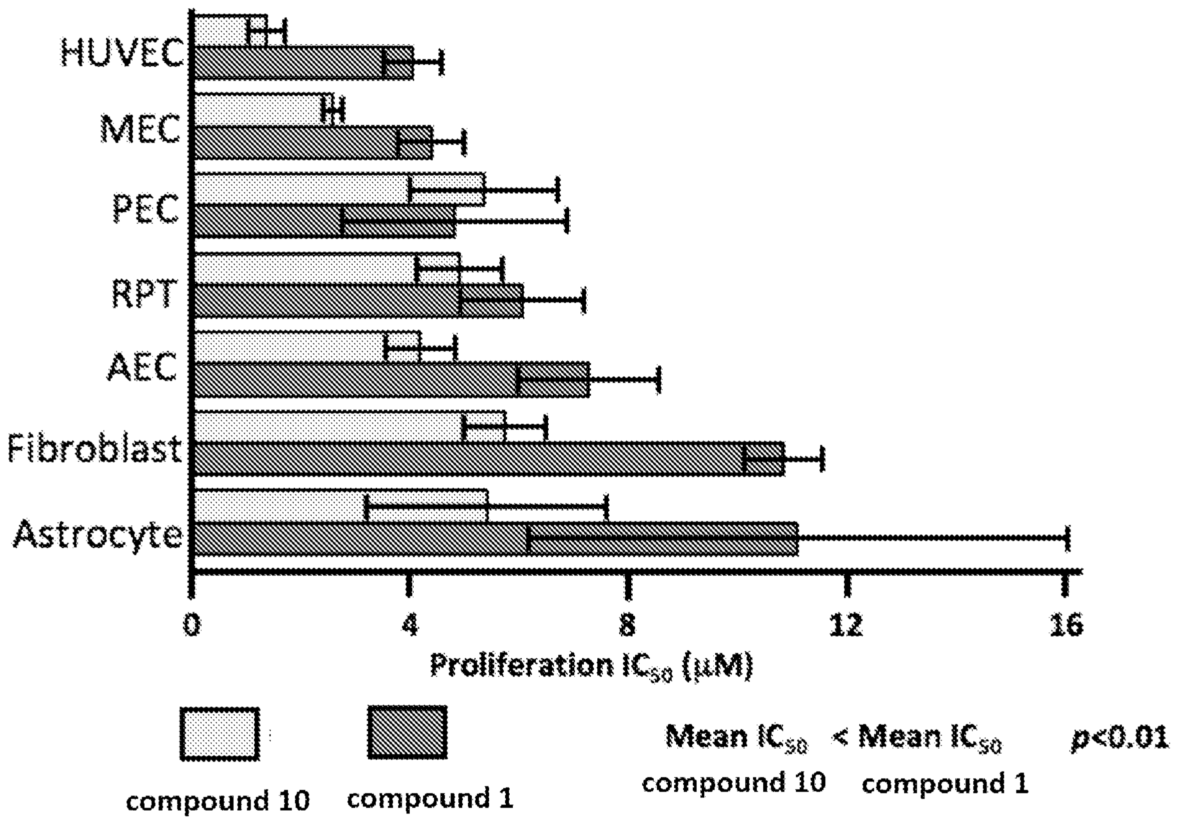
FIG. 3D shows $IC_{50}$ of compound 1 and 10 determined by measuring viability using an XTT assay in primary cells illustrating increased sensitivity to compound 10 relative to compound 1. Mean $IC_{50}$ for compound 10 is significantly lower than mean $IC_{50}$ for compound 1, $p<0.01$. HUVEC=Human Umbilical Vascular Endothelial Cell, MEC=Mammary Epithelial Cell, PEC=Prostate Epithelial Cell, RPT=Renal Proximal Tubule, AEC=Airway Epithelial Cell. Data, mean±SE viability relative to DMSO (n=3-7)

To compare the selectivity of compounds 1 and 10 for cancer cells, we determined their IC50 values for inhibition of cell viability using a panel of normal primary cells, including human umbilical vascular endothelial cell (HUVEC), mammary epithelial cell (MEC), prostate epithelial cell (PEC), renal proximal tubule (RPT), airway epithelial cell (AEC), fibroblasts, and astrocytes. The IC50 values of compound 1 ranged from 4 mM to 10.9 mM for the primary cells, which is significantly higher than those for cancer cell lines that ranged from 0.26 mM to 6.5 mM (with the exception of a liver cell line SNU-387 and lung cell line NCI-H1299) (FIG. 3C, Table 2). FIG. 3C shows primary cell viability as measured by XTT assay exhibits reduced sensitivity to compound 1 in comparison to multiple cancer cell lines. Liver, lung, melanoma, and pancreatic cancer cell lines respond poorly to compound 1 treatment. HUVEC=Human Umbilical Vascular Endothelial Cell, MEC=Mammary Epithelial Cell, PEC=Prostate Epithelial Cell, RPT=Renal Proximal Tubule, AEC=Airway Epithelial Cell. Data are represented as mean G SEM viability relative to DMSO (n=3-7). This represents a significant improvement over compound 10 that had lower IC50 values for each primary cell type and comparable IC50 values for most cancer cell lines (FIG. 3D and Table 2). FIG. 3D shows compound 1 is less toxic than compound 10 in primary cells. Primary cells show increased sensitivity to compound 10 in comparison to compound 1 as measured by XTT viability assay. Mean IC50 for compound 10 is significantly lower than mean IC50 for compound 1, p<0.01. HUVEC=Human Umbilical Vascular Endothelial Cell, MEC=Mammary Epithelial Cell, PEC=Prostate Epithelial Cell, RPT=Renal Proximal Tubule, AEC=Airway Epithelial Cell. Data represents mean±SEM viability relative to DMSO (n=3-7). We also note that cancer cell lines seem to segregate in their sensitivity to compounds 1 and 10 according to tissue or organ origin. With the limited number of cancer cell lines tested, prostate and breast cancer cells appear to be more sensitive than liver and lung cancer cells (FIG. 3C, Table 2).

Figure 4A:
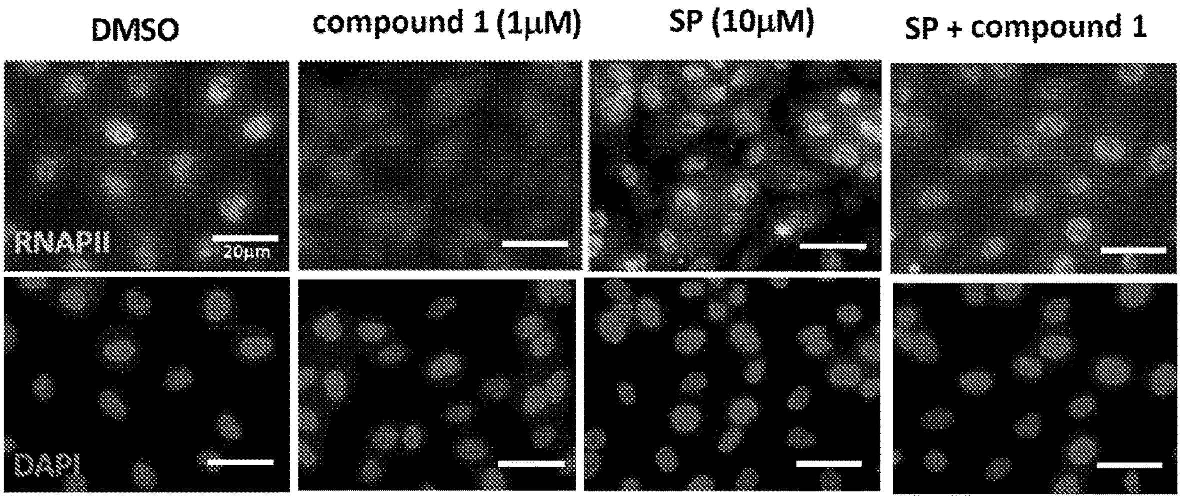
FIGS. 4A and 4B shows the effect of treatment of HeLa cells with DMSO (control), compound 1 (1 μM), spironolactone (10 μM), or pretreatment with spironolactone (10 μM) followed by compound 1 (1 μM). Treatment with 1 μM compound 1 for 24 h depletes endogenous RNA Polymerase II (RNAPII); while, 10 μM spironolactone (SP) and DMSO by themselves do not affect protein levels in fixed HeLa cells processed for immunocytochemical staining of Rpb1 (catalytic subunit of RNAPII) and DAPI (nuclear marker). Pretreatment of cells with 10 μM spironolactone significantly ($P<0.001$) rescues endogenous RNAPII from compound 1 induced degradation. Representative images of Rpb1 and DAPI staining are shown with quantification of intracellular Rpb1 and student's t-test analysis. Data, mean±SE Rpb1 levels relative to DMSO (n=3). Scale bar is 20 μm.
Figure 4B:
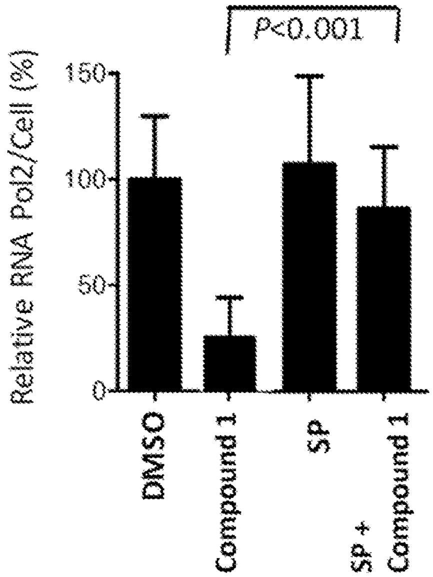
Figure 4C:
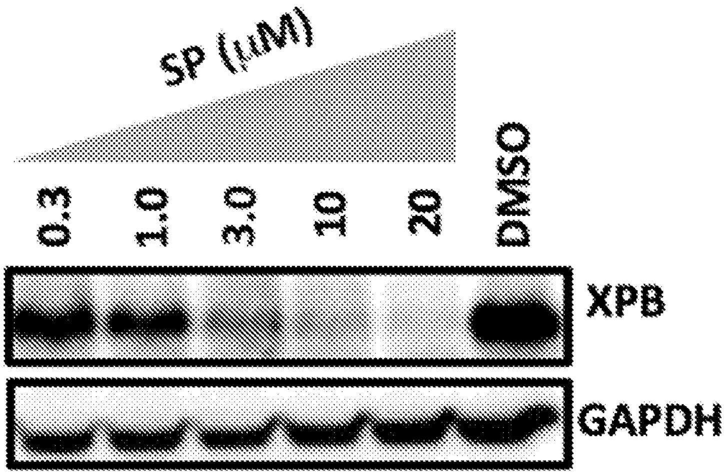
FIG. 4C shows whole cell lysates of cells treated with increasing concentrations of spironolactone (SP) subjected to western blot analysis using antibodies specific for XPB, which shows that spironolactone induces the degradation of endogenous XPB in cells in a dose dependent manner, GAPDH was used a loading control.
Figure 4D:
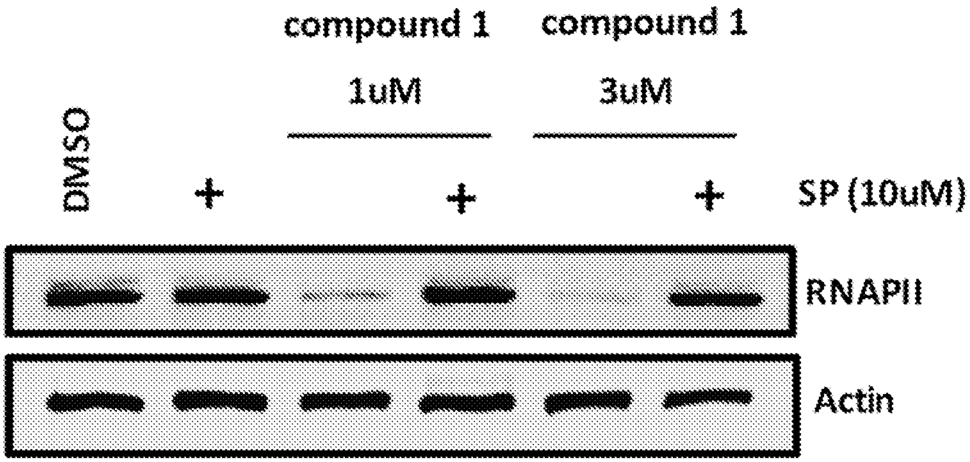
FIG. 4D shows whole cell lysates of cells treated with compound 1, SP or a combination of compound 1 and SP that were subjected to western blot analysis of endogenous RNAPII using antibodies specific for Rpb1 showing that compound 1 induced RNAPII degradation at 1 and 3 μM is antagonized by 10 μM SP treatment.
Figure 4E:
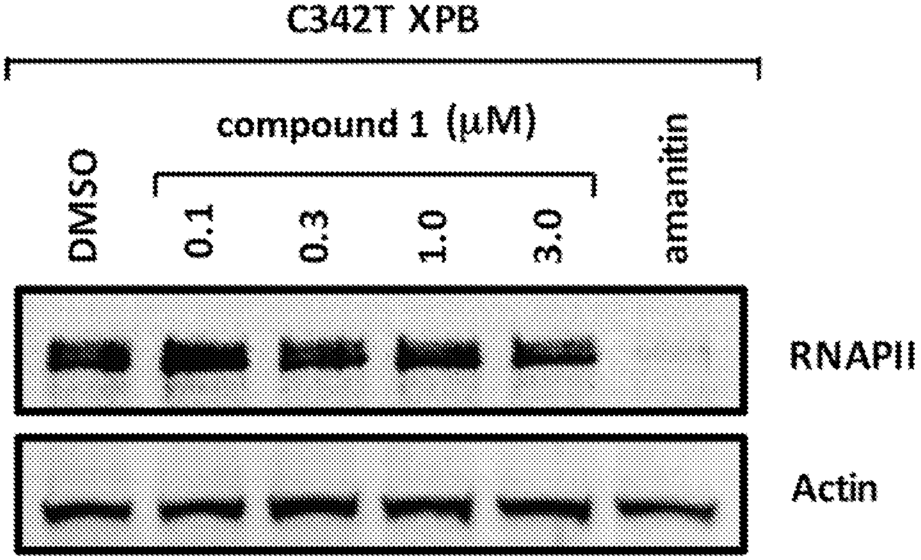
FIG. 4E shows whole cell lysates from isogenic knock-in cells expressing only C342T XPB at increasing concentrations of compound 1 relative to a DMSO control illustrating that degradation of the catalytic subunit of RNAPII by compound 1 as measured by immunoblotting for Rpb1 is inhibited in the absence of wild type XPB. In contrast, the Rbp1 interacting inhibitor α-amanitin induced the degradation of Rpb1 at 1 μM in the C342T XPB isogenic cell line. Actin was used as a loading control.
Figure 4F:
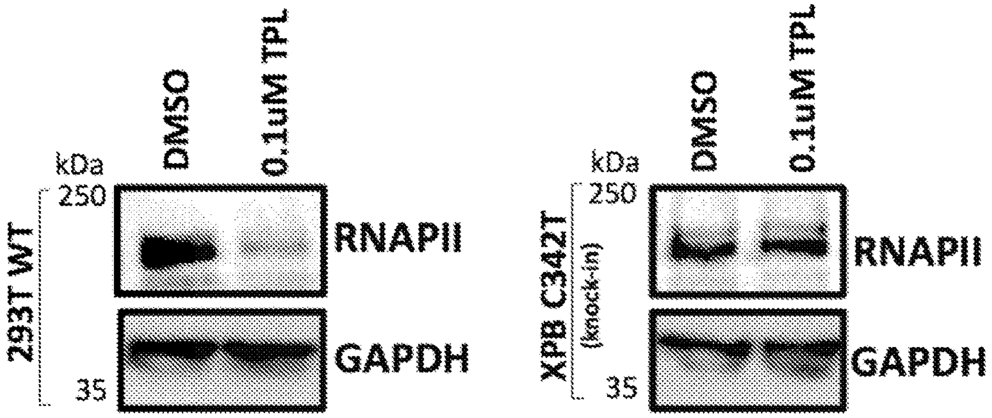
FIG. 4F shows isogenic cells with wild type (293T WT) or triptolide resistant mutant (XPB C342T) XPB treated with 0.1 μM triptolide then lysed for western blot analysis using anti-Rpb1 specific antibodies. Treatment with triptolide leads to the degradation of the Rpb1 subunit of RNAPII degradation in WT XPB cells in contrast to triptolide exposed cells with XPB C342T mutation where Rpb1 levels resemble DMSO control. GAPDH was used a loading control.

Compound 1 causes degradation of the catalytic RPB1 subunit of RNAPII through interaction with XPB. We and others have previously shown that triptolide induced the degradation of the catalytic RPB1 subunit of RNAPII, which is one of the hallmark cellular effects of triptolide. Using immunostaining, we observed that compound 1 also caused the degradation of RPB1 in HeLa cells (FIG. 4A). FIGS. 4A-4F shows compound 1-induced RNA polymerase 2 degradation is XPB dependent. FIGS. 4A-4B show treatment with 1 mM compound 1 for 24 h depletes endogenous RNA polymerase II (RNAPII), whereas 10 mM spironolactone (SP) or DMSO by themselves do not affect protein levels in fixed HeLa cells processed for immunocytochemical staining of RPB1 (catalytic subunit of RNAPII) and DAPI (nuclear marker). Pre-treatment of cells with 10 mM spironolactone significantly (P<0.001) rescues endogenous RNAPII from compound 1-induced degradation. Representative images of RPB1 and DAPI staining are shown with quantification of intracellular RPB1 and student's t test analysis. Data are represented as mean G SE RPB1 levels relative to DMSO (n=3). Aside from triptolide, a known steroidal drug spironolactone (SP) has been reported to bind XPB. Unlike triptolide, however, SP induces proteasome-mediated degradation of XPB without overt cellular toxicity. At 10 mM, SP caused degradation of the majority of XPB (FIG. 4C) but had no effect on the stability of RPB1 (FIG. 4B). FIG. 4C shows spironolactone degrades XPB while triptolide requires wild type XPB for the degradation of Rpb1. Whole cell lysates of cells treated with increasing concentrations of spironolactone (SP) were subjected to western blot analysis using antibodies specific for XPB shows that spironolactone induces the degradation of endogenous XPB in cells in a dose dependent manner. To determine whether depletion of XPB by SP antagonizes the degradation of RPB1 by triptolide released from glutriptolide, we treated cells with a combination of 1 mM compound 1 and 10 mM SP. Co-treatment with SP rescued RPB1 from degradation induced by compound 1. Similar results were obtained using western blot analysis to detect endogenous levels of RPB1 protein (FIG. 4D). FIG. 4D shows whole cell lysates of cells treated with compound 1, SP, or in combination were subjected to western blot analysis of endogenous RNAPII using antibodies specific for RPB1 showing that compound 1-induced RNAPII degradation at 1 or 3 mM is antagonized by 10 mM SP. To further confirm that RPB1 degradation induced by compound 1 required binding of released triptolide to XPB, we determined the level of RPB1 upon treatment of both WT and C342T mutant cell lines. Although degradation of RPB1 was observed in the presence of compound 1 in WT cells (FIG. 4D), RPB1 level remained stable even when the concentration of compound 1 reached 3 mM in the C342T XPB mutant cell line (FIG. 4E). FIG. 4E shows whole cell lysates from isogenic knock-in cells expressing only C342T XPB, which show that degradation of the catalytic subunit of RNAPII by compound 1 as measured by immunoblotting for RPB1 is inhibited in the absence of WT XPB. In contrast, the RPB1-interacting inhibitor a-amanitin induced the degradation of Rpb1 at 1 mM in the C342T XPB isogenic cell line. Actin was used as a loading control. Scale bar, 20 mm. This result corroborates with observations made with SP and triptolide (FIG. 4F), suggesting that the degradation of RPB1 induced by compound 1 requires the covalent binding of released triptolide from compound 1 to XPB. FIG. 4F shows isogenic cells with wild type (293T WT) or triptolide resistant mutant (XPB C342T) XPB were treated with 0.1 mM triptolide then lysed for western blot analysis using anti-Rpb1 specific antibodies. Treatment with triptolide leads to the degradation of the Rpb1 subunit of RNAPII degradation in WT XPB cells in contrast to triptolide exposed cells with XPB C342T mutation where Rpb1 levels resemble DMSO control. GAPDH was used a loading control.

Figure 5A:
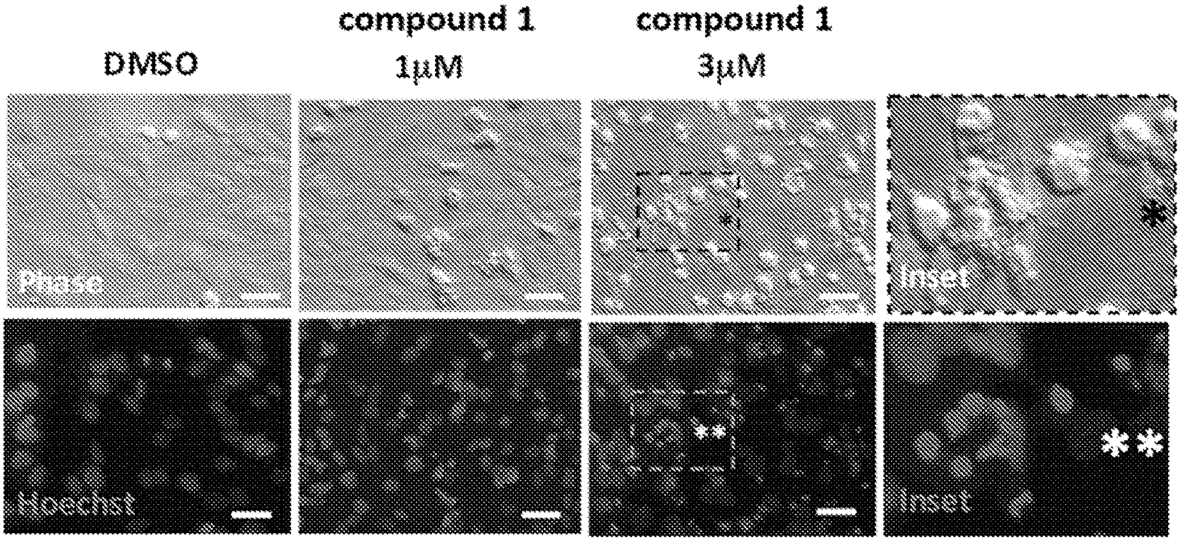
FIGS. 5A and 5B show bright phase micrographs and corresponding quantitation of nuclear fragmentation indicating minimal cytopathology with DMSO exposure in contrast to compound 1 treatments especially with 3 μM compound 1 where numerous cells round up and bleb (insets with black and white asterisks). Nuclear fragmentation, as detected by cytochemical analysis using Hoechst 33258 stain, in round up HeLa cells is dramatically increased by compound 1 treatment (inset with two white asterisks) but not in DMSO. Data, percentage of nuclear fragmented cells relative to total cells±SE (n=3). Scale bar is 20 μm.
Figure 5B:
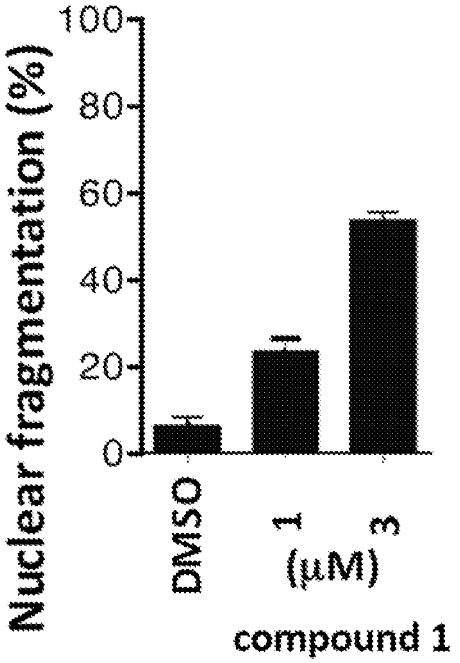
Figure 5C:
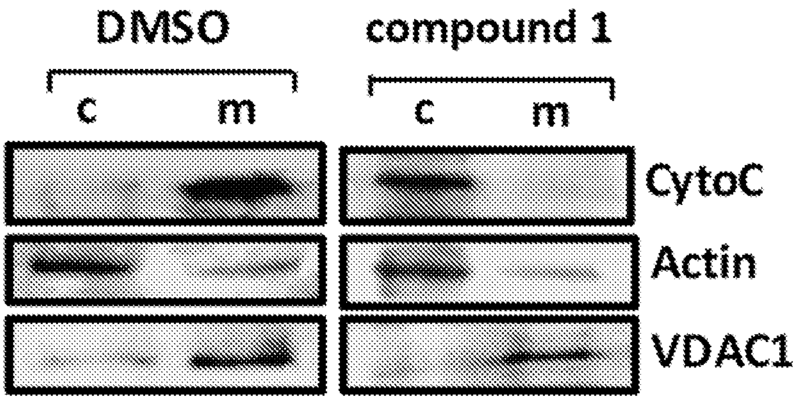
FIG. 5C shows illustrates cytochrome C release during treatment of HeLa cells with compound 1 as assessed by centrifugal separation of mitochondria followed by western blot analysis using cytochrome c specific antibody. Exposure of HeLa cells to 3 μM compound 1 triggers the release of cytochrome C from the mitochondria (m) to the cytosol (c). Actin and VDAC1 specific antibodies were used as controls to ensure the efficiency of cytoplasm and mitochondria fractionation respectively.
Figure 5D:
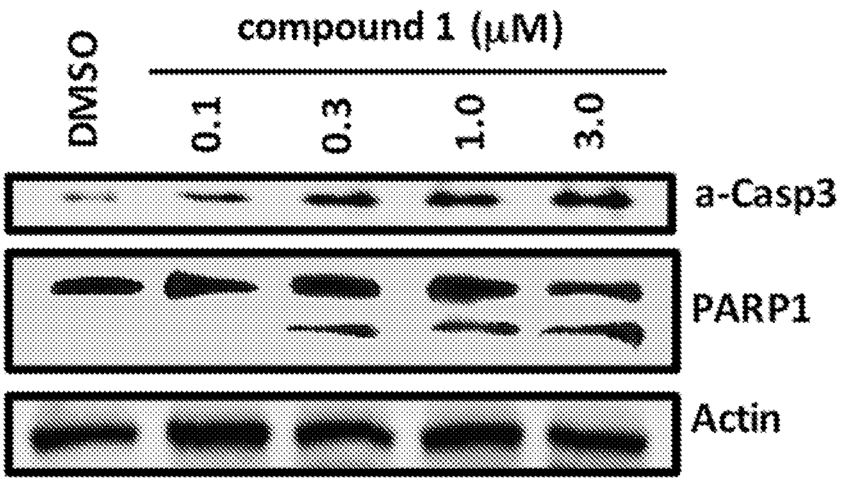
FIG. 5D shows western blot analysis of whole cell lysates for active caspase 3 (a-Casp3) and PARP1 during compound 1 treatment indicating a dose dependent increase in caspase 3 activation. Pronounced PARP1 cleavage by active caspase 3 is also observed with increasing concentrations of compound 1.
Figure 5E:
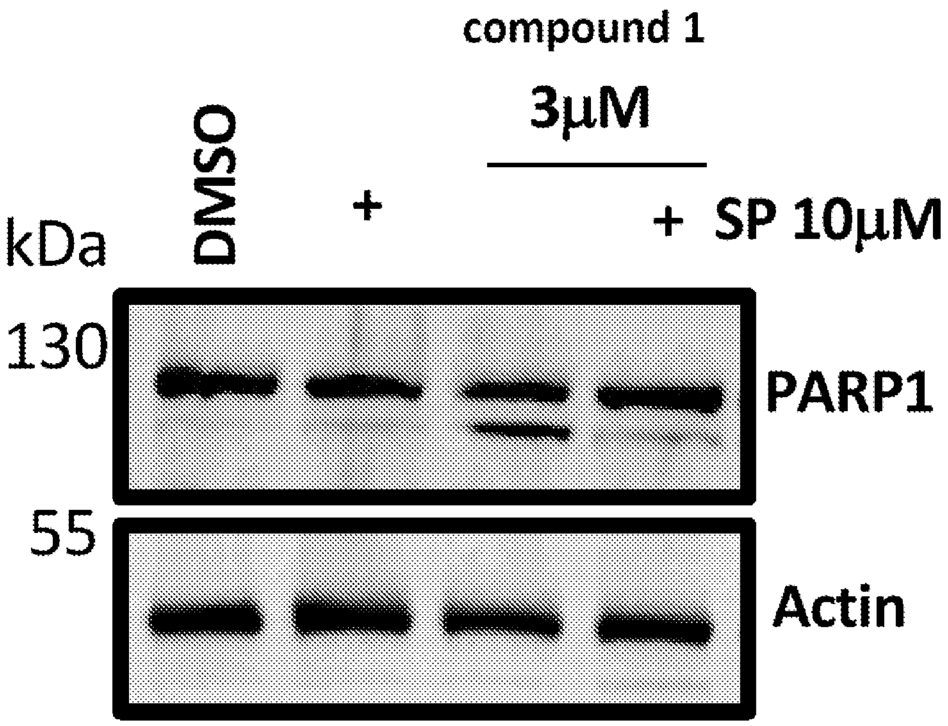
FIG. 5E shows degradation of XPB in cells by 10 μM sprinolactone dampens compound 1 induced apoptosis signaling as indicated by reduced PARP1 cleavage in whole cell lysates subjected to western blot analysis, actin was used as loading control.

Compound 1 induces Apoptosis of Cancer Cells via Activation of the Mitochondria-Mediated Apoptosis Pathway. Triptolide is known to induce apoptosis in a number of cancer cell lines. We investigated the cellular effects of compound 1 by examining the cellular morphology of HeLa cells upon exposure to compound 1. Compound 1 caused membrane blebbing and nuclear fragmentation indicative of apoptosis (FIGS. 5A and 5B). FIGS. 5A-5E show compound 1 induces apoptosis signaling. FIGS. 5A and 5B show that bright phase micrographs indicate minimal cytopathology with DMSO exposure in contrast to compound 1 treatments especially with 3 mM compound 1 where numerous cells round up and bleb (inset with black asterisk). Nuclear fragmentation, as detected by cytochemical analysis using Hoechst 33258 stain, in round up HeLa cells is dramatically increased by compound 1 treatment (inset with two white asterisks) but not in DMSO. Data are represented as percentage of nuclear fragmented cells relative to total cells GSE (n=3). The percentage of cells with nuclear fragmentation increased from 6% to 23% in the presence of 1 mM compound 1 and 53% upon treatment with 3 mM compound 1. Compound 1 induced the release of cytochrome c from the mitochondria into the cytosol, a key step in the activation of the intrinsic apoptotic pathway (FIG. 5C). FIG. 5C shows that cytochrome c release during compound 1 treatment assessed by centrifugal separation of mitochondria followed by western blot analysis using cytochrome-c-specific antibody. Exposure of HeLa cells to 3 mM compound 1 triggers the release of cytochrome c from the mitochondria (m) to the cytosol (c). Actin- and VDAC1-specific antibodies were used to ensure the efficiency of cytoplasm and mitochondria fractionation, respectively. As expected, compound 1 activated caspase-3 dose dependently, which was accompanied by cleavage of PARP1 (FIG. 5D). FIG. 5D shows western blot analysis of whole cell lysates for active caspase 3 (a-Casp3) and PARP1 during compound 1 treatment, which shows a dose-dependent increase in caspase 3 activation. Pronounced PARP1 cleavage by active caspase 3 is also observed with increasing concentrations of compound 1. Similar to RPB1 degradation, the cleavage of PARP1 requires XPB, as co-treatment with higher concentrations of SP prevented PARP1 cleavage by caspase-3 (FIG. 5E). FIG. 5E shows degradation of XPB in cells by 10 mM sprironolactone, which dampens compound 1-induced apoptosis signaling as indicated by reduced PARP1 cleavage in whole cell lysates subjected to western blot analysis. Actin was used as loading control. Scale bar, 20 mm. Together, these results suggest that compound 1 activated the mitochondria-mediated apoptotic pathway through induction of cytochrome c release and ensuing activation of caspase-3 in HeLa cells.

Figure 7A:
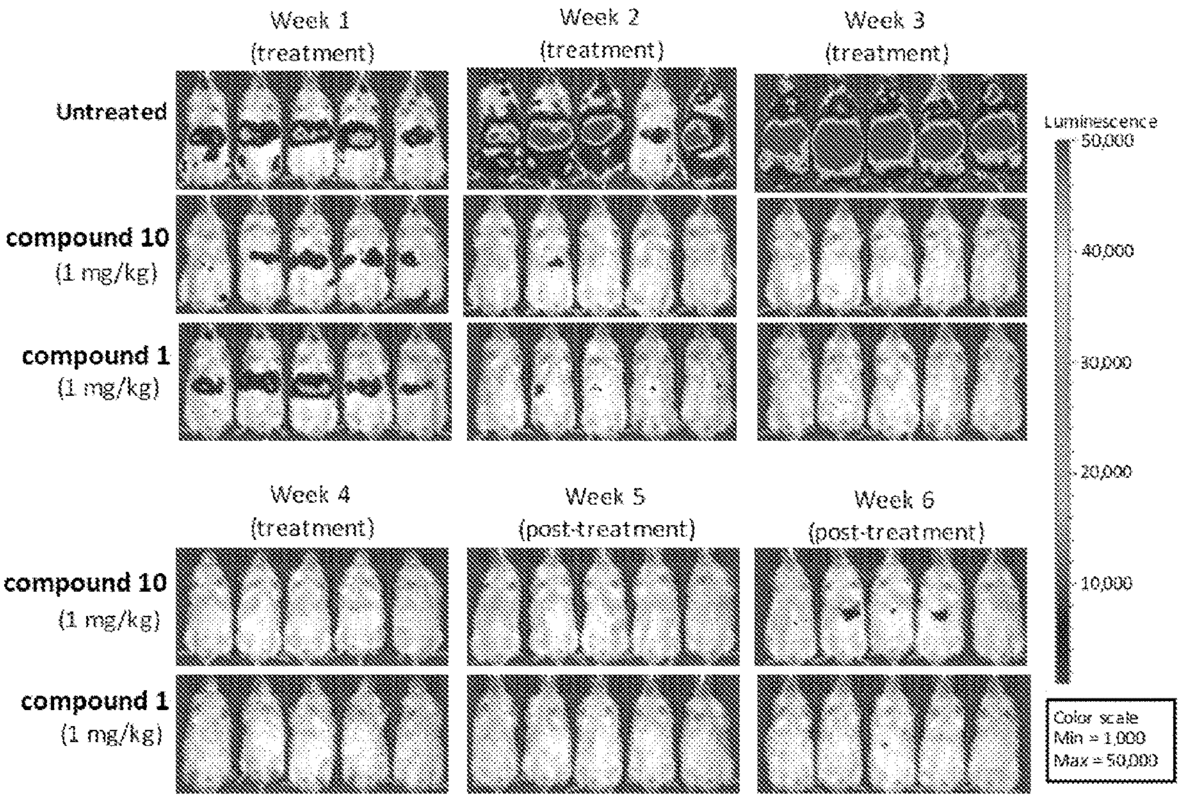
FIG. 7A shows compound 1 and compound 10 have similar Maximum Tolerable Dose (MTD) in a metastatic prostate cancer model. After confirmation of tumor growth in NOD/SCID/IL2$^{null}$ mice by bioluminescence imaging, daily administration of 1 mg/kg compound 10 or compound 1 for 30 days was tolerated by animals and able to suppress tumor growth throughout the treatment. Antitumor effect by compound 10 or compound 1 persists 2 weeks post-treatment.
Figure 7B:
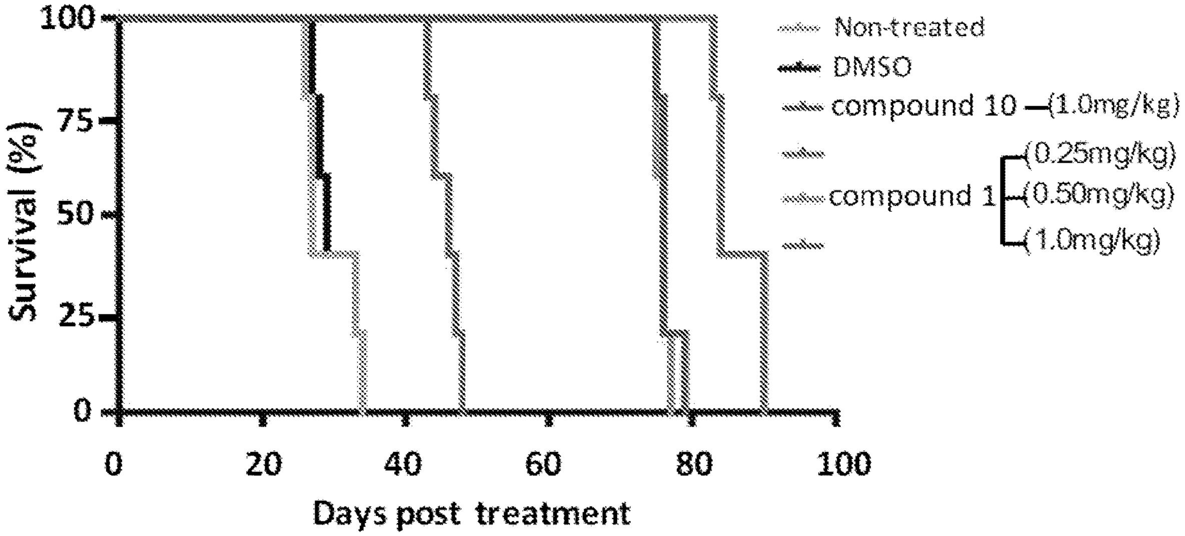
FIG. 7B shows Kaplan-Meier curves indicating survival time (days after initiation of treatments (n=5) for controls, compound 10, and compound 1 treatments. Median survival times (days) are as follows: non-treated=27, DMSO=29, compound 10 (1 mg/kg)=76, compound 1 (0.25 mg/kg)=46, compound 1 (0.5 mg/kg)=76, compound 1 (1 mg/kg)=84.
Figure 8A:
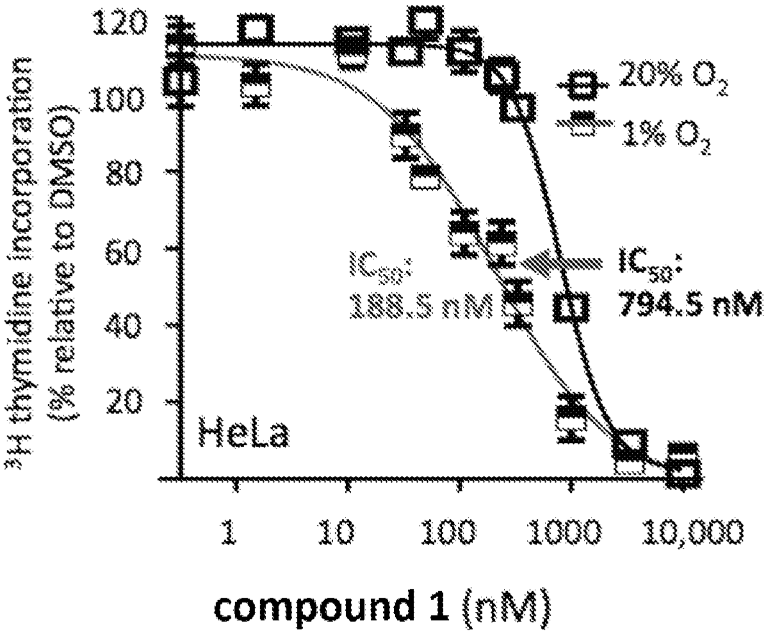
FIGS. 8A-8H show that hypoxia affects sensitivity of cancer cells to compound 1. Exposure of HeLa (A) and MDA MB231 cells (B) to a hypoxic environment (1% $O_2$) enhances the anti-proliferative effect of compound 1 at 48 h post treatment as measured by 3H thymidine incorporation in contrast to MCF-7 (E) or HepG2 (G) where modest enhancement or resistance is observed during hypoxia. Triptolide (TPL) shows modest anti-proliferative effect in all cells tested except HepG2 that showed resistance upon hypoxia. Proliferation was measured by 3H thymidine incorporation and plotted using GraphPad prism. Data represents mean±SEM relative to DMSO (n=3).
Figure 8B:
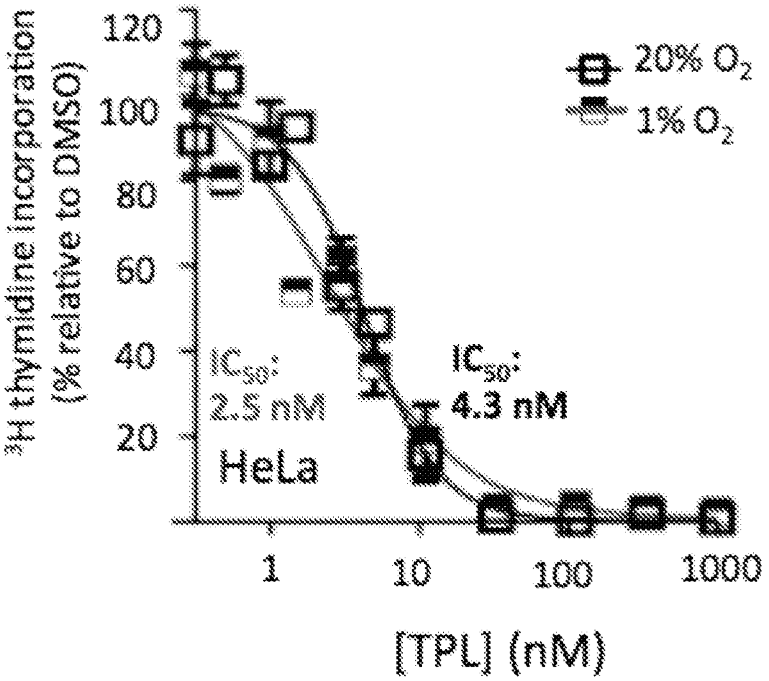
Figure 8C:
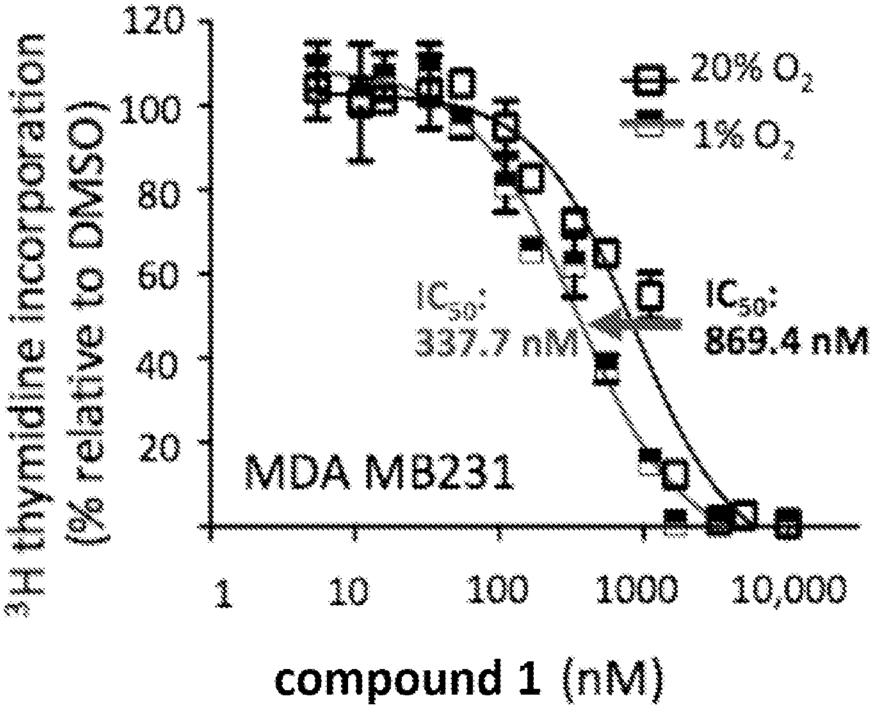
Figure 8D:
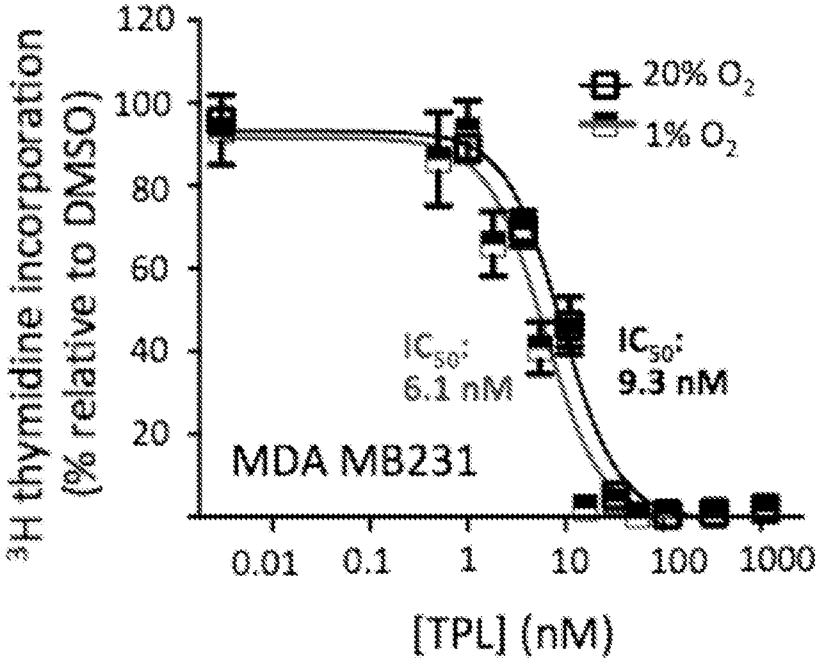
Figure 8E:
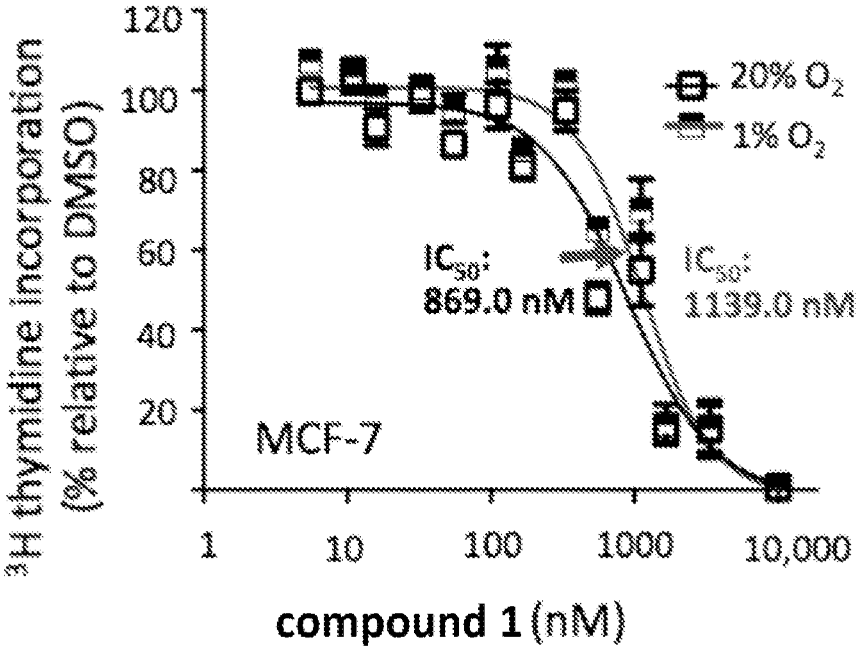
Figure 8F:
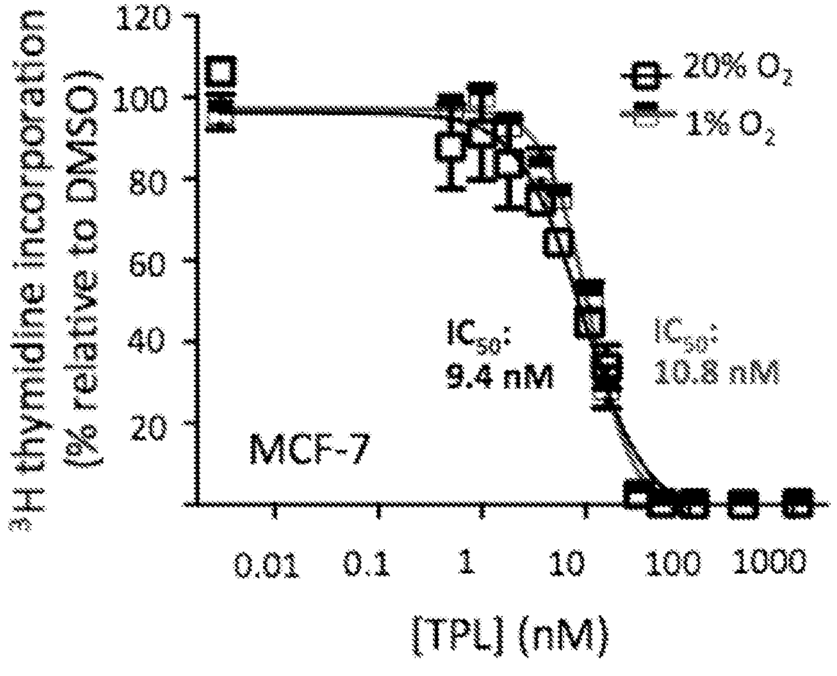
Figure 8G:
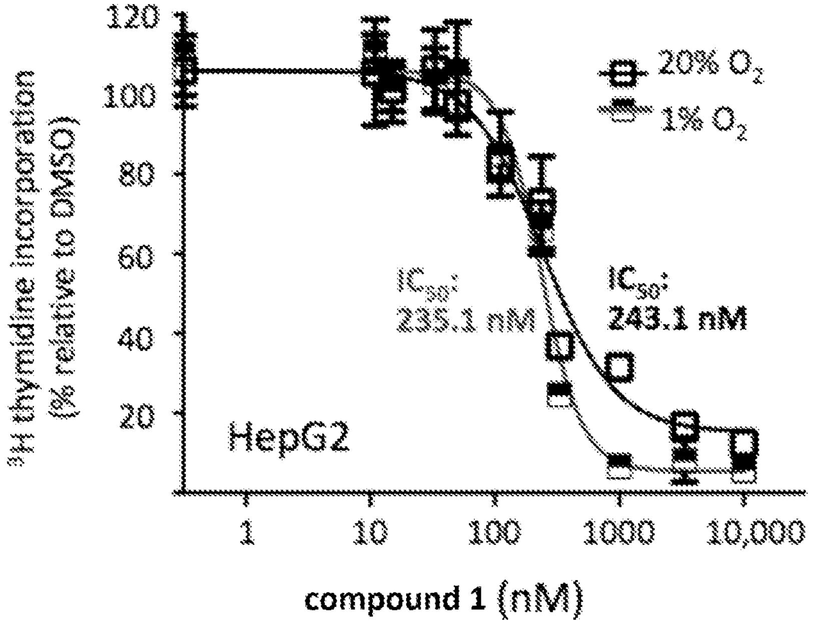
Figure 8H:
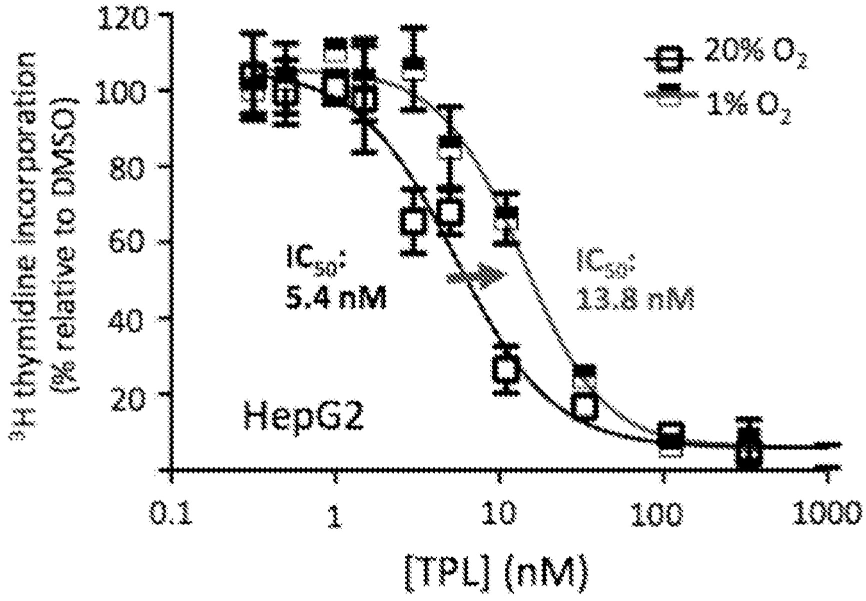

Compound 1 showed sustained inhibition of tumor growth and prolonged survival in vivo. We have previously shown that compound 10 exhibited sustained antitumor activity in vivo in an experimental metastatic prostate cancer mouse model. Using the same animal model, we assessed the antitumor efficacy of compound 1 side by side with compound 10. Thus, PC3 prostate cancer cells expressing firefly luciferase as a reporter were injected into animals through the tail vein. Three weeks after tumor cell injection, compounds 1 and 10 were administered by intraperitoneal injection once daily at various doses for a total of 30 days. The growth of tumor cells was monitored weekly through bioluminescence imaging. A rapid growth of tumor cells and metastasis to other organs occurred in untreated animals, killing all untreated animals by week 4 (FIG. 7A). FIGS. 7A-7B show that compound 1 improves survival in an in vivo prostate cancer model. FIG. 7A shows that compounds 1 and 10 have similar maximum tolerable dose (MTD) in a metastatic prostate cancer model. After confirmation of tumor growth in NOD/SCID/IL2rnull mice by bioluminescence imaging, daily administration of 1 mg/kg compound 10 or 1 for 30 days was tolerated by animals and able to suppress tumor growth throughout the treatment. Anti-tumor effect by compound 10 or 1 persists 2 weeks posttreatment. For animals dosed with 1 mg/kg compound 10, tumor cells were cleared by week 2 of treatment and did not return until two weeks after treatment was stopped (FIG. 7A). In contrast, animals receiving the same dose of compound 1 had undetectable levels of cancer cells two weeks after cessation of treatment, suggesting that compound 1 is more effective than compound 10 in vivo (FIG. 7A). Although compounds 1 and 10 were administered for only 30 days, they both significantly prolonged the survival of animals well beyond the four-week treatment window (FIG. 7B). FIG. 7B shows Kaplan-Meier curves showing survival time (days after initiation of treatments [n=5]) for controls, compound 10, or compound 1 treatments. Median survival times (days) are as follows: nontreated=27, DMSO=29, compound 10 (1 mg/kg)=76, compound 1 (0.25 mg/kg)=46, compound 1 (0.5 mg/kg)=76, compound 1 (1 mg/kg)=84. Moreover, the prolonged survival upon treatment with compound 1 was dose dependent with the longest survival achieved by the highest dose of compound 1 (26 days for untreated group versus 86 days for 1 mg/kg compound 1 treatment group). Furthermore, chi-square analysis shows that the survival curve for 1 mg/kg compound 10 is not significantly different from 0.5 mg/kg compound 1 (cannot reject null hypothesis at p=0.05). In contrast, the survival curve for compound 1 at 1 mg/kg is significantly different from compound 10 at the same dose (reject null hypothesis at p=0.001). Compound 1 given at 0.5 mg/kg led to the same overall survival as compound 10 at 1 mg/kg, consistent with the higher potency of compound 1 in tumor cell lines than compound 10 in vitro.

Figure 6A:
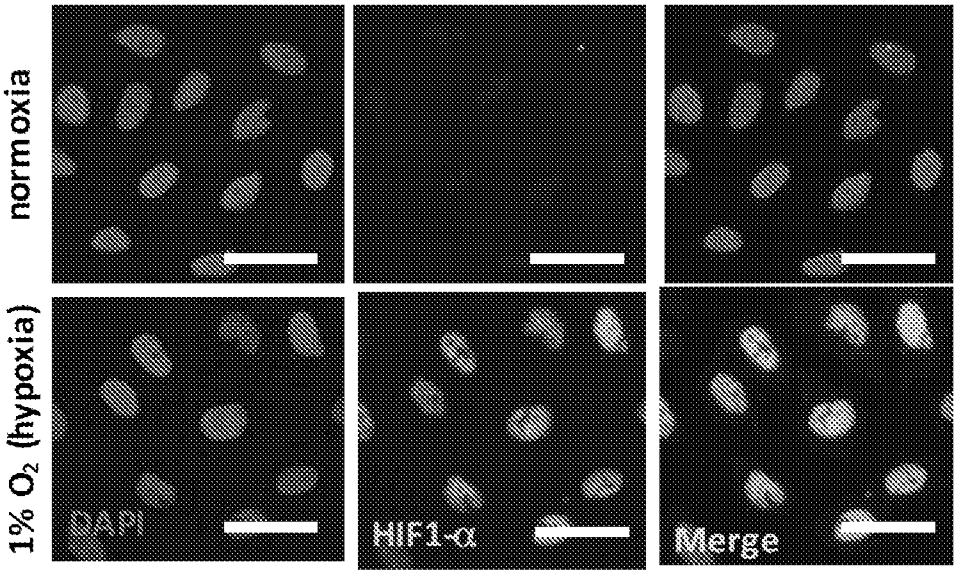
FIG. 6A shows immunocytochemical analysis of fixed cells using antibodies specific to HIF-1α, which indicates exposure to hypoxia (1% $O_2$) for 24 h stabilizes endogenous HIF-1α compared to normoxia (20% $O_2$) in PC3 cells, scale bar is 20 μm.
Figure 6B:
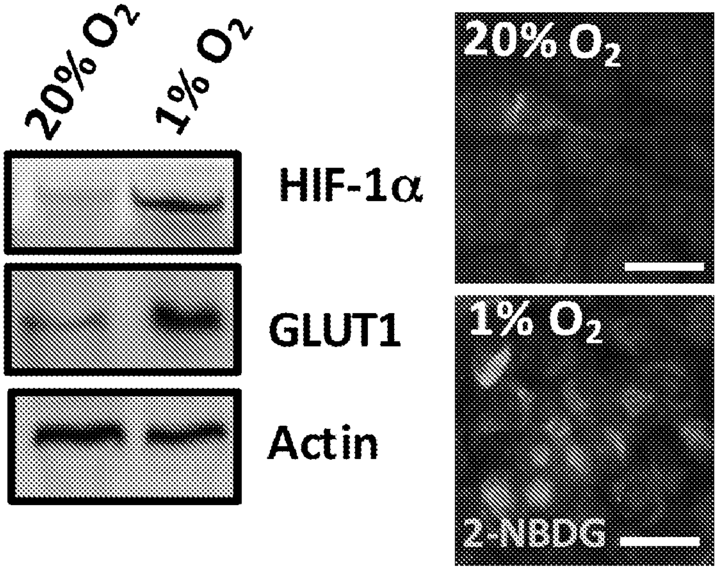
FIG. 6B shows western blot analysis of whole cell lysates for endogenous HIF-1α, GLUT1, and Actin (control) indicting increased HIF-1α and increased GLUT1 level and activity (i.e. 2-NBDG uptake) during hypoxia relative to normoxia, scale bar is 20 μm.
Figure 6C:
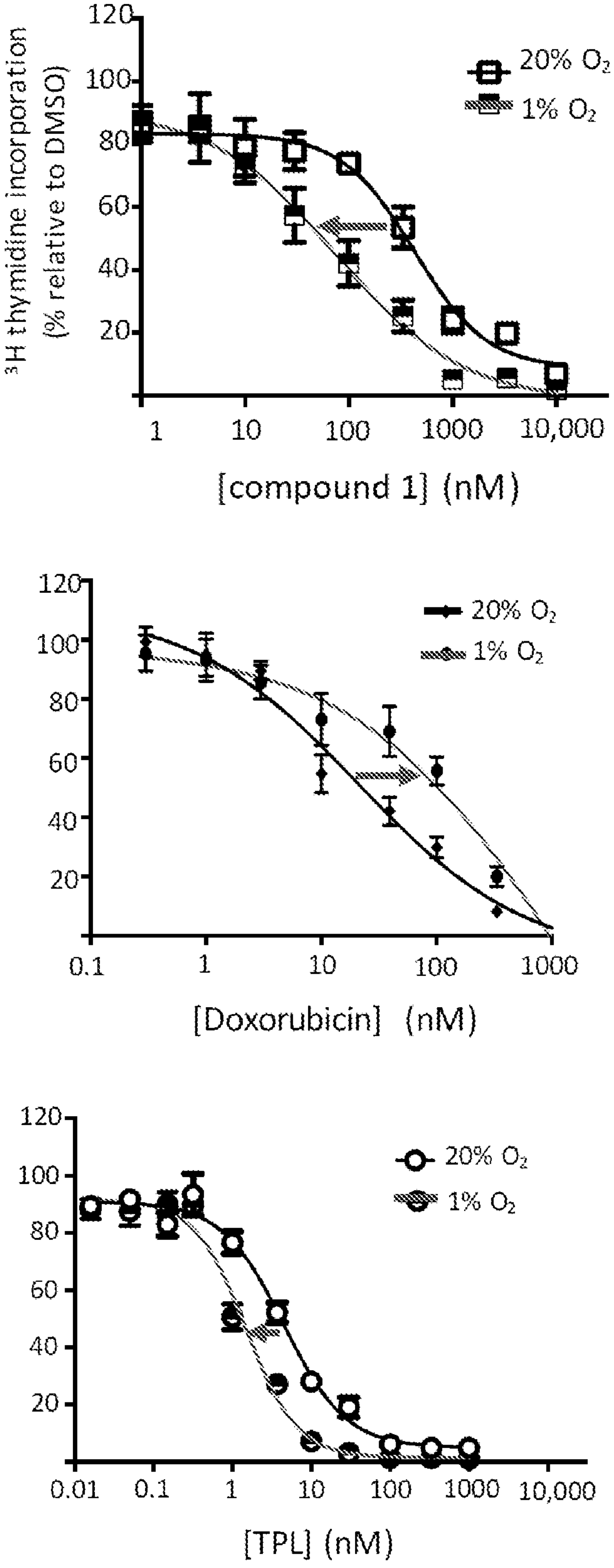
FIG. 6C shows hypoxia enhances the anti-proliferative effect of compound 1 at 48 h post treatment as measured by $^3H$ thymidine incorporation while co-treatment with doxorubicin and hypoxia reduces drug potency, TPL shows a modestly enhanced anti-proliferative effect in the presence of hypoxia. Data, mean±SE relative to DMSO (n=3)

Compound 1 is more effective against cancer cells under hypoxic than normoxic conditions. The tumor microenvironment is hypoxic due to the lack of sufficient blood vessel density in rapidly growing tumors. As such, tumor cells upregulate the expression of HIF-1, which in turn drives the expression of a number of pro-survival and proangiogenic factors including multidrug resistance (MDR) pumps and GLUTs. The upregulation of MDR and GLUTs under hypoxia renders tumor cells resistant to chemotherapeutic drugs. Interestingly, the upregulation of glucose transporters under hypoxia should make cancer cells more susceptible to compound 1 due to the presence of the glucose moiety. To test this possibility, we determined the effect of hypoxia on the sensitivity of cancer cells to compound 1 using the prostate cancer cell line PC3 because increased HIF-1a has been shown in metastatic prostate biopsies. Thus, PC3 cells were cultured under either hypoxic (1% $O_2$) or normoxic (20% $O_2$) conditions. As expected, HIF-1a is absent under normoxic conditions but is dramatically induced under hypoxia (FIG. 6A). FIGS. 6A-6F show that hypoxia enhances anti-proliferative effect of compound 1. FIG. 6A shows immunocytochemical analysis of fixed cells using antibodies specific to HIF-1a show that exposure to hypoxia (1% O2) for 24 h stabilizes endogenous HIF-1a compared with normoxia (20% O2) in PC3 cells. Western blot analysis of endogenous HIF-1a revealed a similar increase in HIF-1a with a corresponding increase in GLUT1 levels (FIG. 6B). FIG. 6B shows western blot analysis of whole cell lysates for endogenous HIF-1a, which indicates an increase during hypoxia compared with normoxia, which also corresponds with an increase in glucose transporter 1 (GLUT1). Uptake of the chromogenic glucose analogue 2-NBDG also increased under hypoxia. Importantly, PC3 cells became more sensitive to compound 1 under hypoxic conditions with a reduced IC50 of 81 nM from an IC50 of 427 nM under normoxic conditions (FIG. 6C), whereas the IC50 for triptolide was modestly reduced from 4.5 nM to 1.5 nM upon switching from normoxia to hypoxia. FIG. 6C shows hypoxia enhances the antiproliferative effect of compound 1 at 48 h posttreatment as measured by 3H thymidine incorporation, whereas co-treatment with doxorubicin and hypoxia reduces drug potency. Triptolide (TPL) shows a modest antiproliferative effect. Data are represented as mean G SE relative to DMSO (n=3). The same trend of enhanced susceptibility to compound 1 under hypoxia was also observed with HeLa and MDA MB231 (FIGS. 8A-8H).

FIGS. 8A-8H show hypoxia affects sensitivity of cancer cells to compound 1. Exposure of HeLa (FIG. 8A) and MDA MB231 cells (FIG. 8B) to a hypoxic environment enhances the anti-proliferative effect of compound 1 at 48 h post treatment as measured by 3H thymidine incorporation in contrast to MCF-7 (FIG. 8E) or HepG2 (FIG. 8G) where modest enhancement or resistance is observed during hypoxia. Triptolide (TPL) shows modest anti-proliferative effect in all cells tested except HepG2 that showed resistance upon hypoxia. Proliferation was measured by 3H thymidine incorporation and plotted using GraphPad prism. Data represents mean±SEM relative to DMSO (n=3).

Figure 6D:
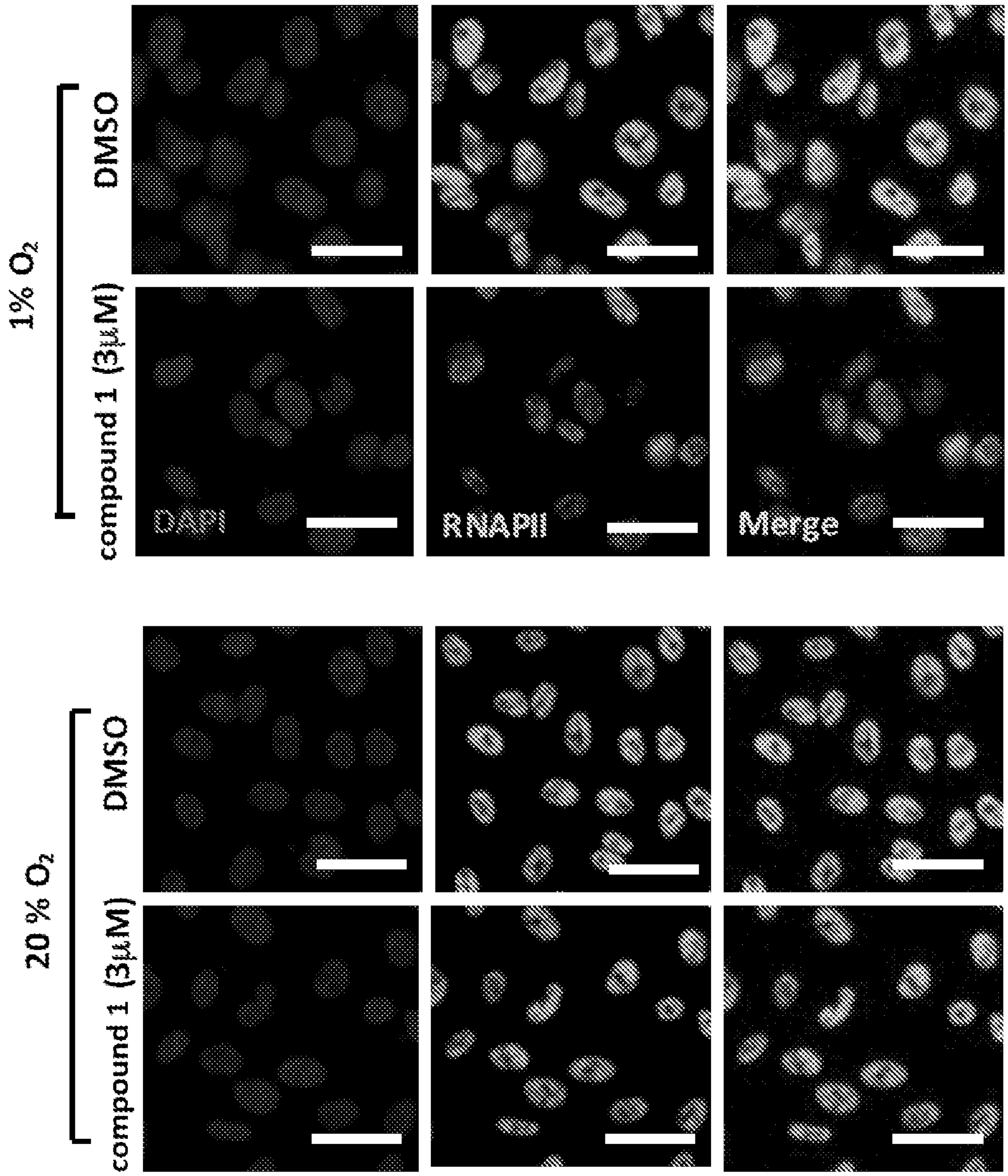
FIG. 6D shows immunocytochemistry using antibody specific to Rpb1, which indicates exposure of cells to hypoxia triggers an early onset of RNAPII subunit Rpb1 degradation by 3 μM compound 1 after 6 h, scale bar is 20 μm.
Figure 6E:
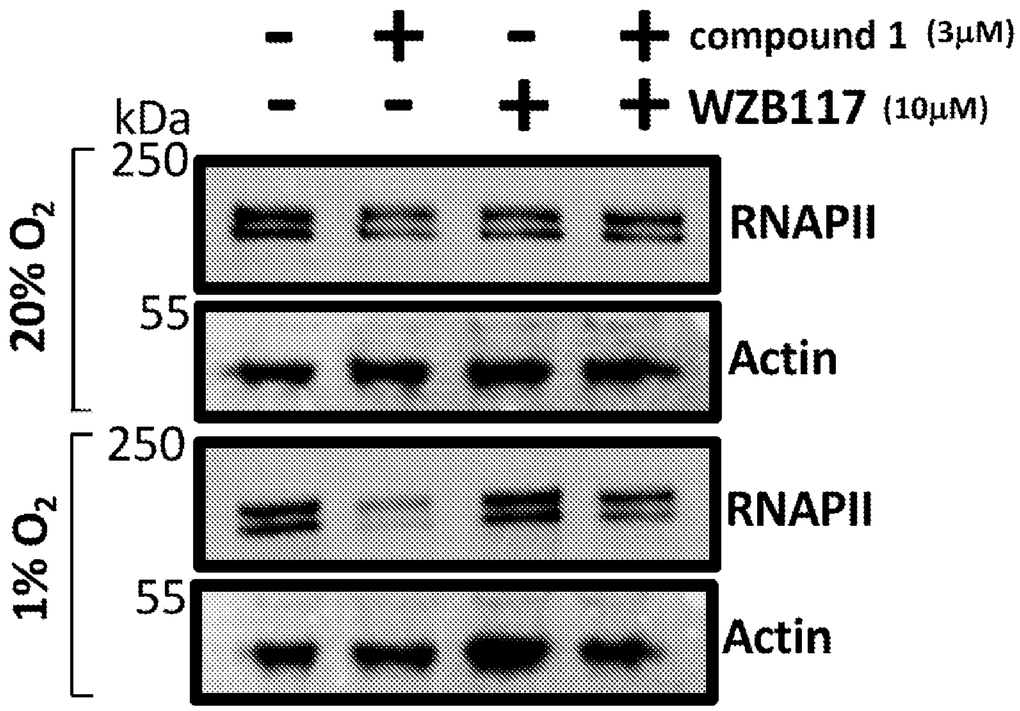
FIG. 6E shows whole cell lysates subjected to western blot using anti-Rpb1 specific antibody, under hypoxic and normoxic conditions illustrating that 10 μM glucose transporter 1 inhibitor WZB117 antagonizes the early onset of RNAPII degradation triggered by 3 μM compound 1 under hypoxic conditions.
Figure 6F:
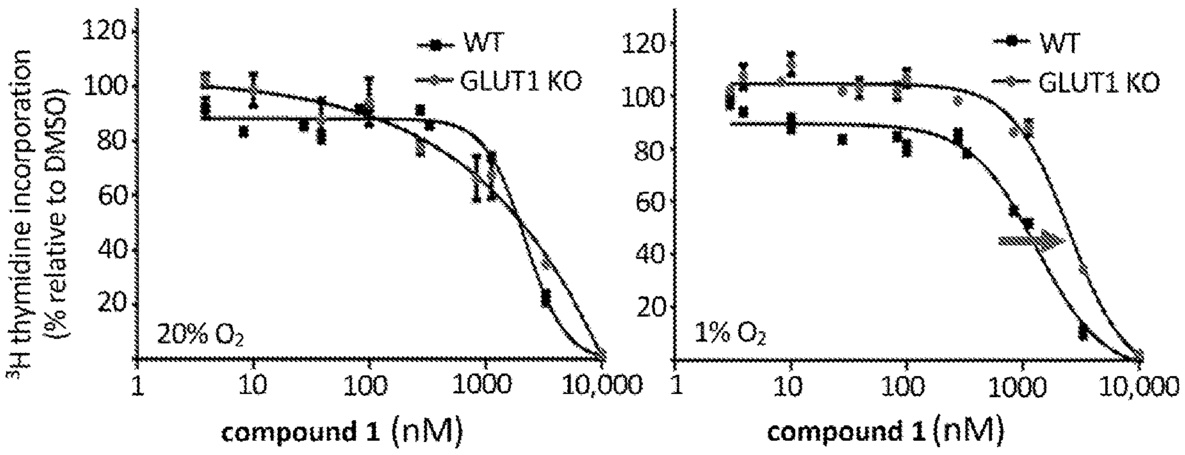
FIG. 6F shows DLD-1 WT cells exposed to hypoxia (1% $O_2$) exhibited enhanced sensitivity to compound 1 in comparison to DLD-1 GLUT1 knockout (GLUT1 KO) cells. No difference in sensitivity is observed between DLD-1 WT and GLUT1 KO under normoxia (20% $O_2$). Data are represented as mean±SEM relative to DMSO (n=3). Scale bar is 20 μm.

In contrast to compound 1, the potency of doxorubicin was decreased under hypoxia (FIG. 6C). Degradation of RNAPII, an indicator of inhibition of XPB by triptolide (FIGS. 4A-4F), was observed as early as 6 h after treatment with compound 1 under hypoxic but not in normoxic conditions (FIG. 6D) where compound 1 induced degradation of RPB1 also occurs in an XPB-dependent manner (FIGS. 4A-4F). FIG. 6D shows immunocytochemistry using antibody specific to RPB1, which indicates that exposure of cells to hypoxia triggers an early onset of RNAPII subunit RPB1 degradation by 3 mM compound 1 after 6 h. To verify whether this difference in sensitivity was due to the upregulation of GLUT1 levels and function under hypoxic conditions (FIG. 6B), we utilized the GLUT1 inhibitor WZB117. The addition of the GLUT inhibitor WZB117 abolished the rapid degradation of endogenous RNAPII in PC3 cells by compound 1 under hypoxic (1% O2) conditions (FIG. 6E), indicating that GLUT1 upregulation during hypoxia contributes to the rapid degradation of endogenous RNAPII by compound 1 under hypoxic conditions. FIG. 6E shows whole cell lysates subjected to western blot using anti-RPB1-specific antibody, which shows that 10 mM glucose transporter 1 inhibitor WZB117 antagonizes the early onset of RNAPII degradation triggered by 3 mM compound 1 and hypoxia. To further assess the role of GLUT1 upregulation in hypoxia-induced sensitization to compound 1, we examined the effects of compound 1 on the proliferation of both WTDLD-1 and its isogenic GLUT1 knockout cell line under normoxic (20% oxygen) and hypoxic (1% oxygen) conditions. The WT DLD-1 cells are more sensitive to compound 1 (IC50: 1.3 mM) than the GLUT1 knockout cell line under hypoxic conditions (IC50: 2.5 mM), indicating GLUT1 dependence of hypoxia-induced sensitization to compound 1 (FIG. 6F). In contrast, no difference in sensitivity was observed between DLD-1WT and GLUT1 KO under normoxia. FIG. 6F shows DLD-1 WT cells exposed to hypoxia exhibited enhanced sensitivity to compound 1 in comparison to DLD-1 GLUT1 knockout (GLUT1 KO) cells. No difference in sensitivity is observed between DLD-1 WT and GLUT1 KO under normoxia. Data are represented as mean G SEM relative to DMSO (n=3). Scale bar, 20 mm. Together, these results reveal that in contrast to most existing anticancer agents, compound 1 is more effective against tumor cells under hypoxia, making it a unique anticancer agent with potentially enhanced antitumor activity in vivo.

Most cytotoxic anticancer drugs, including those that are currently used in the clinic such as taxol, doxorubicin, and cyclophosphamide exert their antiproliferative and proapoptotic effects on cancer cells by blocking essential cellular protein targets that are shared with normal cells. As such, it is not surprising that those chemotherapeutic agents have severe adverse effects on patients. Transcription mediated by RNAPII is essential for mammalian cell proliferation and growth. As such, it is not surprising that cancer cells are susceptible to triptolide that blocks RNAPII-mediated mRNA synthesis through covalent modification of XPB/TFIIH accompanied by induced degradation of RPB1 catalytic subunit of RNAPII in an XPB-dependent manner (FIG. 4F). The toxicity of triptolide can also be attributed to the same mechanism given the essential role of RNAPII-mediated transcription in normal cells, making it difficult to reduce the toxicity of triptolide without compromising its antitumor efficacy given the shared molecular mechanism. By conjugating triptolide to glucose, selectivity toward cancer cells was achieved by taking advantage of the higher levels of glucose transporters expressed in fast-growing tumor cells than most normal tissues. In the present study, we have identified a second-generation glutriptolide analog, compound 1, that met our expectations with significantly enhanced selectivity for tumor cells over normal cells, improved serum stability, and sustained antitumor activity in a PC-3 tumor model. Importantly, in the course of characterizing compound 1, we found that compound 1 gained antitumor potency under hypoxia in contrast to conventional cytotoxic drugs in vitro, pointing to an emerging strategy of overcoming drug resistance during cancer treatment.

The best lead of the second-generation glutriptolide called compound 1 is superior to the first-generation compound 10 in a number of ways. First, degradation of compound 10 by plasma esterases produces a highly toxic intermediate that was previously proven lethal to two of twenty subjects in a phase 1 clinical trial. Although the mechanistic basis of the toxicity for the compound 10 intermediate is still unknown, our data from a limited number of primary human cells indicate a significantly lower toxicity for compound 1 in comparison with compound 10 in noncancerous cells (FIG. 3D). The reported toxicity for the compound 10 intermediate occurred in two patients receiving the highest dose of therapy, suggesting dose-limiting toxicity. Maximum serum levels of F60008 and triptolide from the lethal case dosed with 18 mg/m2 were 1,361 ng/mL (~2.96 mM) and 58.5 ng/mL (~0.16 mM), respectively. Our cell-based viability assays with primary human cells show IC50 values for compound 10 ranging from 1.37 to 5.6 mM (FIG. 3D and Table 2), which includes the above-reported plasma concentration of F60008 in the lethal case with 18 $mg/m^2$ F60008. We have also shown previously using a smaller panel of primary human cells that the IC50 of triptolide ranges from 0.0042 to 0.0235 mM, which is 7- to 38-fold lower than the maximum serum concentration of triptolide from the lethal case. In summary, the toxicities observed with compound 10 intermediate F60008 are in part dose dependent as no lethality was observed in 18 of the 20 patients administered with <12 $mg/m^2$ F60008. By replacing the ester linkage to glucose with a glycosidic bond, the potential intermediate will be an alcohol that is expected to have less toxicity. More importantly, given the much greater stability of compound 1 in human serum than compound 10, the amount of this alcohol degradation intermediate is expected to be significantly reduced, further reducing the potential toxicity of compound 1 (FIG. 3A). Second, compound 1 exhibited greater stability in human serum than compound 10 (FIG. 3A). This is likely attributable to the glycosidic linkage between the linker and glucose moieties that requires a different type of hydrolytic enzyme(s) than the corresponding ester bond in compound 10. The increase in serum stability makes compound 1 a potentially better lead for drug development as it is a prodrug, and premature degradation in serum would release free triptolide that can exert toxicity to normal tissues. Third, compound 1 showed lower cytotoxicity to normal cells than to a subset of cancer cells (FIG. 3C). It is interesting to note that different types of cancer lines exhibited distinct sensitivity. Among the limited cancer cell lines tested, it appears that prostate, breast, and head and neck cancers are particularly sensitive to compound 1. In contrast, melanoma, pancreatic, lung, and liver cancer lines appear to be less sensitive to compound 1 with an average IC50 values comparable or even higher than normal cells. Extensive profiling of a large number of cancer cell lines and collections of cultured patient-derived tumor cells will be needed to comprehensively determine whether the selective toxicity of compound 1 to certain types of cancer such as those of the prostate holds true.

Aside from its unique anticancer activity in vitro, compound 1 also exhibited sustained antitumor activity in a PC3 xenograft model in vivo (FIGS. 7A-7B). Cancer cells failed to re-emerge two weeks after treatment with compound 1 ceased but not with compound 10. The slower reappearance of cancer cells after treatment with compound 1 than compound 10 is also consistent with longer survival in compound 1-treated animals. Compound 1 at 0.5 mg/kg was as effective as compound 10 at 1 mg/kg in prolonging the survival of xenograft model animals in vivo. The greater serum stability, the lower cytotoxicity toward normal cells compared with a subset of cancer cells, and the increased efficacy toward cancer cells under hypoxia along with sustained antitumor activity of compound 1 in vivo render this glutriptolide analogue an interesting example of a promising lead candidate for further development as a type of anticancer drug targeting transcription.

The microenvironment of solid tumors is known to be hypoxic, and hypoxia has been shown to confer resistance in tumor cells against cytotoxic anticancer drugs, which is a major hurdle for cancer therapy. As hypoxia is known to upregulate GLUT expression on the cancer cell surface and given that GLUTs confer the tumor cell selectivity of glutriptolides, we investigated the effect of hypoxia on the potency of compound 1. The increase in potency of compound 1 for inhibition of cancer cell proliferation during hypoxia contrasts the decrease in potency of the broadly used, FDA-approved, anticancer drug doxorubicin (FIGS. 6C and 8A-8H). This feature of compound 1 as an anticancer drug candidate offers an additional advantage of being more effective toward cancer cells under hypoxia where other conventional anticancer drugs encounter resistance. It is also interesting to note that unlike doxorubicin, triptolide itself also showed a modest enhancement, rather than reduction, in its inhibitory effect on cancer cell growth under hypoxic conditions. This may be attributed in part to its inhibition of the transcriptional activity of HIF-1 that requires TFIIH and RNAPII. Because hypoxia involves the transcription of genes to adapt the survival of cancer cells to a hypoxic condition, the ability of triptolide to inhibit mammalian transcription initiation can dampen HIF-driven transcription of hypoxia-activated genes that facilitate the proliferation of cancer cells experiencing hypoxia. Treatment of cancer cells under hypoxia with triptolide inhibits the transcription of HIF-1a target genes VEGF, BNIP3, and CAIX, including a hypoxia responsive element (HRE)-driven luciferase reporter. Triptolide treatment also reverses hypoxia-induced epithelial-mesenchymal transition explaining the observed three-fold enhancement of triptolide's anti-proliferative effect in vitro (FIG. 6C). The increased expression of GLUTs in cancer cells during hypoxia further amplifies the impact of transcription inhibition by compound 1 on the proliferation of hypoxic cancer cells as seen with the five-fold increase in compound 1 IC50 during hypoxia (FIG. 6C). The conjugation of triptolide to glucose in compound 1 enhances the effect size of triptolide during hypoxia from 0.71 during triptolide treatment alone to 64.89 in compound 1-treated hypoxic PC3 cells. The GLUT1 dependence of enhanced compound 1-induced anti-proliferation in hypoxic cancer cells is demonstrated in the reduced sensitivity of hypoxic DLD-1 GLUT1 knock out cells compared with parental DLD-1 cells (FIG. 6F). Although the enhanced sensitivity to glucose-conjugated triptolide compound 1 under hypoxia was also observed in HeLa and triple-negative breast cancer cell line MDA MB231 (FIGS. 8A-8H), this effect is not observed in all the cell lines tested, as the liver cancer cell line HepG2 remains resistant to compound 1 under hypoxia. Despite the apparent tissue-specific sensitivity of cancer cells to compound 1, our results suggest that conjugation of potent, nonspecific antiproliferative agents to glucose offers a promising strategy for targeting cancer cells in hypoxic conditions such as those in solid tumors. This finding offers an alternative albeit viable strategy to combat hypoxia-induced drug resistance in solid tumors through conjugation of cytotoxic drugs to glucose.

To summarize, triptolide is a key ingredient from a traditional Chinese medicinal plant that has been used for centuries. It possesses potent antitumor activity through irreversible inhibition of the XPB subunit of the general transcription factor TFIIH, effectively blocking transcription initiation. Its potential development as an anticancer drug has been limited by its toxicity and insolubility in water. In an attempt to address these issues, we have designed and synthesized glucose conjugates of triptolide exhibiting lower toxicity and sustained antitumor activity in vivo. However, the previous lead glutriptolide releases a potentially toxic degradation intermediate, rendering it unsuitable as a drug candidate. By using molecular linkers that connect triptolide to glucose, we identified a glutriptolide with enhanced stability in serum and reduced toxicity to normal cells. Importantly, glutriptolide compound is more potent against cancer cells under hypoxic conditions likely due to the upregulation of glucose transporters, in contrast to most cytotoxic anticancer drugs to which cancer cells gain resistance under hypoxia. Compound 1 showed sustained antitumor activity in vivo and significantly prolonged survival of treated animals. These findings suggest that conjugation of cytotoxic drugs to glucose may be a viable strategy to overcome drug resistance in general and that compound is a promising candidate for further development as a targeted, anticancer pro-drug.

The term "treatment" is used interchangeably herein with the term "therapeutic method" and refers to both 1) therapeutic treatments or measures that cure, slow down, lessen symptoms of, and/or halt progression of a diagnosed pathologic conditions, disease or disorder, and 2) and prophylactic/preventative measures. Those in need of treatment may include individuals already having a particular medical disease or disorder as well as those who may ultimately acquire the disorder (i.e., those needing preventive measures).

The term "subject" as used herein refers to any individual or patient to which the subject methods are performed. Generally, the subject is human, although as will be appreciated by those in the art, the subject may be an animal.

Also disclosed herein are pharmaceutical compositions including compounds with the structures of Formula (I), Formula (II), Formula (III), or compound 1. The term "pharmaceutically acceptable carrier" refers to a non-toxic carrier that may be administered to a patient, together with a compound of this disclosure, and which does not destroy the pharmacological activity thereof. Pharmaceutically acceptable carriers that may be used in these compositions include, but are not limited to, ion exchangers, alumina, aluminum stearate, lecithin, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In pharmaceutical composition comprising only the compounds described herein as the active component, methods for administering these compositions may additionally comprise the step of administering to the subject an additional agent or therapy. Such therapies include, but are not limited to, an anemia therapy, a diabetes therapy, a hypertension therapy, a cholesterol therapy, neuropharmacologic drugs, drugs modulating cardiovascular function, drugs modulating inflammation, immune function, production of blood cells; hormones and antagonists, drugs affecting gastrointestinal function, chemotherapeutics of microbial diseases, and/or chemotherapeutics of neoplastic disease. Other pharmacological therapies can include any other drug or biologic found in any drug class. For example, other drug classes can comprise allergy/cold/ENT therapies, analgesics, anesthetics, anti-inflammatories, antimicrobials, antivirals, asthma/pulmonary therapies, cardiovascular therapies, dermatology therapies, endocrine/metabolic therapies, gastrointestinal therapies, cancer therapies, immunology therapies, neurologic therapies, ophthalmic therapies, psychiatric therapies or rheumatologic therapies. Other examples of agents or therapies that can be administered with the compounds described herein include a matrix metalloprotease inhibitor, a lipoxygenase inhibitor, a cytokine antagonist, an immunosuppressant, a cytokine, a growth factor, an immunomodulator, a prostaglandin or an anti-vascular hyperproliferation compound.

The term "therapeutically effective amount" as used herein refers to the amount of active compound or pharmaceutical agent that elicits the biological or medicinal response in a tissue, system, animal, individual or human that is being sought by a researcher, veterinarian, medical doctor or other clinician, which includes one or more of the following: (1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) Ameliorating the disease; for example, ameliorating a disease, condition or disorder in an individual that is experiencing or displaying the pathology or symptomatology of the disease, condition or disorder (i.e., reversing the pathology and/or symptomatology).

As used herein, the terms "combination," "combined," and related terms refer to the simultaneous or sequential administration of therapeutic agents in accordance with this disclosure. For example, a described compound may be administered with another therapeutic agent simultaneously or sequentially in separate unit dosage forms or together in a single unit dosage form. Accordingly, the present disclosure provides a single unit dosage form comprising a described compound, an additional therapeutic agent, and a pharmaceutically acceptable carrier, adjuvant, or vehicle. Two or more agents are typically considered to be administered "in combination" when a patient or individual is simultaneously exposed to both agents. In many embodiments, two or more agents are considered to be administered "in combination" when a patient or individual simultaneously shows therapeutically relevant levels of the agents in a particular target tissue or sample (e.g., in brain, in serum, etc.).

When the compounds of this disclosure are administered in combination therapies with other agents, they may be administered sequentially or concurrently to the patient. Alternatively, pharmaceutical or prophylactic compositions according to this disclosure comprise a combination of ivermectin, or any other compound described herein, and another therapeutic or prophylactic agent. Additional therapeutic agents that are normally administered to treat a particular disease or condition may be referred to as "agents appropriate for the disease, or condition, being treated."

The compounds utilized in the compositions and methods of this disclosure may also be modified by appending appropriate functionalities to enhance selective biological properties. Such modifications are known in the art and include those, which increase biological penetration into a given biological system (e.g., blood, lymphatic system, or central nervous system), increase oral availability, increase solubility to allow administration by injection, alter metabolism and/or alter rate of excretion.

According to a preferred embodiment, the compositions of this disclosure are formulated for pharmaceutical administration to a subject or patient, e.g., a mammal, preferably a human being. Such pharmaceutical compositions are used to ameliorate, treat or prevent any of the diseases described herein in a subject.

Agents of the disclosure are often administered as pharmaceutical compositions comprising an active therapeutic agent, i.e., and a variety of other pharmaceutically acceptable components. See Remington's Pharmaceutical Science (15th ed., Mack Publishing Company, Easton, Pa., 1980). The preferred form depends on the intended mode of administration and therapeutic application. The compositions can also include, depending on the formulation desired, pharmaceutically acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In some embodiments, the present disclosure provides pharmaceutically acceptable compositions comprising a therapeutically effective amount of one or more of a described compound, formulated together with one or more pharmaceutically acceptable carriers (additives) and/or diluents for use in treating the diseases described herein, including, but not limited to cancer. While it is possible for a described compound to be administered alone, it is preferable to administer a described compound as a pharmaceutical formulation (composition) as described herein. Described compounds may be formulated for administration in any convenient way for use in human or veterinary medicine, by analogy with other pharmaceuticals.

As described in detail, pharmaceutical compositions of the present disclosure may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations for use in accordance with the present disclosure include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient, which can be combined with a carrier material, to produce a single dosage form will vary depending upon the host being treated, and the particular mode of administration. The amount of active ingredient that can be combined with a carrier material to produce a single dosage form will generally be that amount of the compound, which produces a therapeutic effect. Generally, this amount will range from about 1% to about 99% of active ingredient. In some embodiments, this amount will range from about 5% to about 70%, from about 10% to about 50%, or from about 20% to about 40%.

In certain embodiments, a formulation as described herein comprises an excipient selected from the group consisting of cyclodextrins, liposomes, micelle forming agents, e.g., bile acids, and polymeric carriers, e.g., polyesters and polyanhydrides; and a compound of the present disclosure. In certain embodiments, an aforementioned formulation renders orally bioavailable a described compound of the present disclosure.

Methods of preparing formulations or compositions comprising described compounds include a step of bringing into association a compound of the present disclosure with the carrier and, optionally, one or more accessory ingredients. In general, formulations may be prepared by uniformly and intimately bringing into association a compound of the present disclosure with liquid carriers, or finely divided solid carriers, or both, and then, if necessary, shaping the product.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as those described in Pharmacopeia Helvetica, or a similar alcohol. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In some cases, in order to prolong the effect of a drug, it may be desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the described compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

The pharmaceutical compositions of this disclosure may be orally administered in any orally acceptable dosage form including, but not limited to, capsules, tablets, and aqueous suspensions and solutions. In the case of tablets for oral use, carriers, which are commonly used include lactose and corn starch. Lubricating agents, such as magnesium stearate, are also typically added. For oral administration in a capsule form, useful diluents include lactose and dried cornstarch. When aqueous suspensions and solutions and propylene glycol are administered orally, the active ingredient is combined with emulsifying and suspending agents. If desired, certain sweetening and/or flavoring and/or coloring agents may be added.

Formulations described herein suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. Compounds described herein may also be administered as a bolus, electuary or paste.

In solid dosage forms for oral administration (capsules, tablets, pills, dragees, powders, granules and the like), an active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and nonionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

Tablets may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent. If a solid carrier is used, the preparation can be in tablet form, placed in a hard gelatin capsule in powder or pellet form, or in the form of a troche or lozenge. The amount of solid carrier will vary, e.g., from about 25 to 800 mg, preferably about 25 mg to 400 mg. When a liquid carrier is used, the preparation can be, e.g., in the form of a syrup, emulsion, soft gelatin capsule, sterile injectable liquid such as an ampule or nonaqueous liquid suspension. Where the composition is in the form of a capsule, any routine encapsulation is suitable, for example, using the aforementioned carriers in a hard gelatin capsule shell.

Tablets and other solid dosage forms, such as dragees, capsules, pills and granules, may optionally be scored or prepared with coatings and shells, such as enteric coatings and other coatings well known in the pharmaceutical-formulating art. They may alternatively or additionally be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of compounds of the disclosure include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, oral compositions can also include adjuvants such as wetting agents, emulsifying and suspending agents, sweetening, flavoring, coloring, perfuming and preservative agents.

Suspensions, in addition to active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The pharmaceutical compositions of this disclosure may also be administered in the form of suppositories for rectal administration. These compositions can be prepared by mixing a compound of this disclosure with a suitable non-irritating excipient, which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this disclosure is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this disclosure include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this disclosure may also be topically applied to the lower intestinal tract by rectal suppository formulation or in a suitable enema formulation. Topically-administered transdermal patches are also included in this disclosure.

The pharmaceutical compositions of this disclosure may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

Transdermal patches have the added advantage of providing controlled delivery of a compound of the present disclosure to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Examples of suitable aqueous and nonaqueous carriers, which may be employed in the pharmaceutical compositions of the disclosure, include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Such compositions may also contain adjuvants such as preservatives, wetting agents, emulsifying agents and dispersing agents. Inclusion of one or more antibacterial and/or antifungal agents, for example, paraben, chlorobutanol, phenol sorbic acid, and the like, may be desirable in certain embodiments. It may alternatively or additionally be desirable to include isotonic agents, such as sugars, sodium chloride, and the like into the compositions. In addition, prolonged absorption of the injectable pharmaceutical form may be brought about by the inclusion of agents, which delay absorption such as aluminum monostearate and gelatin.

In certain embodiments, a described compound or pharmaceutical preparation is administered orally. In other embodiments, a described compound or pharmaceutical preparation is administered intravenously. Alternative routes of administration include sublingual, intramuscular, and transdermal administrations.

When compounds described herein are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

Preparations described herein may be given orally, parenterally, topically, or rectally. They are of course given in forms suitable for the relevant administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

Such compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, compounds described herein which may be used in a suitable hydrated form, and/or the pharmaceutical compositions of the present disclosure, are formulated into pharmaceutically-acceptable dosage forms by conventional methods known to those of skill in the art.

Actual dosage levels of the active ingredients in the pharmaceutical compositions of the disclosure may be varied so as to obtain an amount of the active ingredient that is effective to achieve the desired therapeutic response for a particular patient, composition, and mode of administration, without being toxic to the patient.

The terms “administration of” and or “administering” should be understood to mean providing a pharmaceutical composition in a therapeutically effective amount to the subject in need of treatment. Administration routes can be enteral, topical or parenteral. As such, administration routes include but are not limited to intracutaneous, subcutaneous, intravenous, intraperitoneal, intraarterial, intrathecal, intracapsular, intraorbital, intracardiac, intradermal, transdermal, transtracheal, subcuticular, intraarticulare, subcapsular, subarachnoid, intraspinal and intrasternal, oral, sublingual buccal, rectal, vaginal, nasal ocular administrations, as well infusion, inhalation, and nebulization.

The term “cancer” refers to a group diseases characterized by abnormal and uncontrolled cell proliferation starting at one site (primary site) with the potential to invade and to spread to others sites (secondary sites, metastases) which differentiate cancer (malignant tumor) from benign tumor. Virtually all the organs can be affected, leading to more than 100 types of cancer that can affect humans. Cancers can result from many causes including genetic predisposition, viral infection, exposure to ionizing radiation, exposure environmental pollutant, tobacco and or alcohol use, obesity, poor diet, lack of physical activity or any combination thereof.

Exemplary cancers described by the national cancer institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood: Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma. Childhood Brain Stem; Glioma. Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS Related; Lymphoma, Central Nervous System (Primary); Lymphoma, Cutaneous T-Cell; Lymphoma, Hodgkin's, Adult; Lymphoma, Hodgkin's; Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplasia Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood', Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland'Cancer, Childhood; Sarcoma, Ewing's Family of Tumors; Sarcoma, Kaposi's; Sarcoma (OsteosarcomaVMalignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor.

In certain aspects, cancer include Lung cancer, Breast cancer, Colorectal cancer, Prostate cancer, Stomach cancer, Liver cancer, cervical cancer, Esophageal cancer, Bladder cancer, Non-Hodgkin lymphoma, Leukemia, Pancreatic cancer, Kidney cancer, endometrial cancer, Head and neck cancer, Lip cancer, oral cancer, Thyroid cancer, Brain cancer, Ovary cancer, Melanoma, Gallbladder cancer, Laryngeal cancer, Multiple myeloma, Nasopharyngeal cancer, Hodgkin lymphoma, Testis cancer and Kaposi sarcoma.

In certain aspects, the method further includes administering a chemotherapeutic agent. The compounds of the disclosure can be administered in combination with one or more additional therapeutic agents. The phrases "combination therapy", "combined with" and the like refer to the use of more than one medication or treatment simultaneously to increase the response. The FGFR inhibitor of the present disclosure might for example be used in combination with other drugs or treatment in use to treat cancer. In various aspect, the compound is administered prior to, simultaneously with or following the administration of the chemotherapeutic agent.

The term "anti-cancer therapy" refers to any therapy or treatment that can be used for the treatment of a cancer.

Anti-cancer therapies include, but are not limited to, surgery, radiotherapy, chemotherapy, immune therapy and targeted therapies.

Examples of chemotherapeutic agents or anti-cancer agents include, but are not limited to, Actinomycin, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fiuorouracil, Gemcitabine, Hydroxyurea, Idarubicin, Imatinib, lrinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, Vinorelbine, panitumamab, Erbitux (cetuximab), matuzumab, IMC-IIF 8, TheraCIM hR3, denosumab, Avastin (bevacizumab), Humira (adalimumab), Herceptin (trastuzumab), Remicade (infliximab), rituximab, Synagis (palivizumab), Mylotarg (gemtuzumab oxogamicin), Raptiva (efalizumab), Tysabri (natalizumab), Zenapax (daclix-imab), NeutroSpec (Technetium (99mTc) fanolesomab), tocilizumab, ProstaScint (Indium-Ill labeled Capromab Pendetide), Bexxar (tositumomab), Zevalin (ibritumomab tiuxetan (IDEC-Y2B8) conjugated to yttrium 90), Xolair (omalizumab), MabThera (Rituximab), ReoPro (abciximab), MabCampath (alemtuzumab), Simulect (basiliximab), LeukoScan (sulesomab), CEA-Scan (arcitumomab), Verluma (nofetumomab), Panorex (Edrecolomab), alemtuzumab, CDP 870, natalizumab Gilotrif (afatinib), Lynparza (olaparib), Perjeta (pertuzumab), Otdivo (nivolumab), Bosulif (bosutinib), Cabometyx (cabozantinib), Ogivri (trastuzumab-dkst), Sutent (sunitinib malate), Adcetris (brentuximab vedotin), Alecensa (alectinib), Calquence (acalabrutinib), Yescarta (ciloleucel), Verzenio (abemaciclib), Keytruda (pembrolizumab), Aliqopa (copanlisib), Nerlynx (neratinib), Imfinzi (durvalumab), Darzalex (daratumumab), Tecentriq (atezolizumab), and Tarceva (erlotinib). Examples of immunotherapeutic agent include, but are not limited to, interleukins (Il-2, Il-7, Il-12), cytokines (Interferons, G-CSF, imiquimod), chemokines (CCL3, CCl26, CXCL7), immunomodulatory imide drugs (thalidomide and its analogues).

The term "adjuvant therapy" refers to a treatment added to a primary treatment to prevent recurrence of a disease, or the additional therapy given to enhance or extend the primary therapy's effect, as in chemotherapy's addition to a surgical regimen.

The term "agonist" as used herein refers to a chemical substance capable of activating a receptor to induce a full or partial pharmacological response. Receptors can be activated or inactivated by either endogenous or exogenous agonists and antagonists, resulting in stimulating or inhibiting a biological response. A physiological agonist is a substance that creates the same bodily responses, but does not bind to the same receptor. An endogenous agonist for a particular receptor is a compound naturally produced by the body which binds to and activates that receptor. A super agonist is a compound that is capable of producing a greater maximal response than the endogenous agonist for the target receptor, and thus an efficiency greater than 100%. This does not necessarily mean that it is more potent than the endogenous agonist, but is rather a comparison of the maximum possible response that can be produced inside a cell following receptor binding. Full agonists bind and activate a receptor, displaying full efficacy at that receptor. Partial agonists also bind and activate a given receptor, but have only partial efficacy at the receptor relative to a full agonist. An inverse agonist is an agent which binds to the same receptor binding-site as an agonist for that receptor and reverses constitutive activity of receptors. Inverse agonists exert the opposite pharmacological effect of a receptor agonist. An irreversible agonist is a type of agonist that binds permanently to a receptor in such a manner that the receptor is permanently activated. It is distinct from a mere agonist in that the association of an agonist to a receptor is reversible, whereas the binding of an irreversible agonist to a receptor is believed to be irreversible. This causes the compound to produce a brief burst of agonist activity, followed by desensitization and internalization of the receptor, which with long-term treatment produces an effect more like an antagonist. A selective agonist is specific for one certain type of receptor.

The term "antagonist" as used herein refers to a small molecule, peptide, protein, or antibody that can bind to an enzyme, a receptor or a co-receptor, competitively or non-competitively through a covalent bond, ionic bond, hydrogen bond, hydrophobic interaction, or a combination thereof and either directly or indirectly deactivate a related downstream signaling pathway.

The term "anti-cancer compounds" as used herein refers to small molecule compounds that selectively target cancer cells and reduce their growth, proliferation, or invasiveness, or tumor burden of a tumor containing such cancer cells.

The terms "analog" and "derivative" are used interchangeably to mean a compound produced from another compound of similar structure in one or more steps. A "derivative" or "analog" of a compound retains at least a degree of the desired function of the reference compound. Accordingly, an alternate term for "derivative" may be "functional derivative." Derivatives can include chemical modifications, such as akylation, acylation, carbamylation, iodination or any modification that derivatives the compound. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formal groups. Free carboxyl groups can be derivatized to form salts, esters, amides, or hydrazides. Free hydroxyl groups can be derivatized to form O-acyl or O-alkyl derivatives.

The term "allosteric modulation" as used herein refers to the process of modulating a receptor by the binding of allosteric modulators at a different site (i.e., regulatory site) other than of the endogenous ligand (orthosteric ligand) of the receptor and enhancing or inhibiting the effects of the endogenous ligand. It normally acts by causing a conformational change in a receptor molecule, which results in a change in the binding affinity of the ligand. Thus, an allosteric ligand "modulates" its activation by a primary "ligand" and can adjust the intensity of the receptor's activation. Many allosteric enzymes are regulated by their substrate, such a substrate is considered a "homotropic allosteric modulator." Non-substrate regulatory molecules are called "heterotropic allosteric modulators."

The term "allosteric regulation" is the regulation of an enzyme or other protein by binding an effector molecule at the proteins allosteric site (meaning a site other than the protein's active site). Effectors that enhance the protein's activity are referred to as "allosteric activators", whereas those that decrease the protein's activity are called "allosteric inhibitors." Thus, "allosteric activation" occurs when the binding of one ligand enhances the attraction between substrate molecules and other binding sites; "allosteric inhibition" occurs when the binding of one ligand decrease the affinity for substrate at other active sites. The term "antagonist" as used herein refers to a substance that counteracts the effects of another substance.

The term "assay marker" or "reporter gene" (or "reporter") refers to a gene that can be detected, or easily identified and measured. The expression of the reporter gene may be measured at either the RNA level, or at the protein level. The gene product, which may be detected in an experimental assay protocol, includes, but is not limited to, marker enzymes, antigens, amino acid sequence markers, cellular phenotypic markers, nucleic acid sequence markers, and the like. Researchers may attach a reporter gene to another gene of interest in cell culture, bacteria, animals, or plants. For example, some reporters are selectable markers, or confer characteristics upon on organisms expressing them allowing the organism to be easily identified and assayed. To introduce a reporter gene into an organism, researchers may place the reporter gene and the gene of interest in the same DNA construct to be inserted into the cell or organism. For bacteria or eukaryotic cells in culture, this may be in the form of a plasmid. Commonly used reporter genes may include, but are not limited to, fluorescent proteins, luciferase, beta-galactosidase, and selectable markers, such as chloramphenicol and kanomycin.

As used herein, the term "bioavailability" refers to the rate and extent to which the active drug ingredient or therapeutic moiety is absorbed into the systemic circulation from an administered dosage form as compared to a standard or control.

The term "biomarkers" (or "biosignatures") as used herein refers to peptides, proteins, nucleic acids, antibodies, genes, metabolites, or any other substances used as indicators of a biologic state. It is a characteristic that is measured objectively and evaluated as a cellular or molecular indicator of normal biologic processes, pathogenic processes, or pharmacologic responses to a therapeutic intervention. The term "indicator" as used herein refers to any substance, number or ratio derived from a series of observed facts that may reveal relative changes as a function of time; or a signal, sign, mark, note or symptom that is visible or evidence of the existence or presence thereof. Once a proposed biomarker has been validated, it may be used to diagnose disease risk, presence of disease in an individual, or to tailor treatments for the disease in an individual (choices of drug treatment or administration regimes). In evaluating potential drug therapies, a biomarker may be used as a surrogate for a natural endpoint, such as survival or irreversible morbidity. If a treatment alters the biomarker, and that alteration has a direct connection to improved health, the biomarker may serve as a surrogate endpoint for evaluating clinical benefit. Clinical endpoints are variables that can be used to measure how patients feel, function or survive. Surrogate endpoints are biomarkers that are intended to substitute for a clinical endpoint; these biomarkers are demonstrated to predict a clinical endpoint with a confidence level acceptable to regulators and the clinical community.

The term "bound" or any of its grammatical forms as used herein refers to the capacity to hold onto, attract, interact with or combine with.

The term "cell" is used herein to refer to the structural and functional unit of living organisms and is the smallest unit of an organism classified as living.

The term "cell line" as used herein refers to a population of immortalized cells, which have undergone transformation and can be passed indefinitely in culture.

The term "chemoresistance" as used herein refers to the development of a cell phenotype resistant to a variety of structurally and functionally distinct agents. Tumors can be intrinsically resistant prior to chemotherapy, or resistance may be acquired during treatment by tumors that are initially sensitive to chemotherapy. Drug resistance is a multifactorial phenomenon involving multiple interrelated or independent mechanisms. A heterogeneous expression of involved mechanisms may characterize tumors of the same type or cells of the same tumor and may at least in part reflect tumor progression. Exemplary mechanisms that can contribute to cellular resistance include: increased expression of defense factors involved in reducing intracellular drug concentration; alterations in drug-target interaction; changes in cellular response, in particular increased cell ability to repair DNA damage or tolerate stress conditions, and defects in apoptotic pathways.

The term "chemosensitive", "chemosensitivity" or "chemosensitive tumor" as used herein refers to a tumor that is responsive to a chemotherapy or a chemotherapeutic agent. Characteristics of a chemosensitive tumor include, but are not limit to, reduced proliferation of the population of tumor cells, reduced tumor size, reduced tumor burden, tumor cell death, and slowed/inhibited progression of the population of tumor cells.

The term "chemotherapeutic agent" as used herein refers to chemicals useful in the treatment or control of a disease, e.g., cancer.

The term "chemotherapy" as used herein refers to a course of treatment with one or more chemotherapeutic agents. In the context of cancer, the goal of chemotherapy is, e.g., to kill cancer cells, reduce proliferation of cancer cells, reduce growth of a tumor containing cancer cells, reduce invasiveness of cancer cells, increase apoptosis of cancer cells.

The term "chemotherapy regimen" ("combination chemotherapy") means chemotherapy with more than one drug in order to benefit from the dissimilar toxicities of the more than one drug. A principle of combination cancer therapy is that different drugs work through different cytotoxic mechanisms; since they have different dose-limiting adverse effects, they can be given together at full doses.

The term "compatible" as used herein means that the components of a composition are capable of being combined with each other in a manner such that there is no interaction that would substantially reduce the efficacy of the composition under ordinary use conditions.

The term "condition", as used herein, refers to a variety of health states and is meant to include disorders or diseases caused by any underlying mechanism or injury.

The term "contact" and its various grammatical forms as used herein refers to a state or condition of touching or of immediate or local proximity. Contacting a composition to a target destination, such as, but not limited to, an organ, a tissue, a cell, or a tumor, may occur by any means of administration known to the skilled artisan.

The term "derivative" as used herein means a compound that may be produced from another compound of similar structure in one or more steps. A "derivative" or "derivatives" of a peptide or a compound retains at least a degree of the desired function of the peptide or compound. Accordingly, an alternate term for "derivative" may be "functional derivative." Derivatives can include chemical modifications of the peptide, such as akylation, acylation, carbamylation, iodination or any modification that derivatizes the peptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formal groups. Free carboxyl groups can be derivatized to form salts, esters, amides, or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those peptides that contain one or more naturally occurring amino acid derivative of the twenty standard amino acids, for example, 4-hydroxyproline, 5-hydroxylysine, 3-methylhistidine, homoserine, ornithine or carboxyglutamiate, and can include amino acids that are not linked by peptide bonds. Such peptide derivatives can be incorporated during synthesis of a peptide, or a peptide can be modified by wellknown chemical modification methods (see, e.g., Glazer et al., Chemical Modification of Proteins, Selected Methods and Analytical Procedures, Elsevier Biomedical Press, New York (1975)).

The term "detectable marker" encompasses both selectable markers and assay markers. The term "selectable markers" refers to a variety of gene products to which cells transformed with an expression construct can be selected or screened, including drug-resistance markers, antigenic markers useful in fluorescence-activated cell sorting, adherence markers such as receptors for adherence ligands allowing selective adherence, and the like. When a nucleic acid is prepared or altered synthetically, advantage can be taken of known codon preferences of the intended host where the nucleic acid is to be expressed.

The term "detectable response" refers to any signal or response that may be detected in an assay, which may be performed with or without a detection reagent. Detectable responses include, but are not limited to, radioactive decay and energy (e.g., fluorescent, ultraviolet, infrared, visible) emission, absorption, polarization, fluorescence, phosphorescence, transmission, reflection or resonance transfer. Detectable responses also include chromatographic mobility, turbidity, electrophoretic mobility, mass spectrum, ultraviolet spectrum, infrared spectrum, nuclear magnetic resonance spectrum and x-ray diffraction. Alternatively, a detectable response may be the result of an assay to measure one or more properties of a biologic material, such as melting point, density, conductivity, surface acoustic waves, catalytic activity or elemental composition. The term "disease" or "disorder", as used herein, refers to an impairment of health or a condition of abnormal functioning.

As used herein, the term "enzymatic activity" refers to the amount of substrate consumed (or product formed) in a given time under given conditions. Enzymatic activity also may be referred to as "turnover number."

The term "functional equivalent" or "functionally equivalent" are used interchangeably herein to refer to substances, molecules, polynucleotides, proteins, peptides, or polypeptides having similar or identical biological activity to a reference substance, molecule, polynucleotide, protein, peptide, or polypeptide The term "half maximal inhibitory concentration" ("IC50") is a measure of the effectiveness of a compound in inhibiting a biological or biochemical function.

The terms "inhibiting", "inhibit" or "inhibition" are used herein to refer to reducing the amount or rate of a process, to stopping the process entirely, or to decreasing, limiting, or blocking the action or function thereof. Inhibition may include a reduction or decrease of the amount, rate, action function, or process of a substance by at least 5%, at least 10%, at least 15%, at least 20%, at least 25%, at least 30%, at least 40%, at least 45%, at least 50%, at least 55%, at least 60%, at least 65%, at least 70%, at least 75%, at least 80%, at least 85%, at least 90%, at least 95%, at least 98%, or at least 99%.

The term "inhibitor" as used herein refers to a molecule that binds to an enzyme thereby decreasing enzyme activity. Enzyme inhibitors are molecules that bind to enzymes thereby decreasing enzyme activity. The binding of an inhibitor may stop substrate from entering the active site of the enzyme and/or hinder the enzyme from catalyzing its reaction. Inhibitor binding is either reversible or irreversible. Irreversible inhibitors usually react with the enzyme and change it chemically, for example, by modifying key amino acid residues needed for enzymatic activity. In contrast, reversible inhibitors bind non-covalently and produce different types of inhibition depending on whether these inhibitors bind the enzyme, the enzyme-substrate complex, or both. Enzyme inhibitors often are evaluated by their specificity and potency.

The term "injury," as used herein, refers to damage or harm to a structure or function of the body caused by an outside agent or force, which may be physical or chemical.

The term "interfere" or "to interfere with" as used herein refers to the hampering, impeding, dampening, hindering, obstructing, blocking, reducing or preventing of an action or occurrence. By way of example, a receptor antagonist interferes with (e.g., blocks or dampens) an agonist-mediated response rather than provoking a biological response itself.

The term "invasion" or "invasiveness" as used herein refers to a process in malignant cells that includes penetration of and movement through surrounding tissues.

The term "Kaplan Meier plot" or "Kaplan Meier survival curve" as used herein refers to the plot of probability of clinical study subjects surviving in a given length of time while considering time in many small intervals. The Kaplan Meier plot assumes that: (i) at any time subjects who are censored (i.e., lost) have the same survival prospects as subjects who continue to be followed; (ii) the survival probabilities are the same for subjects recruited early and late in the study; and (iii) the event (e.g., death) happens at the time specified. Probabilities of occurrence of events are computed at a certain point of time with successive probabilities multiplied by any earlier computed probabilities to get a final estimate. The survival probability at any particular time is calculated as the number of subjects surviving divided by the number of subjects at risk. Subjects who have died, dropped out, or have been censored from the study are not counted as at risk.

The term "ligand" as used herein refers to a molecule that can bind selectively to a molecule, such that the binding interaction between the ligand and its binding partner is detectable over nonspecific interactions by a quantifiable assay. Derivatives, analogues and mimetic compounds are intended to be included within the definition of this term.

The terms "marker" and "cell surface marker" are used interchangeably herein to refer to a receptor, a combination of receptors, or an antigenic determinant or epitope found on the surface of a cell that allows a cell type to be distinguishable from other kinds of cells. Specialized protein receptors (markers) that have the capability of selectively binding or adhering to other signaling molecules coat the surface of every cell in the body. Cells use these receptors and the molecules that bind to them as a way of communicating with other cells and to carry out their proper function in the body. Cell sorting techniques are based on cellular biomarkers where a cell surface marker(s) may be used for either positive selection or negative selection, i.e., for inclusion or exclusion, from a cell population.

The term "maximum tolerated dose" (MTD) as used herein refers to the highest dose of a drug that does not produce unacceptable toxicity. The term "median survival" as used herein refers to the time after which 50% of individuals with a particular condition are still living and 50% have died. For example, a median survival of 6 months indicates that after 6 months, 50% of individuals with, e.g., colon cancer would be alive, and 50% would have passed away. Median survival is often used to describe the prognosis (i.e., chance of survival) of a condition when the average survival rate is relatively short, such as for colon cancer. Median survival is also used in clinical studies when a drug or treatment is being evaluated to determine whether or not the drug or treatment will extend life.

The term "metastasis" as used herein refers to the transference of organisms or of malignant or cancerous cells, producing disease manifestations, from one part of the body to other parts. The term "migration" as used herein refers to a movement of a population of cells from one place to another.

The term "modify" as used herein means to change, vary, adjust, temper, alter, affect or regulate to a certain measure or proportion in one or more particulars. The term "modifying agent" as used herein refers to a substance, composition, therapeutic component, active constituent, therapeutic agent, drug, metabolite, active agent, protein, non-therapeutic component, non-active constituent, non-therapeutic agent, or non-active agent that reduces, lessens in degree or extent, or moderates the form, symptoms, signs, qualities, character or properties of a condition, state, disorder, disease, symptom or syndrome. The term "modulate" as used herein means to regulate, alter, adapt, or adjust to a certain measure or proportion.

The term "neoplasm" as used herein refers to an abnormal proliferation of genetically altered cells. A malignant neoplasm (or malignant tumor) is synonymous with cancer. A benign neoplasm (or benign tumor) is a tumor (solid neoplasm) that stops growing by itself, does not invade other tissues and does not form metastases. The term "normal healthy control subject" as used herein refers to a subject having no symptoms or other clinical evidence of a disease. The term "normal human colonic epithelial cells" (HCECs) as used herein refers to immortalized human colonic epithelial cell (HCEC) lines generated using exogenously introduced telomerase and cdk4 (Fearon, E. R. & Vogelstein, B. A genetic model for colorectal tumorigenesis. Cell 61, 759-767 (1990)). These cells are non-transformed, karyotypically diploid and have multipotent characteristics. When placed in Matrigel® in the absence of a mesenchymal feeder layer, individual cells divide and form self-organizing, crypt-like structures with a subset of cells exhibiting markers associated with mature intestinal epithelium.

The term "outcome" as used herein refers to a specific result or effect that can be measured. Nonlimiting examples of outcomes include decreased pain, reduced tumor size, and survival (e.g., progression-free survival or overall survival).

The term "overall survival" (OS) as used herein refers to the length of time from either the date of diagnosis or the start of treatment for a disease, such as cancer, that patients diagnosed with the disease are still alive.

The term "parenteral" as used herein refers to introduction into the body by way of an injection (i.e., administration by injection), including, for example, subcutaneously (i.e., an injection beneath the skin), intramuscularly (i.e., an injection into a muscle); intravenously (i.e., an injection into a vein), intrathecally (i.e., an injection into the space around the spinal cord or under the arachnoid membrane of the brain), or infusion techniques. A parenterally administered composition is delivered using a needle, e.g., a surgical needle. The term "surgical needle" as used herein, refers to any needle adapted for delivery of fluid (i.e., capable of flow) compositions into a selected anatomical structure. Injectable preparations, such as sterile injectable aqueous or oleaginous suspensions, may be formulated according to the known art using exemplary dispersing or wetting agents and suspending agents.

The terms "primary tumor" or "primary cancer" are used interchangeably to refer to the original, or first, tumor in the body. Cancer cells from a primary cancer may spread to other parts of the body and form new, or secondary tumors. This is called metastasis. The secondary tumors are the same type of cancer as the primary cancer.

The term "progression" as used herein refers to the course of a disease as it becomes worse or spreads in the body. The term "progression-free survival" (PFS) as used herein refers to the length of time during and after the treatment of a disease that a patient lives with the disease but it does not get worse. The term "proliferation" as used herein refers to expansion of a population of cells by the continuous division of single cells into identical daughter cells, leading to a multiplying or increasing in the number of cells. The term "recurrence" as used herein refers to a disease (e.g., cancer) that has come back, usually after a period of time during which the disease could not be detected.

The term "reduce" or "reducing" as used herein refers to limit occurrence of a disorder in individuals at risk of developing the disorder. The terms "refractory" or "resistant" are used interchangeably herein refers to a disease or condition that does not respond to treatment. The disease may be resistant at the beginning of treatment or it may become resistant during treatment. The term "remission" as used herein refers to a decrease in or disappearance of signs and symptoms of a disease. In partial remission, some, but not all, signs and symptoms have disappeared. In complete remission, all signs and symptoms have disappeared although the disease may still be in the body.

The term Response Evaluation Criteria in Solid Tumors (or "RECIST") as used herein refers to a standard way to measure how well a cancer patient responds to treatment. It is based on whether tumors shrink, stay the same, or get bigger. To use RECIST, there must be at least one tumor that can be measured on x-rays, CT scans, or MRI scans. The types of response a patient can have are a complete response (CR), a partial response (PR), progressive disease (PD), and stable disease (SD).

The term "sign" as used herein refers to something found during a physical exam or from a laboratory test that shows that a person may have a condition or disease. The terms "subject" or "individual" or "patient" are used interchangeably to refer to a member of an animal species of mammalian origin, including but not limited to, a mouse, a rat, a cat, a goat, sheep, horse, hamster, ferret, platypus, pig, a dog, a guinea pig, a rabbit and a primate, such as, for example, a monkey, ape, or human. The term "subject in need of such treatment" as used herein refers to a patient who suffers from a disease, disorder, condition, or pathological process, e.g., a cancer.

The terms "substantial inhibition", "substantially inhibited" and the like as used herein refer to inhibition of at least 50%, inhibition of at least 55%, inhibition of at least 60%, inhibition of at least 65%, inhibition of at least 70%, inhibition of at least 75%, inhibition of at least 80%, inhibition of at least 85%, inhibition of at least 90%, inhibition of at least 95%, or inhibition of at least 99%.

The term "survival rate" as used herein refers to the percent of individuals who survive a disease (e.g., cancer) for a specified amount of time. For example, if the 5-year survival rate for a particular cancer is 34%, this means that 34 out of 100 individuals initially diagnosed with that cancer would be alive after 5 years.

The term "tumor" as used herein refers to a diseases involving abnormal cell growth in numbers (proliferation) or in size with the potential to invade or spread to other parts of the body (metastasis). The term "tumor burden" or "tumor load" are used interchangeably herein refers to the number of cancer cells, the size of a tumor, or the amount of cancer in the body.

In treatment, the dose of agent optionally ranges from about 0.0001 mg/kg to about 100 mg/kg, about 0.01 mg/kg to about 5 mg/kg, about 0.15 mg/kg to about 3 mg/kg, 0.5 mg/kg to about 2 mg/kg and about 1 mg/kg to about 2 mg/kg of the subject's body weight. In other embodiments the dose ranges from about 100 mg/kg to about 5 g/kg, about 500 mg/kg to about 2 mg/kg and about 750 mg/kg to about 1.5 g/kg of the subject's body weight. For example, depending on the type and severity of the disease, about 1 μg/kg to 15 mg/kg (e.g., 0.1-20 mg/kg) of agent is a candidate dosage for administration to the patient, whether, for example, by one or more separate administrations, or by continuous infusion. A typical daily dosage is in the range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. Unit doses can be in the range, for instance of about 5 mg to 500 mg, such as 50 mg, 100 mg, 150 mg, 200 mg, 250 mg and 300 mg. The progress of therapy is monitored by conventional techniques and assays.

In some embodiments, an agent is administered to a human patient at an effective amount (or dose) of less than about 1 μg/kg, for instance, about 0.35 to about 0.75 μg/kg or about 0.40 to about 0.60 μg/kg. In some embodiments, the dose of an agent is about 0.35 μg/kg, or about 0.40 μg/kg, or about 0.45 μg/kg, or about 0.50 μg/kg, or about 0.55 μg/kg, or about 0.60 μg/kg, or about 0.65 μg/kg, or about 0.70 μg/kg, or about 0.75 μg/kg, or about 0.80 μg/kg, or about 0.85 μg/kg, or about 0.90 μg/kg, or about 0.95 μg/kg or about 1 μg/kg. In various embodiments, the absolute dose of an agent is about 2 μg/subject to about 45 μg/subject, or about 5 to about 40, or about 10 to about 30, or about 15 to about 25 μg/subject. In some embodiments, the absolute dose of an agent is about 20 μg, or about 30 μg, or about 40 μg.

In various embodiments, the dose of an agent may be determined by the human patient's body weight. For example, an absolute dose of an agent of about 2 μg for a pediatric human patient of about 0 to about 5 kg (e.g. about 0, or about 1, or about 2, or about 3, or about 4, or about 5 kg); or about 3 μg for a pediatric human patient of about 6 to about 8 kg (e.g. about 6, or about 7, or about 8 kg), or about 5 μg for a pediatric human patient of about 9 to about 13 kg (e.g. 9, or about 10, or about 11, or about 12, or about 13 kg); or about 8 μg for a pediatric human patient of about 14 to about 20 kg (e.g. about 14, or about 16, or about 18, or about 20 kg), or about 12 μg for a pediatric human patient of about 21 to about 30 kg (e.g. about 21, or about 23, or about 25, or about 27, or about 30 kg), or about 13 μg for a pediatric human patient of about 31 to about 33 kg (e.g. about 31, or about 32, or about 33 kg), or about 20 μg for an adult human patient of about 34 to about 50 kg (e.g. about 34, or about 36, or about 38, or about 40, or about 42, or about 44, or about 46, or about 48, or about 50 kg), or about 30 μg for an adult human patient of about 51 to about 75 kg (e.g. about 51, or about 55, or about 60, or about 65, or about 70, or about 75 kg), or about 45 μg for an adult human patient of greater than about 114 kg (e.g. about 114, or about 120, or about 130, or about 140, or about 150 kg).

In certain embodiments, an agent in accordance with the methods provided herein is administered subcutaneously (s.c.), intravenously (i.v.), intramuscularly (i.m.), intranasally or topically. Administration of an agent described herein can, independently, be one to four times daily or one to four times per month or one to six times per year or once every two, three, four or five years. Administration can be for the duration of one day or one month, two months, three months, six months, one year, two years, three years, and may even be for the life of the human patient. The dosage may be administered as a single dose or divided into multiple doses. In some embodiments, an agent is administered about 1 to about 3 times (e.g. 1, or 2 or 3 times).

The following example is provided to further illustrate the advantages and features of the present disclosure, but it is not intended to limit the scope of the disclosure. While this example is typical of those that might be used, other procedures, methodologies, or techniques known to those skilled in the art may alternatively be used.

EXAMPLES

Example 1

Synthesis of Compound 1 (Synthetic Routes 1 and 2)

Scheme 1. Synthetic route 1 for compound 1.

Compound 1

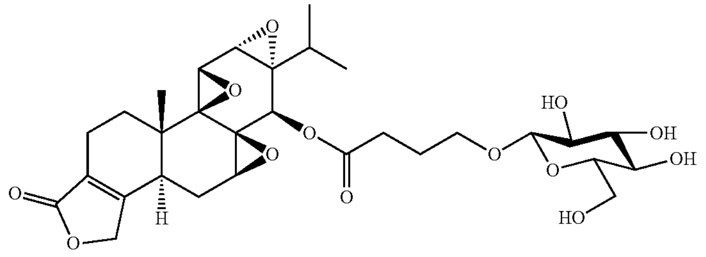

-continued
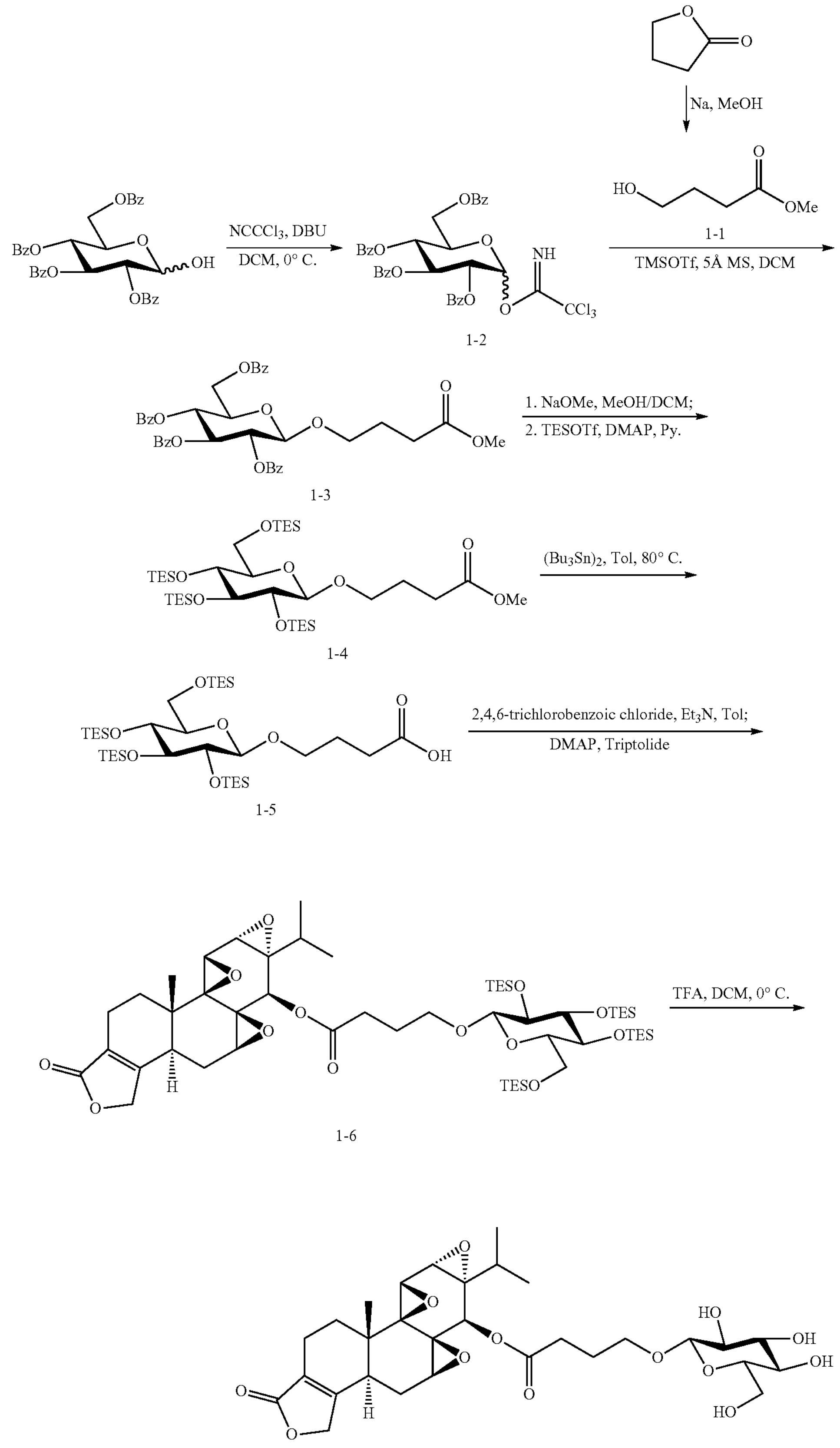
compound 1

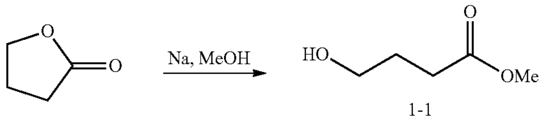 [SMILES: O=C1CCCO1 ; COC(=O)CCCO]

1-1

Intermediate 1-1: To a solution of gamma-Butyrolactone (4.3 mL, 56.5 mmol) in methanol (150 mL) at 0° C., was added Na (1.3 g, 56.5 mmol). Stirring was continued until complete conversion of the starting material (monitored by TLC, about 24 hours). The reaction was quenched with saturated ammonium chloride (300 mL), extracted with ethyl acetate (150 mL×4), the organic layer was combined, washed with brine (100 mL×4), dried over $Na_2SO_4$. The mixture was filtered and concentrated. Column chromatography (Petroleum ether/Ethyl acetate=2/1) afforded the intermediate product 1-1 as a colorless liquid (4.5 g, 38.1 mmol, 67%). $^1$H NMR (500 MHz, $CDCl_3$) δ 3.68-3.59 (m, 5H), 2.41 (t, J=7.2 Hz, 2H), 1.85 (ddd, J=7.2, 6.1, 1.0 Hz, 2H). $^{13}$C NMR (125 MHz, $CDCl_3$) δ 174.54, 61.94, 51.76, 30.82, 27.75.

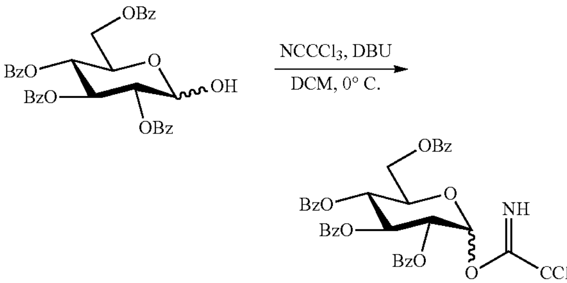

1-2

Intermediate 1-2: The lactol (4.4 g, 7.4 mmol) was dissolved in $CH_2Cl_2$ (50 mL) and cooled to 0° C. Trichloroacetonitrile (3.7 mL, 36.9 mmol) and DBU (52 μL, 0.4 mmol) were added successively. After stirring at room temperature for about 2 h, the reaction mixture was concentrated in vacuo. The residue was chromatographed over silica gel (Petroleum ether/EtOAc=4:1, containing 1% $Et_3N$) to yield imidate intermediate product 1-2 (4.9 g, 6.6 mmol, 90%) as a colorless oil.

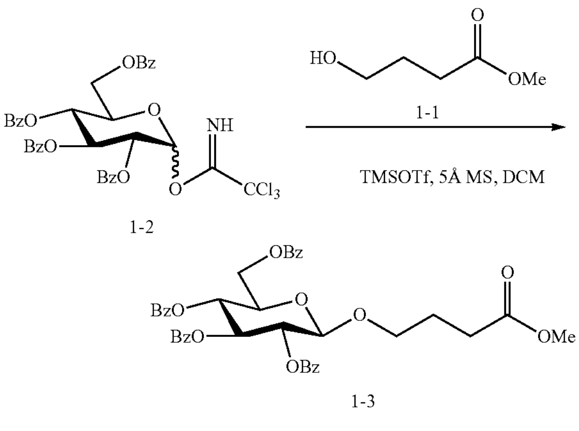

1-1

1-2

1-3

Intermediate 1-3: Trichloroacetimidate donor 1-2 (1.8 g, 2.4 mmol) and intermediate 1-1 (260 mg, 2.2 mmol) were dissolved in $CH_2Cl_2$ (25 mL) under nitrogen at 0° C. Powdered freshly activated 5 Å molecular sieves (2 g) were added. After 15 min, TMSOTf (40 μL, 0.22 mmol) was added and stirring was continued at 0° C. until TLC indicated the disappearance of the donor (about 8 h). The mixture was filtered through Celite, and the filtrated was concentrated in vacuum. The residue was purified by silica gel column chromatography (petroleum ether/EtOAc, 2:1) to give intermediate 1-3 (1.23 g, 1.77 mmol, 80%) as a white foam. $^1$H NMR (400 MHz, $CDCl_3$) δ 8.06-8.00 (m, 2H), 8.00-7.93 (m, 2H), 7.93-7.87 (m, 2H), 7.88-7.81 (m, 2H), 7.61-7.28 (m, 13H), 5.90 (t, J=9.6 Hz, 1H), 5.67 (t, J=9.7 Hz, 1H), 5.51 (dd, J=9.8, 7.8 Hz, 1H), 4.84 (d, J=7.9 Hz, 1H), 4.64 (dd, J=12.1, 3.3 Hz, 1H), 4.50 (dd, J=12.1, 5.2 Hz, 1H), 4.20-4.14 (m, 1H), 3.95 (dt, J=9.8, 5.9 Hz, 1H), 3.62 (ddd, J=9.8, 7.0, 5.6 Hz, 1H), 3.52 (s, 3H), 2.29 (t, J=7.3 Hz, 2H), 1.95-1.76 (m, 2H). $^{13}$C NMR (100 MHz, $CDCl_3$) δ 173.72, 166.25, 165.92, 165.28, 165.20, 133.54, 133.35, 133.32, 133.25, 130.00, 129.91, 129.87, 129.86, 129.84, 129.82, 129.63, 129.31, 128.84, 128.82, 128.50, 128.47, 128.46, 128.39, 101.30, 72.97, 72.27, 71.94, 69.80, 68.94, 63.21, 51.51, 30.04, 24.79. ESI-MS m z calcd for $C_{39}H_{36}O_{12}Na$ $[M+Na]^+$ 719.2099, found 719.2102.

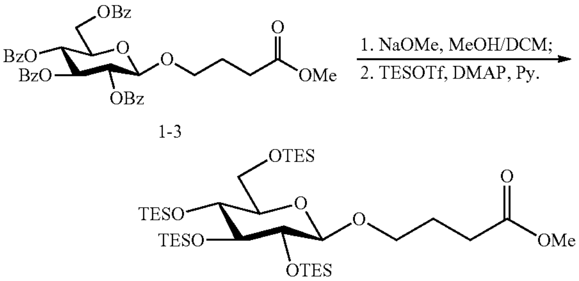

1-3

1-4

Intermediate 1-4: To a solution of intermediate 1-3 (2.9 g, 4.4 mmol) in methanol (20 mL), was added NaOMe (120 mg, 2.2 mmol). Stirring was continued until complete conversion of the starting material (monitored by TLC, about 8 hours). The mixture was neutralized with acidic resin, filtered and concentrated. Then the mixture was coevaporated with toluene three times and dried in vacuo.

The mixture was dissolved in dry pyridine (20 mL), and cooled to 0° C. DMAP (108 mg, 0.9 mmol) and TESOTf (6.0 mL, 26.4 mmol) was added slowly over 5 min. Stirring was continued at 0° C. until complete conversion of the starting material (monitored by TLC, about 8 hours). The reaction was concentrated, then diluted with ethyl acetate, and washed twice with 2% HCl, once with saturated and brine, dried over $Na_2SO_4$. Then, the mixture was filtered and concentrated. Column chromatography (Petroleum ether/Ethyl acetate=30/1) afforded the intermediate product 1-4 as a colorless liquid (2.4 g, 3.3 mmol, 75% for two steps). $^1$H NMR (400 MHz, $CDCl_3$) δ 4.38 (d, J=6.9 Hz, 1H), 3.92-3.81 (m, 1H), 3.77 (dd, J=10.4, 5.4 Hz, 1H), 3.72-3.63 (m, 5H), 3.60 (dd, J=5.9, 4.6 Hz, 1H), 3.53-3.37 (m, 3H), 2.41 (d, J=19.8 Hz, 2H), 1.94 (t, J=7.0 Hz, 2H), 0.98-0.92 (m, 36H), 0.62 (dd, J=15.4, 7.6 Hz, 24H). $^{13}$C NMR (100 MHz, $CDCl_3$) δ 174.01, 102.48, 79.79, 79.27, 77.23, 71.27, 67.95, 63.28, 51.66, 30.98, 25.25, 7.17, 7.10, 6.89, 5.28, 5.20, 5.13, 4.56; ESI-MS m z calcd for $C_{35}H_{76}O_8Si_4Na$ $[M+Na]^+$ 759.4509, found 759.4515.

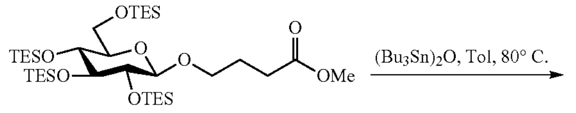

1-4

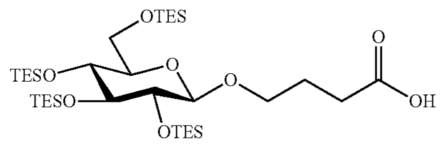

1-5

Intermediate 1-5: To a solution of intermediate 1-4 (850 mg, 1.2 mmol) in toluene (12 mL), was added bis(tributyltin) oxide (4.7 mL, 9.2 mmol). The reaction was heated to 80° C. overnight. The mixture was concentrated. Then the mixture was coevaporated with toluene three times. Column chromatography (Petroleum ether/Ethyl acetate=20/1 to 10/1) afforded the product as a colorless liquid as intermediate 1-5 (450 mg, 0.62 mmol, 54%), recovered starting material (250 mg, 0.34 mmol, 29%). $^1H$ NMR (400 MHz, $CDCl_3$) δ 4.40 (d, J=6.9 Hz, 1H), 3.86 (d, J=9.5 Hz, 1H), 3.76 (d, J=5.2 Hz, 1H), 3.75-3.64 (m, 2H), 3.60 (t, J=5.2 Hz, 1H), 3.55-3.40 (m, 3H), 2.52-2.45 (m, 2H), 1.96 (q, J=7.0 Hz, 2H), 0.98-0.92 (m, 36H), 0.74-0.48 (m, 24H); ESI-MS m z calcd for $C_{34}H_{74}O_8Si_4Na$ $[M+Na]^+$ 745.4353, found 745.4358.

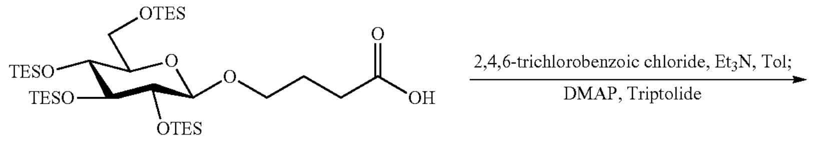

1-5

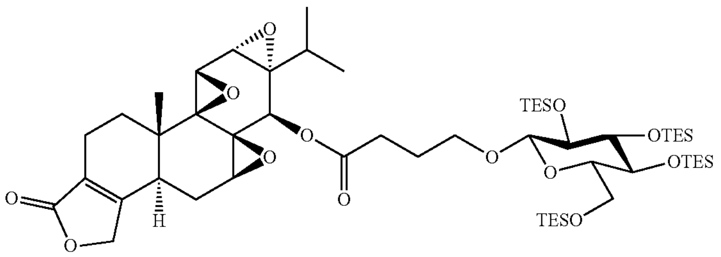

1-6

Intermediate 1-6: To a solution of intermediate 1-5 (475 mg, 0.53 mmol) in toluene (9 mL) was added $NEt_3$ (0.29 mL, 2.1 mmol) and 2,4,6-trichlorobenzoyl chloride (0.25 mL, 1.6 mmol) at 0° C. and was stirred at room temperature for 0.5 h. After the formation of mixed anhydride (TLC), the solution was cooled to 0° C. and 4-(dimethylamino)pyridine (428 mg, 3.5 mmol) and triptolide (126 mg, 0.35 mmol) was introduced dropwise in to the reaction mixture. The reaction mixture was warmed to room temperature and was stirred for additional 5 h. After the completion of the reaction (TLC), it was quenched by addition of saturated $NaHCO_3$ solution (10 mL) and the aqueous layer was washed with DCM (3×10 mL). The combined organic layer was washed with brine (5 mL), dried over $Na_2SO_4$. The mixture was filtered and concentrated. Purification by silica gel column chromatography (PE/EtOAc, 2:1) afforded ester intermediate product 1-6 (339 mg, 0.32 mmol, 91%). $^1H$ NMR (400 MHz, $CDCl_3$) δ 5.02 (d, J=1.0 Hz, 1H), 4.60 (s, 2H), 4.34 (d, J=6.9 Hz, 1H), 3.88-3.77 (m, 1H), 3.76-3.67 (m, 2H), 3.68-3.58 (m, 2H), 3.54 (dd, J=5.8, 4.5 Hz, 1H), 3.50-3.32 (m, 6H), 2.60 (s, 1H), 2.55-2.35 (m, 2H), 2.31-2.19 (m, 1H), 2.14-2.01 (m, 2H), 1.98-1.89 (m, 3H), 1.84-1.77 (m, 2H), 0.93-0.86 (m, 36H), 0.64-0.47 (m, 24H); ESI-MS m z calcd for $C_{54}H_{96}O_{13}Si_4Na$ $[M+Na]^+$ 1087.5820, found 1087.5801.

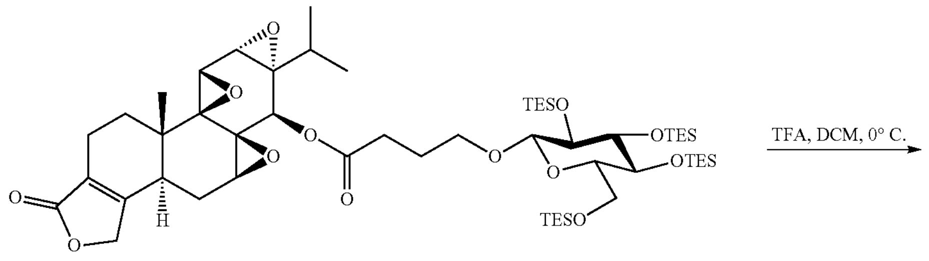

1-6

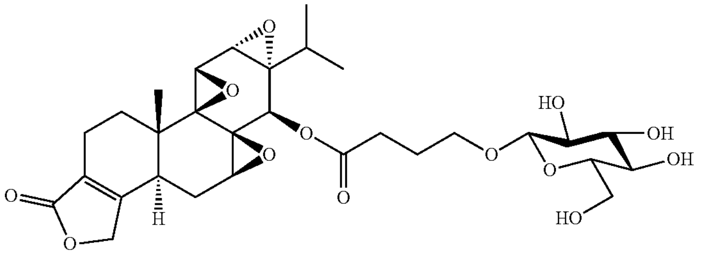

compound 1

Compound 1: Intermediate 1-6 (570 mg, 0.54 mmol) was dissolved in DCM (10 mL), and cooled to 0° C. Then TFA (1.0 mL) was added. After stirring at this temperature for about 15 min, the reaction mixture was concentrated in vacuo. The residue was chromatographed over silica gel (DCM/Methanol=15:1) to yield compound 1 (300 mg, 0.49 mml, 91%) as a white solid. $^1$H NMR (500 MHz, $CD_3OD$) δ 5.09 (d, J=1.0 Hz, 1H), 4.83-4.72 (m, 2H), 4.26 (d, J=7.8 Hz, 1H), 4.03-3.92 (m, 2H), 3.86 (dd, J=11.9, 2.1 Hz, 1H), 3.72-3.59 (m, 3H), 3.47 (d, J=5.7 Hz, 1H), 3.18 (dd, J=9.1, 7.8 Hz, 1H), 2.78 (d, J=13.1 Hz, 1H), 2.69-2.46 (m, 2H), 2.32-2.19 (m, 2H), 2.08 (t, J=13.8 Hz, 1H), 2.03-1.77 (m, 4H), 1.51 (dd, J=12.4, 5.0 Hz, 1H), 1.37-1.27 (m, 1H), 1.04 (s, 3H), 0.95 (d, J=7.0 Hz, 3H), 0.84 (d, J=6.9 Hz, 3H). $^{13}$C NMR (100 MHz, $CD_3OD$) δ 176.07, 174.57, 163.87, 125.51, 104.49, 78.00, 77.90, 75.08, 72.66, 71.98, 71.61, 69.68, 64.88, 64.21, 62.76, 61.10, 56.74, 56.21, 41.44, 36.81, 31.85, 30.82, 29.48, 26.35, 24.17, 17.94, 17.91, 17.13, 14.23; ESI-MS m z calcd for $C_{30}H_{40}O_{13}Na$ $[M+Na]^+$ 631.2361, found 631.2368.

Scheme 2. Synthetic route 2 for compound 1.

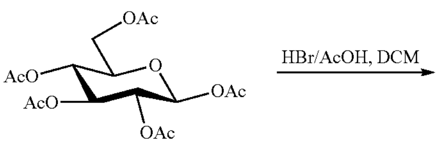

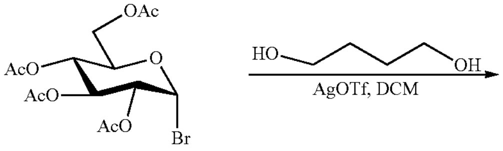

1-7

-continued

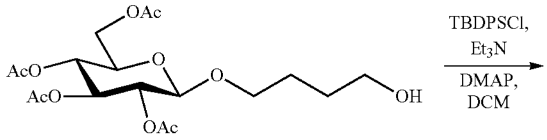

1-8

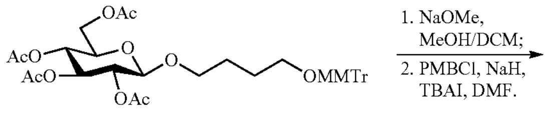

1-9

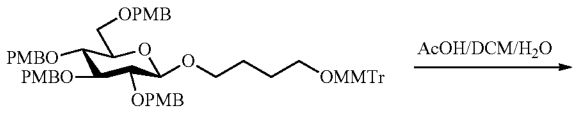

1-10

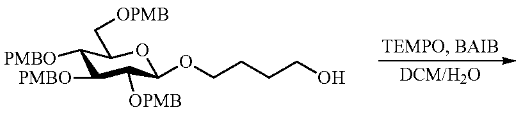

1-11

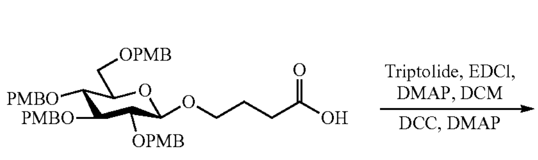

1-12

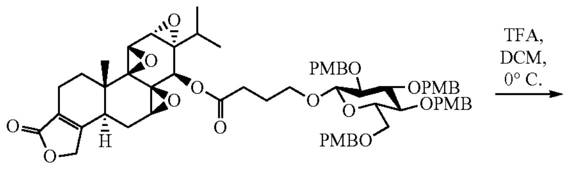

1-13

-continued

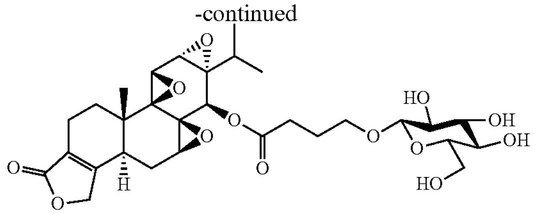

compound 1

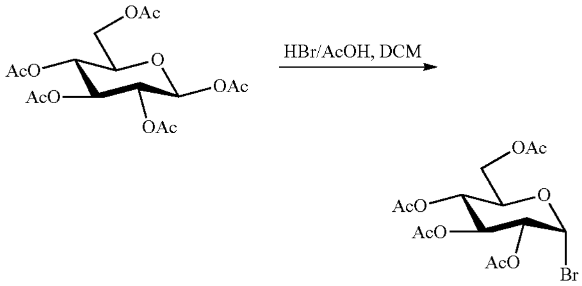

1-7

Intermediate 1-7: To a solution of β-D-glucose pentaacetate (5.0 g, 12.8 mmol) in DCM (30 mL) at 0° C., was added hydrobromic acid solution in acetic acid (8 mL). Stirring was continued at 0° C. until complete conversion of starting material (about 3 h). The reaction mixture was quenched with ice water (200 mL), and extracted with DCM (3x80 mL). The organic layer was combined and washed with ice water (3x80 mL), saturated $NaHCO_3$, and brine, dried over $Na_2SO_4$. The mixture was filtered and concentrated to provide 2,3,4,6-Tetra-O-acetyl-α-D-glucopyranosyl bromide as intermediate 1-7 (4.85 g, 11.8 mmol, 92%) as a white solid.

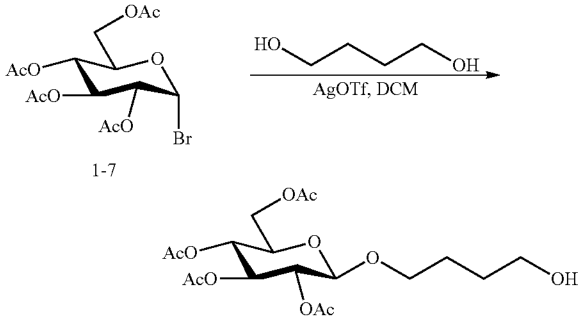

1-7

1-8

Intermediate 1-8: 2,3,4,6-Tetra-O-acetyl-α-D-glucopyranosyl bromide intermediate 1-7 (8.0 g, 2.4 mmol) and 1,4-Butylene glycol (260 mg, 2.2 mmol) were dissolved in $CH_2Cl_2$ (25 mL) under nitrogen. AgOTf (5.5 g, 21.5 mmol) were added. Stirring was continued until TLC indicated the disappearance of the donor (about 2 h). The mixture was quenched with saturated $NaHCO_3$, and filtered through Celite. The filtration was diluted with DCM, and washed with saturated $NaHCO_3$ and brine, dried over $Na_2SO_4$. The mixture was filtered and concentrated in vacuum. The residue was coevaporated with toluene twice.

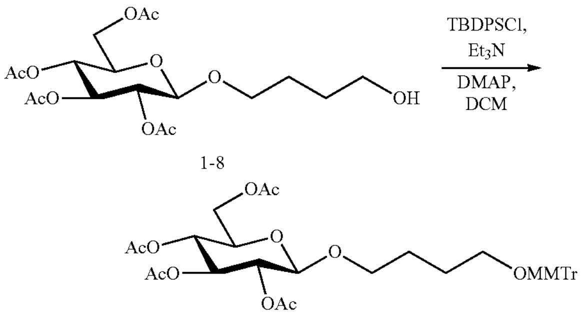

1-8

1-9

Intermediate 1-9: To a solution of intermediate 1-8 in pyridine (40 mL) at 0° C., DMAP (500 mg, 3.9 mmol) and MMTrCl (12.0 g, 39.0 mmol) was added. Stirring was continued at room temperature until complete consume of starting material. The mixture was concentrated, then diluted with ethyl acetate. The organic layer was was washed with saturated $CuSO_4$ (2x100 mL), and brine, dried over $Na_2SO_4$. The mixture was filtered and concentrated. Purification by silica gel column chromatography (PE/EtOAc, 3:1) afforded ester intermediate 1-9 (6.8 g, 9.5 mmol, 50% for two steps). $^1$H NMR (400 MHz, $CDCl_3$) δ 7.42-7.31 (m, 4H), 7.29-7.11 (m, 8H), 6.76 (d, J=8.9 Hz, 2H), 5.12 (t, J=9.5 Hz, 1H), 5.01 (t, J=9.7 Hz, 1H), 4.90 (dd, J=9.6, 8.0 Hz, 1H), 4.36 (d, J=7.9 Hz, 1H), 4.19 (dd, J=12.3, 4.6 Hz, 1H), 4.10-3.98 (m, 1H), 3.80 (dt, J=10.7, 5.6 Hz, 1H), 3.73 (s, 3H), 3.59 (ddd, J=9.8, 4.6, 2.4 Hz, 1H), 3.45-3.32 (m, 1H), 3.03-2.93 (m, 2H), 2.00 (s, 3H), 1.96 (s, 3H), 1.94 (s, 6H), 1.61-1.56 (m, 4H). $^{13}$C NMR (100 MHz, $CDCl_3$) δ 170.89, 170.49, 169.56, 158.80, 147.19, 144.93, 139.32, 130.41, 129.35, 128.51, 128.03, 127.96, 127.86, 127.32, 126.89, 113.33, 113.11, 100.95, 100.91, 81.86, 77.36, 72.92, 71.92, 71.42, 70.15, 68.51, 62.52, 62.02, 55.40, 29.48, 25.99, 20.93, 20.85, 20.80, 20.78; ESI-MS m z calcd for $C_{38}H_{44}O_{12}Na$ $[M+Na]^+$ 715.2725, found 715.2722.

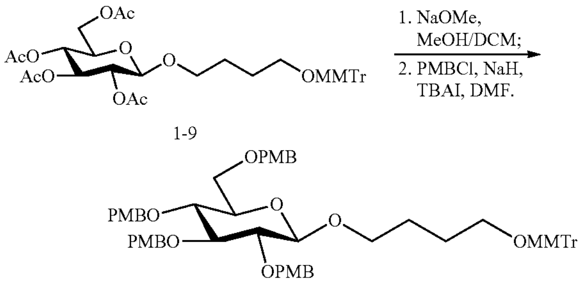

1-9

1-10

Intermediate 1-10: To a solution of intermediate 1-9 (8.0 g, 11.6 mmol) in methanol (60 mL) and DCM (15 mL), was added NaOMe (312 mg, 5.8 mmol). Stirring was continued until complete conversion of the starting material (monitored by TLC, about 6 hours). The mixture was neutralized with acid resin, filtered and concentrated. Then the mixture was coevaporated with toluene three times and dried in vacuo.

The mixture and TBAI (854 mg, 2.3 mmol) was dissolved in dry DMF (100 mL), and cooled to 0° C. NaH (2.8 g, 60% suspension, 69.4 mmol) was added slowly over 5 min. After 20 min, PMBCl (9.4 mL, 69.4 mmol) was added and the reaction stirred for another 10 min, at which time the temperature was raised to room temperature for 4 h. The reaction was re-cooled to 0° C. and water was added to quench the reaction. The organic layer was diluted with ethyl acetate, and washed twice with water, once with brine, dried over $Na_2SO_4$. Then, the mixture was filtered and concentrated. Column chromatography (Petroleum ether/Ethyl acetate=3/1) afforded the intermediate 1-10 as a white solid (11.0 g, 10.9 mmol, 94% for two steps). $^1H$ NMR (400 MHz, $CDCl_3$) δ 7.50-7.43 (m, 4H), 7.37-7.20 (m, 14H), 7.11-7.04 (m, 2H), 6.94-6.78 (m, 10H), 4.88 (dd, J=10.6, 4.7 Hz, 2H), 4.74 (d, J=10.3 Hz, 2H), 4.69-4.61 (m, 1H), 4.57 (d, J=11.8 Hz, 1H), 4.49 (d, J=11.8 Hz, 1H), 4.43 (d, J=10.4 Hz, 1H), 4.36 (d, J=7.8 Hz, 1H), 3.99 (dd, J=9.8, 5.1 Hz, 1H), 3.87-3.75 (m, 15H), 3.72-3.48 (m, 5H), 3.46-3.36 (m, 2H), 3.13 (d, J=5.6 Hz, 2H), 1.79 (t, J=5.4 Hz, 4H). $^{13}C$ NMR (100 MHz, $CDCl_3$) δ 159.34, 159.28, 159.27, 159.23, 158.48, 144.98, 136.22, 131.03, 130.75, 130.39, 130.34, 129.96, 129.74, 129.60, 128.74, 128.52, 127.82, 126.81, 114.03, 113.89, 113.87, 113.86, 113.84, 113.08, 103.74, 86.10, 84.52, 82.08, 77.76, 75.44, 74.94, 74.73, 74.61, 73.18, 70.01, 68.64, 63.28, 55.37, 55.34, 55.28, 26.97, 26.91; ESI-MS m z calcd for $C_{62}H_{68}O_{12}Na$ [M+Na]$^+$ 1027.4603, found 1027.4600.

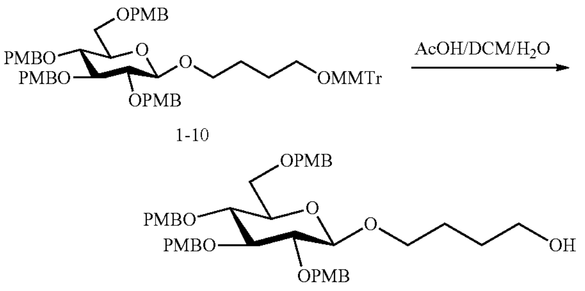

1-10

1-11

Intermediate 1-11: After a solution of intermediate 1-10 (11.0 g, 10.9 mmol) in AcOH/$CH_2C12/H_2O$ (15:4:1, 120 mL) was stirred at room temperature for 2.0 h, it was diluted with $CH_2Cl_2$ and poured into cold water. The organic layer was washed with water (4×80 mL), saturated aqueous $NaHCO_3$ and brine, then dried over $Na_2SO_4$. After concentration in vacuum, the residue was purified by silica gel column chromatography (Petroleum ether/Ethyl acetate=1/1) to give intermediate 1-11 (7.2 g, 9.8 mmol, 90%) as a white solid. $^1H$ NMR (400 MHz, $CDCl_3$) δ 7.26-7.13 (m, 6H), 7.07-6.86 (m, 2H), 6.86-6.55 (m, 8H), 4.77 (dd, J=10.6, 2.6 Hz, 2H), 4.64 (dd, J=10.5, 2.0 Hz, 2H), 4.59 (d, J=10.6 Hz, 1H), 4.47 (d, J=11.8 Hz, 1H), 4.40 (d, J=11.8 Hz, 1H), 4.33 (d, J=10.4 Hz, 1H), 4.29 (d, J=7.8 Hz, 1H), 3.96-3.87 (m, 1H), 3.79-3.68 (m, 12H), 3.66-3.47 (m, 6H), 3.42 (t, J=9.2 Hz, 1H), 3.37-3.27 (m, 2H), 1.64 (dt, J=18.4, 6.1 Hz, 4H). $^{13}C$ NMR (100 MHz, $CDCl_3$) δ 159.32, 159.28, 159.26, 159.21, 130.95, 130.73, 130.32, 130.24, 129.83, 129.73, 129.60, 129.55, 113.86, 113.84, 113.82, 103.68, 84.53, 82.05, 77.72, 75.40, 74.88, 74.71, 74.59, 73.14, 70.02, 68.59, 62.62, 55.35, 55.32, 29.67, 26.38; ESI-MS m z calcd for $C_{42}H_{52}O_{11}Na$ [M+Na]$^+$ 755.3402, found 755.3409.

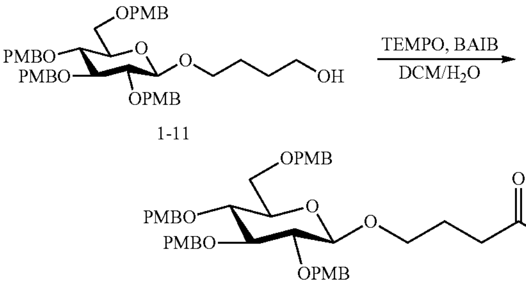

1-11

1-12

Intermediate 1-12: To a solution of intermediate 1-11 (1.8 g, 2.4 mmol) in DCM (12 mL) and water (6 mL), TEMPO (75 mg, 0.48 mmol) and BAIB (2.3 g, 7.2 mmol) was added. Stirring was continued until complete conversion of starting material (about 3 hours). The mixture was quenched with saturated $NaHSO_3$, and extracted with DCM three times. The organic layer was combined and washed with brine, dried over $Na_2SO_4$. After concentration in vacuum, the residue was purified by silica gel column chromatography (Petroleum ether/Ethyl acetate=1/4) to give intermediate 1-12 (1.3 g, 1.7 mmol, 73%) as a white solid. $^1H$ NMR (400 MHz, $CDCl_3$) δ 7.30-7.11 (m, 6H), 6.96 (d, J=8.2 Hz, 2H), 6.88-6.63 (m, 8H), 4.75 (dd, J=10.6, 3.0 Hz, 2H), 4.61 (dd, J=23.8, 10.7 Hz, 3H), 4.51-4.28 (m, 3H), 4.27 (d, J=7.7 Hz, 1H), 3.96-3.81 (m, 1H), 3.72-3.71 (m, 12H), 3.65-3.23 (m, 8H), 2.43 (t, J=7.4 Hz, 2H), 2.06-1.90 (m, 2H). $^{13}C$ NMR (100 MHz, $CDCl_3$) δ 178.66, 159.35, 159.31, 159.24, 130.96, 130.66, 130.36, 130.22, 129.93, 129.75, 129.65, 129.59, 113.92, 113.87, 103.63, 84.52, 82.04, 77.68, 75.44, 74.90, 74.73, 73.18, 68.74, 68.52, 55.38, 30.77, 25.03; ESI-MS m z calcd for $C_{42}H_{50}O_{12}Na$ [M+Na]$^+$ 769.3194, found 769.3196.

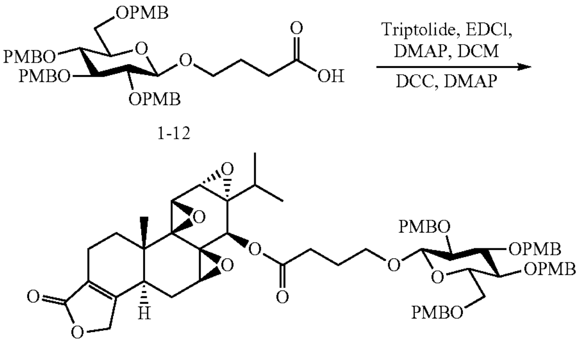

1-12

1-13

Intermediate 1-13: A solution of intermediate 1-12 (1.3 g, 1.7 mmol), Triptolide (523 mg, 1.45 mmol), DMAP (36 mg, 0.3 mmol), and DCC (462 mg, 2.2 mmol) in $CH_2Cl_2$ (30 mL) was stirred for 8 h at RT. The resulting mixture was concentrated and diluted with ethyl acetate, then filtrated. The filtrate was concentrated in vacuum. The residue was purified by silica gel column chromatography (petroleum ether/EtOAc, 1:1) to give intermediate product 1-13 (1.3 g, 1.2 mmol, 82%) as a white solid. $^1H$ NMR (400 MHz, $CDCl_3$) δ 7.27-7.12 (m, 6H), 6.96 (d, J=8.6 Hz, 2H), 6.85-6.66 (m, 8H), 5.06-4.97 (m, 1H), 4.77 (t, J=11.0 Hz, 2H), 4.69-4.54 (m, 5H), 4.48 (d, J=11.8 Hz, 1H), 4.39 (d, J=11.9 Hz, 1H), 4.32 (d, J=10.4 Hz, 1H), 4.28 (d, J=7.8 Hz, 1H), 4.11-4.03 (m, 1H), 3.79-3.70 (m, 13H), 3.60-3.30 (m, 10H), 2.67-2.42 (m, 4H), 0.95 (s, 3H), 0.87 (d, J=6.9 Hz, 3H), 0.73 (d, J=6.9 Hz, 3H). $^{13}$C NMR (100 MHz, $CDCl_3$) δ 173.38, 172.76, 160.16, 159.33, 159.27, 159.21, 130.97, 130.77, 130.36, 130.28, 130.00, 129.72, 129.61, 129.56, 125.64, 113.88, 113.85, 103.75, 84.49, 82.01, 77.66, 75.42, 74.92, 74.73, 74.64, 73.18, 70.94, 70.09, 68.78, 68.55, 63.61, 63.40, 61.25, 59.83, 55.37, 55.34, 55.09, 49.20, 40.43, 35.75, 34.04, 31.18, 29.89, 28.15, 25.72, 25.37, 25.05, 23.52, 17.66, 17.14, 16.80, 13.83. ESI-MS m z calcd for $C_{62}H_{72}O_{17}Na$ $[M+Na]^+$ 1111.4662, found 1111.4649.

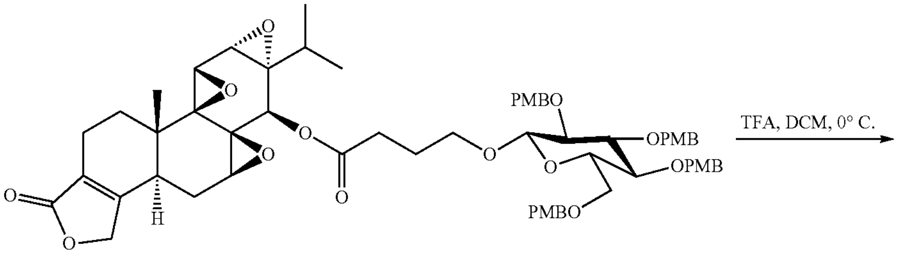

1-13

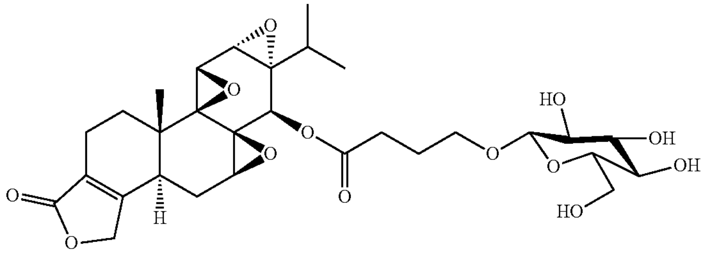

compound 1

Compound 1: Intermediate 1-13 (1.0 g, 1.45 mmol) was dissolved in DCM (30 mL), and cooled to 0° C. Then TFA (3.0 mL) was added. After stirring at this temperature for about 15 min, the reaction mixture was concentrated in vacuo. The residue was chromatographed over silica gel (DCM/Methanol=15:1) to yield final product compound 1 (510 mg, 0.84 mmol, 58%) as a white solid. $^{1}$H NMR (500 MHz, $CD_3OD$) δ 5.09 (d, J=1.0 Hz, 1H), 4.83-4.72 (m, 2H), 4.26 (d, J=7.8 Hz, 1H), 4.03-3.92 (m, 2H), 3.86 (dd, J=11.9, 2.1 Hz, 1H), 3.72-3.59 (m, 3H), 3.47 (d, J=5.7 Hz, 1H), 3.18 (dd, J=9.1, 7.8 Hz, 1H), 2.78 (d, J=13.1 Hz, 1H), 2.69-2.46 (m, 2H), 2.32-2.19 (m, 2H), 2.08 (t, J=13.8 Hz, 1H), 2.03-1.77 (m, 4H), 1.51 (dd, J=12.4, 5.0 Hz, 1H), 1.37-1.27 (m, 1H), 1.04 (s, 3H), 0.95 (d, J=7.0 Hz, 3H), 0.84 (d, J=6.9 Hz, 3H). $^{13}$C NMR (100 MHz, $CD_3OD$) δ 176.07, 174.57, 163.87, 125.51, 104.49, 78.00, 77.90, 75.08, 72.66, 71.98, 71.61, 69.68, 64.88, 64.21, 62.76, 61.10, 56.74, 56.21, 41.44, 36.81, 31.85, 30.82, 29.48, 26.35, 24.17, 17.94, 17.91, 17.13, 14.23; ESI-MS m z calcd for $C_{30}H_{40}O_{13}Na$ $[M+Na]^+$ 631.2361, found 631.2368.

Example 2

Synthesis of Compound 2

Scheme 3. Synthesis of compound 2.

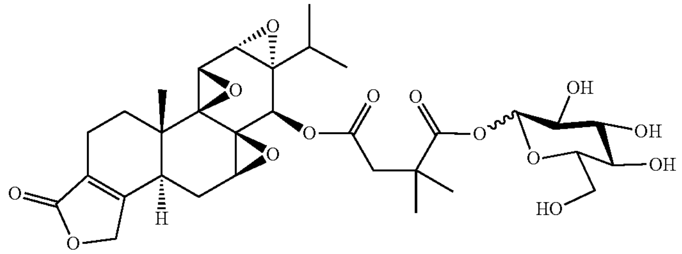

-continued

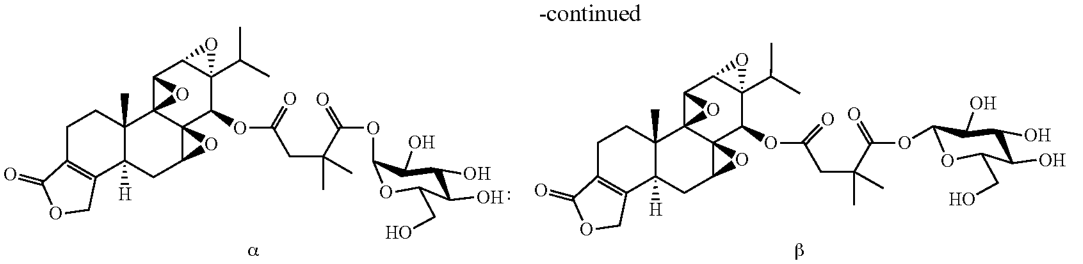

= 1.1:1.0

α β

Compound 2

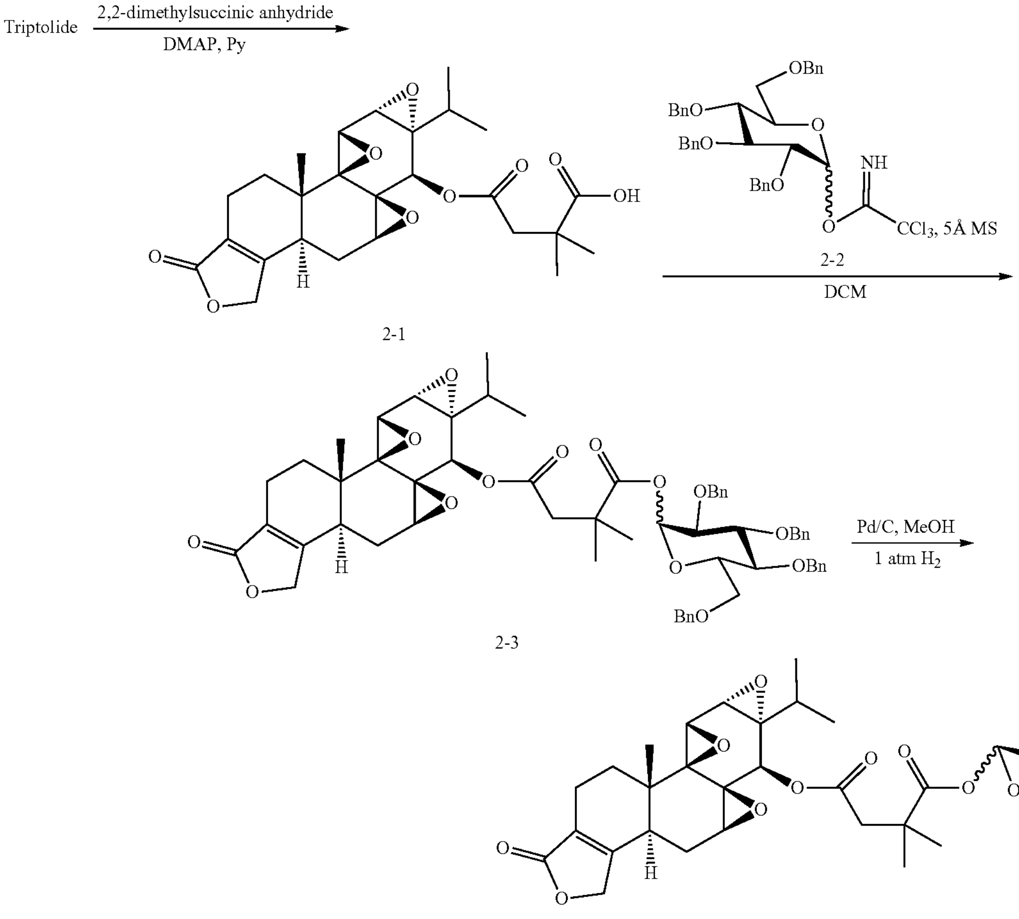

2-1

2-3

(α:β = 1.1:1.0)
compound 2

To a solution of Triptolide (200 mg, 0.56 mmol) in pyridine (4 mL) were added 2,2-dimethylsuccinic anhydride (285 mg, 2.22 mmol) and DMAP (14 mg, 0.11 mmol). After stirring overnight, the mixture was diluted with ethyl acetate, then washed with saturated copper sulfate, water and brine, respectively. The organic layers were dried over $Na_2SO_4$ and filtered. The filtrate was concentrated using a rotary evaporator to give a residue. The residue was purified by silica gel column chromatography ($CH_2Cl_2/CH_3OH$, 15:1) to give intermediate 2-1 (215 mg, 0.44 mmol, 80%) as a white solid; $^1H$ NMR (400 MHz, $CDCl_3$) δ 5.07 (s, 1H), 4.68 (s, 2H), 3.81 (d, J=3.1 Hz, 1H), 3.53 (d, J=2.7 Hz, 1H), 3.45 (d, J=5.6 Hz, 1H), 2.71 (dd, J=23.2, 7.1 Hz, 4H), 2.32 (d, J=16.4 Hz, 1H), 2.15 (ddd, J=25.7, 15.9, 10.0 Hz, 2H), 2.00-1.81 (m, 2H), 1.37 (s, 3H), 1.35 (s, 3H), 1.23 (dt, J=11.6, 7.9 Hz, 3H), 1.05 (s, 3H), 0.94 (d, J=6.9 Hz, 3H), 0.82 (d, J=6.9 Hz, 3H); ESI-MS (m z): 511.3 $[M+Na]^+$.

Trichloroacetimidate donor 2-2 (100 mg, 0.15 mmol) and acid intermediate 2-1 (49 mg, 0.1 mmol) were dissolved in $CH_2Cl_2$ (2 mL) under nitrogen. Powdered freshly activated 5 Å molecular sieves (200 mg) were added. Stirring was continued until TLC indicated the disappearance of the donor (about 8 h). The mixture was filtered through Celite, and the filtrated was concentrated in vacuum. The residue was purified by silica gel column chromatography (petroleum ether/EtOAc, 2:1 to 1:1) to give the intermediate product 2-3 (48 mg, 0.047 mmol, a/b=1.1: 1.0, 47%) as a white solid.

Palladium on charcoal (10%, 10 mg) was added to a solution of intermediate 2-3 (22 mg, 0.022 mmol) in $CH_3OH$. The mixture was placed under an atmosphere of hydrogen for about 4 h. The mixture was filtered and concentrated. The residue was purified by silica gel column chromatography ($CH_2Cl_2/CH_3OH$, 15:1) to give the product compound 2 (10 mg, 0.015 mmol, a/b=1.0: 1.0, 71%) as a white solid; $^1H$ NMR (400 MHz, $CD_3OD$) δ 6.11 (d, J=3.7 Hz, 0.5H), 5.45 (d, J=7.7 Hz, 0.5H), 5.07 (d, J=4.3 Hz, 1H), 4.80 (dd, J=19.6, 10.1 Hz, 2H), 3.96 (d, J=3.0 Hz, 1H), 3.84 (d, J=11.2 Hz, 1H), 3.80-3.59 (m, 4H), 3.56 (dd, J=9.8, 3.7 Hz, 1H), 3.51-3.33 (m, 4H), 2.76 (p, J=15.9 Hz, 3H), 2.33-2.16 (m, 2H), 2.02 (d, J=47.8 Hz, 1H), 1.90 (ddt, J=11.6, 9.3, 7.6 Hz, 2H), 1.50 (dd, J=12.5, 4.6 Hz, 1H), 1.35 (d, J=5.8 Hz, 6H), 1.03 (s, 3H), 0.94 (dd, J=7.0, 2.0 Hz, 3H), 0.84 (d, J=6.9 Hz, 3H); ESI-MS m z calcd for $C_{32}H_{42}O_{14}Na$ $[M+Na]^+$ 673.2467, found 673.2466.
Example 3
Synthesis of Compound 3
Scheme 4. Synthesis of compound 3.
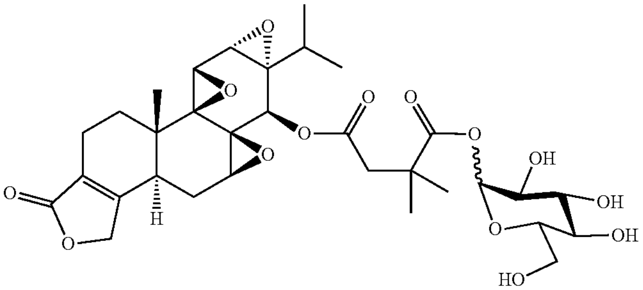
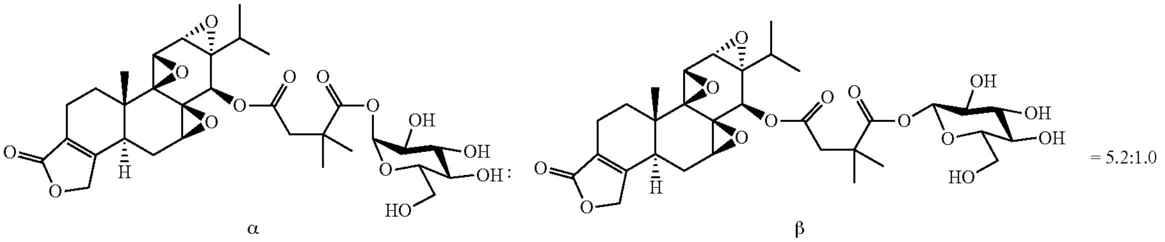
α β
Compound 3
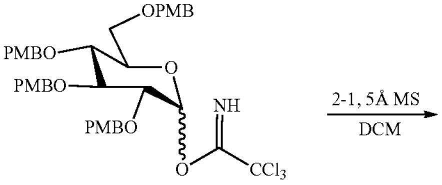
10-4
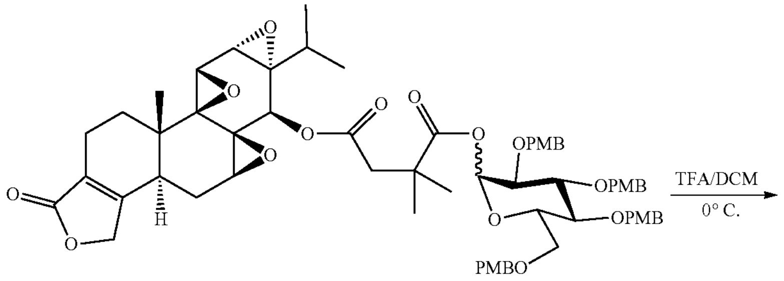
3-1
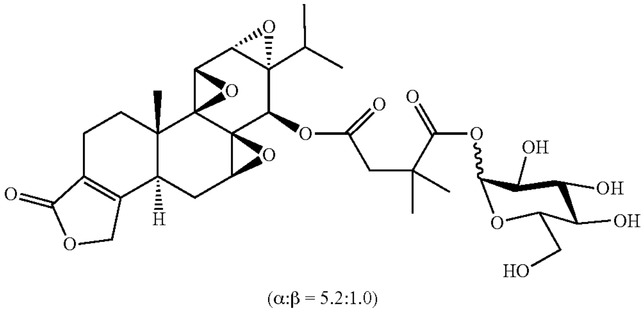
(α:β = 5.2:1.0)
compound 3

Trichloroacetimidate donor intermediate 10-4 (see example 10) (371 mg, 0.46 mmol) and acid intermediate 2-1 (150 mg, 0.31 mmol) were dissolved in $CH_2Cl_2$ (6 mL) under nitrogen. Powdered freshly activated 5 Å molecular sieves (600 mg) were added. Stirring was continued until TLC indicated the disappearance of the donor (about 8 h). The mixture was filtered through Celite, and the filtrated was concentrated in vacuum. The residue was purified by silica gel column chromatography (petroleum ether/EtOAc, 2:1 to 1:1) to give the intermediate product 3-1 (180 mg, 0.16 mmol, a/b=6.6:1.0, 52%) as a white solid. $^1H$ NMR (400 MHz, $CDCl_3$) δ 7.24 (dd, J=5.7, 2.8 Hz, 6H), 7.03 (d, J=8.6 Hz, 3H), 6.89-6.70 (m, 10H), 6.37 (d, J=3.5 Hz, 1H), 5.02 (d, J=0.9 Hz, 1H), 4.86 (d, J=10.6 Hz, 1H), 4.73 (dd, J=10.3, 2.89-2.64 (m, 3H), 2.21 (tt, J=16.9, 4.6 Hz, 2H), 2.03 (t, J=13.4 Hz, 1H), 1.93-1.76 (m, 2H), 1.45 (dd, J=12.7, 5.3 Hz, 1H), 1.32 (d, J=5.4 Hz, 7H), 0.99 (s, 3H), 0.89 (d, J=6.9 Hz, 3H), 0.79 (d, J=6.8 Hz, 3H); $^{13}C$ NMR (126 MHz, $CD_3OD$) δ 177.13, 176.06, 172.35, 163.93, 125.43, 93.92, 75.92, 74.90, 72.96, 72.51, 71.99, 70.80, 64.83, 64.10, 62.82, 62.05, 61.04, 56.68, 56.14, 49.85, 44.78, 42.35, 41.38, 36.75, 30.71, 29.31, 25.63, 25.26, 24.12, 17.91, 17.85, 17.14, 14.16; ESI-MS (m z): 673.6 [M+Na]; ESI-MS m z calcd for $C_{32}H_{42}O_{14}Na$ $[M+Na]^+$ 673.2467, found 673.2466.

Example 4

Synthesis of Compound 4

Compound 4

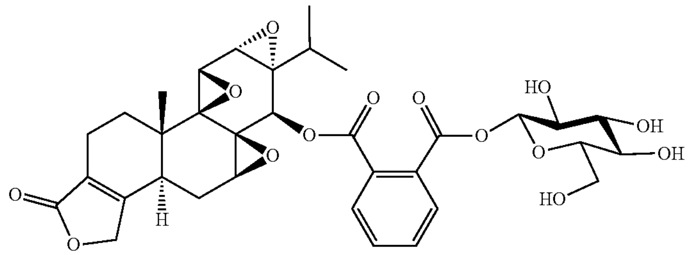

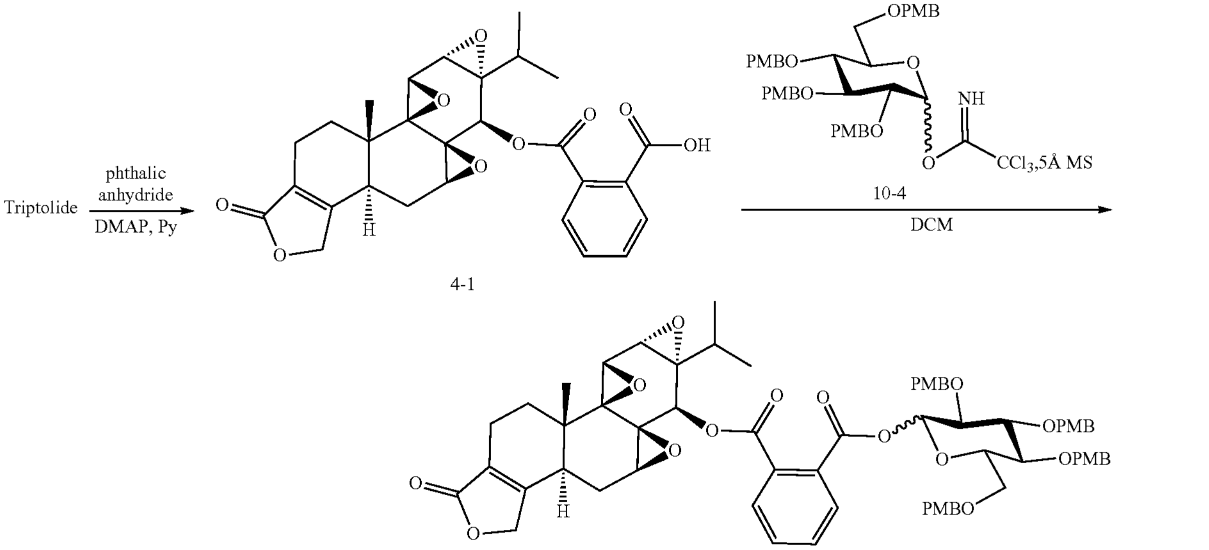

4-1

4-2

7.6 Hz, 2H), 4.66-4.43 (m, 6H), 4.39 (dd, J=11.1, 4.5 Hz, 2H), 3.83-3.72 (m, 18H), 3.71-3.62 (m, 4H), 3.62-3.52 (m, 2H), 3.51-3.39 (m, 1H), 3.30 (d, J=5.5 Hz, 1H), 1.35 (d, J=5.1 Hz, 7H), 1.00 (s, 3H), 0.92 (d, J=6.9 Hz, 4H), 0.79 (d, J=6.9 Hz, 4H); ESI-MS m z calcd for $C_{64}H_{74}O_{18}Na$ $[M+Na]^+$ 1153.4767, found 1153.4781.

Intermediate 3-1 (148 mg, 0.13 mmol) was dissolved in DCM (5 mL), and cooled to 0° C. Then TFA (0.5 mL) was added. After stirring at this temperature for about 10 min, the reaction mixture was concentrated in vacuo. The residue was chromatographed over silica gel (DCM/Methanol=10:1) to yield the product as compound 3 (77 mg, 0.12 mmol, a/b=5.2:1.0, 91%) as a white solid. $^1H$ NMR (500 MHz, $CD_3OD$) δ 6.08 (d, J=3.6 Hz, 1H), 5.42 (d, J=7.9 Hz, 0H), 5.02 (d, J=4.6 Hz, 1H), 4.86-4.68 (m, 2H), 4.01-3.85 (m, 1H), 3.79-3.51 (m, 5H), 3.43 (dd, J=12.2, 7.4 Hz, 2H), To a solution of Triptolide (200 mg, 0.56 mmol) in pyridine (4 mL) were added phthalic anhydride (285 mg, 2.22 mmol) and DMAP (14 mg, 0.11 mmol). After stirring overnight, the mixture was diluted with ethyl acetate, then washed with saturated copper sulfate, water and brine, respectively. The organic layers were dried over $Na_2SO_4$ and filtered. The filtrate was concentrated using a rotary evaporator to give a residue. The residue was purified by silica gel column chromatography ($CH_2Cl_2/CH_3OH$, 15:1) to give intermediate compound 4-1 (260 mg, 0.51 mmol, 91%) as a white solid; $^1H$ NMR (400 MHz, $CD_3Cl$) δ 5.07 (s, 1H), 4.68 (s, 2H), 3.81 (d, J=3.1 Hz, 1H), 3.53 (d, J=2.7 Hz, 1H), 3.45 (d, J=5.6 Hz, 1H), 2.71 (dd, J=23.2, 7.1 Hz, 4H), 2.32 (d, J=16.4 Hz, 1H), 2.15 (ddd, J=25.7, 15.9, 10.0 Hz, 2H), 2.00-1.81 (m, 2H), 1.37 (s, 3H), 1.35 (s, 3H), 1.23 (dt, J=11.6, 7.9 Hz, 3H), 1.05 (s, 3H), 0.94 (d, J=6.9 Hz, 3H), 0.82 (d, J=6.9 Hz, 3H); ESI-MS (m z): 511.3 $[M+Na]^+$.

Trichloroacetimidate donor intermediate 10-4 (see example 10) (618 mg, 0.77 mmol) and acid intermediate 4-1 (260 mg, 0.51 mmol) were dissolved in $CH_2Cl_2$ (10 mL) under nitrogen. Powdered freshly activated 5 Å molecular sieves (900 mg) were added. Stirring was continued until TLC indicated the disappearance of the donor (about 8 h). The mixture was filtered through Celite, and the filtrated was concentrated in vacuum. The residue was purified by silica gel column chromatography (petroleum ether/EtOAc, 2:1 to 1:1) to give the intermediate products 4-2α (75 mg, 0.065 mmol, 13%) and 4-2β (225 mg, 0.195 mmol, 39%) as a white solid.

Intermediate 4-2α: $^{1}H$ NMR (400 MHz, $CDCl_3$) δ 7.92 (dd, J=7.5, 1.4 Hz, 1H), 7.69 (dd, J=7.6, 1.4 Hz, 1H), 7.62-7.50 (m, 2H), 7.35-7.23 (m, 6H), 7.06-7.00 (m, 2H), 6.91-6.77 (m, 8H), 6.53 (d, J=3.5 Hz, 1H), 5.28 (s, 1H), 4.86 (d, J=10.6 Hz, 1H), 4.78-4.54 (m, 9H), 4.40 (dd, J=11.0, 8.4 Hz, 2H), 3.97-3.86 (m, 2H), 3.83-3.67 (m, 21H), 3.61 (dd, J=10.8, 2.0 Hz, 1H), 3.54 (d, J=3.1 Hz, 1H), 3.46 (d, J=5.6 Hz, 1H), 2.68 (d, J=12.9 Hz, 1H), 2.31 (d, J=17.6 Hz, 1H), 2.19 (ddd, J=24.9, 12.5, 6.3 Hz, 4H), 1.90-1.79 (m, 1H), 1.54 (dd, J=12.1, 5.4 Hz, 1H), 1.06 (s, 3H), 1.01 (d, J=6.9 Hz, 3H), 0.81 (d, J=6.9 Hz, 3H); $^{13}C$ NMR (100 MHz, $CDCl_3$) δ 173.37, 166.23, 165.61, 160.19, 159.44, 159.40, 159.28, 131.78, 131.64, 131.47, 131.03, 130.42, 130.11, 130.02, 129.79, 129.74, 129.72, 129.67, 129.19, 125.63, 113.92, 113.90, 113.87, 91.22, 81.48, 78.70, 77.36, 76.60, 75.38, 75.03, 73.25, 72.72, 72.27, 70.08, 67.60, 63.70, 61.21, 60.50, 60.06, 55.60, 55.38, 55.34, 55.02, 40.47, 35.76, 29.97, 27.36, 23.53, 21.17, 17.58, 17.16, 16.76, 14.31, 13.88; ESI-MS m z calcd for $C_{66}H_{70}O_{18}Na$ $[M+Na]^+$ 1173.4454, found 1173.4466.

Intermediate 4-2β: $^{1}H$ NMR (400 MHz, $CDCl_3$) δ 7.77 (dd, J=7.8, 1.2 Hz, 1H), 7.63 (dd, J=7.8, 1.3 Hz, 1H), 7.52 (td, J=7.6, 1.3 Hz, 1H), 7.42 (td, J=7.6, 1.3 Hz, 1H), 7.21-7.11 (m, 5H), 7.11-7.04 (m, 2H), 7.03-6.96 (m, 2H), 6.80-6.63 (m, 9H), 5.77-5.70 (m, 1H), 5.22 (s, 1H), 4.77-4.45 (m, 9H), 4.37 (dd, J=12.9, 11.0 Hz, 2H), 3.73 (d, J=3.2 Hz, 1H), 3.71 (s, 3H), 3.69 (s, 3H), 3.67 (s, 3H), 3.65 (s, 3H), 3.63 (q, J=5.4, 4.2 Hz, 5H), 3.55-3.48 (m, 1H), 3.46 (d, J=3.0 Hz, 1H), 3.40 (d, J=5.5 Hz, 1H), 2.56 (d, J=12.7 Hz, 1H), 2.20 (d, J=17.8 Hz, 1H), 2.15-1.91 (m, 3H), 1.77 (t, J=14.0 Hz, 1H), 1.45 (dd, J=12.4, 5.3 Hz, 1H), 1.10 (td, J=12.3, 5.8 Hz, 1H), 0.97 (s, 3H), 0.93 (d, J=6.9 Hz, 3H), 0.73 (d, J=6.9 Hz, 3H); $^{13}C$ NMR (100 MHz, $CDCl_3$) δ 173.30, 166.56, 164.77, 160.22, 159.30, 159.22, 132.90, 132.04, 130.97, 130.66, 130.30, 130.26, 130.20, 130.18, 129.76, 129.73, 129.66, 129.56, 129.51, 129.45, 129.24, 125.43, 113.80, 113.77, 94.88, 84.68, 80.50, 77.01, 75.81, 75.24, 74.59, 74.51, 73.15, 72.16, 70.02, 67.75, 63.61, 63.57, 61.29, 60.02, 55.56, 55.29, 55.24, 55.21, 54.89, 40.33, 35.65, 29.85, 27.33, 23.36, 17.54, 17.06, 16.81, 13.80; ESI-MS m z calcd for $C_{66}H_{70}O_{18}Na$ $[M+Na]^+$ 1173.4454, found 1173.4466.

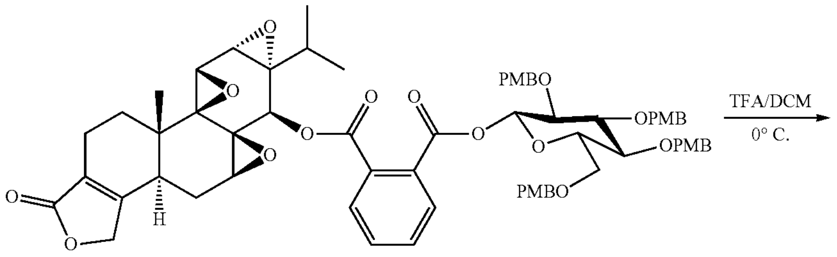

4-2β

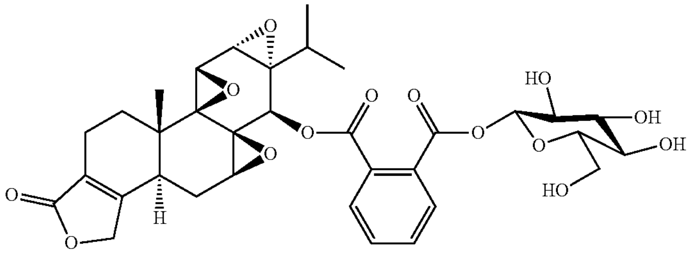

compound 4

Compound 4: Intermediate 4-2β (118 mg, 0.10 mmol) was dissolved in DCM (5 mL), and cooled to 0° C. Then TFA (0.5 mL) was added. After stirring at this temperature for about 10 min, the reaction mixture was concentrated in vacuo. The residue was chromatographed over silica gel (DCM/Methanol=10:1) to yield the product compound 4 (55 mg, 80%) as a white solid. $^{1}H$ NMR (400 MHz, $CD_3OD$) δ 8.05-7.57 (m, 4H), 5.72 (d, J=7.7 Hz, 1H), 5.29 (d, J=1.0 Hz, 1H), 4.85-4.69 (m, 2H), 4.01 (d, J=3.2 Hz, 1H), 3.88 (dd, J=12.2, 2.2 Hz, 1H), 3.76-3.67 (m, 2H), 3.58 (d, J=5.6 Hz, 1H), 3.54-3.37 (m, 4H), 2.87-2.71 (m, 1H), 2.36-1.98 (m, 4H), 1.57-1.43 (m, 1H), 1.33 (ddd, J=17.0, 11.4, 4.9 Hz, 1H), 1.06 (s, 3H), 1.03 (d, J=6.8 Hz, 3H), 0.86 (d, J=6.9 Hz, 3H); $^{13}C$ NMR (100 MHz, $CD_3OD$) δ 184.70, 176.86, 175.66, 172.48, 142.00, 141.68, 141.49, 141.09, 139.42, 139.36, 134.12, 105.44, 87.66, 86.46, 83.20, 82.88, 80.62, 79.63, 73.61, 72.96, 71.45, 71.02, 70.16, 65.58, 64.91, 50.00, 45.41, 39.42, 37.60, 32.78, 26.61, 26.49, 25.84, 22.88; ESI-MS m z calcd for $C_{34}H_{38}O_{14}Na$ $[M+Na]^+$ 693.2154, found 693.2143.

Example 5
Synthesis of Compound 5
Scheme 5. Synthesis of compound 5.
Compound 5
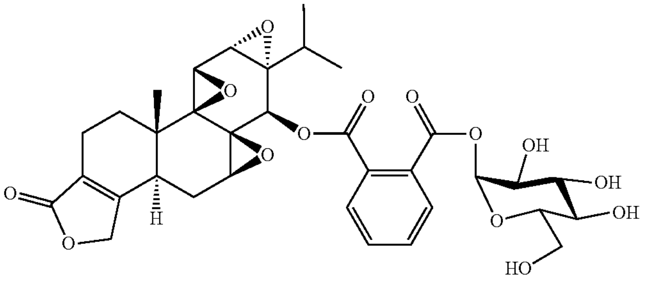
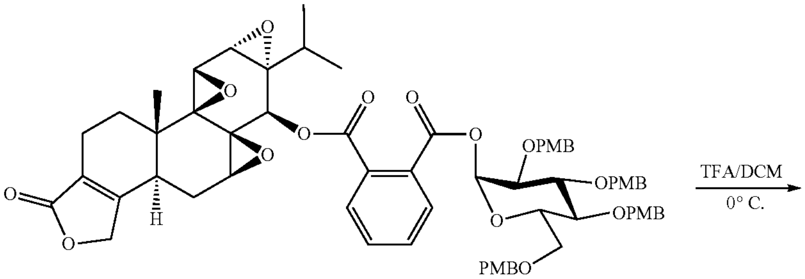
4-2α
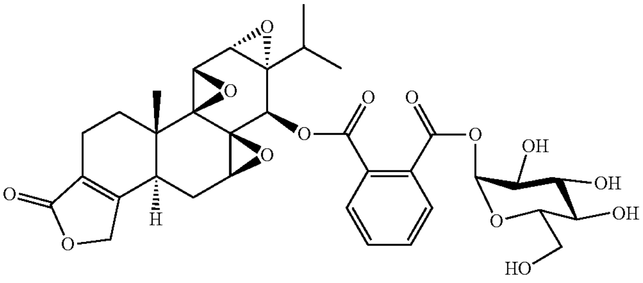
compound 5

Intermediate compound 4-2α (50 mg, 0.043 mmol) was dissolved in DCM (2 mL), and cooled to 0° C. Then TFA (0.2 mL) was added. After stirring at this temperature for about 10 min, the reaction mixture was concentrated in vacuo. The residue was chromatographed over silica gel (DCM/Methanol=10:1) to yield the product compound 5 (24 mg, 83%) as a white solid. $^1H$ NMR (400 MHz, $CD_3OD$) δ 8.14-7.51 (m, 4H), 6.38 (d, J=3.7 Hz, 1H), 5.27 (d, J=0.9 Hz, 1H), 4.86-4.70 (m, 2H), 4.00 (d, J=3.1 Hz, 1H), 3.93-3.71 (m, 3H), 3.71-3.67 (m, 1H), 3.66 (d, J=3.7 Hz, 1H), 3.58 (d, J=5.6 Hz, 1H), 3.48 (s, 1H), 2.78 (d, J=12.3 Hz, 1H), 2.33-2.18 (m, 2H), 2.10 (q, J=6.9 Hz, 1H), 1.99-1.87 (m, 1H), 1.56-1.46 (m, 1H), 1.39-1.27 (m, 2H), 1.04 (s, 3H), 1.00 (d, J=6.9 Hz, 3H), 0.86 (d, J=6.9 Hz, 3H); $^{13}C$ NMR (100 MHz, $CD_3OD$) δ 176.08, 167.95, 167.72, 163.89, 133.99, 133.20, 132.53, 132.10, 130.94, 130.25, 125.48, 94.92, 76.28, 74.86, 74.50, 72.61, 71.99, 70.83, 64.95, 64.33, 62.89, 62.11, 61.52, 56.89, 56.28, 41.41, 36.79, 30.80, 29.13, 24.15, 17.98, 17.89, 17.23, 14.23; ESI-MS m z calcd for $C_{34}H_{38}O_{14}Na$ $[M+Na]^+$ 693.2154, found 693.2143.

Example 6

Synthesis of Compound 6

To a solution of Triptolide (50 mg, 0.14 mmol) in pyridine (2 mL) were added glutaric anhydride (63 mg, 4 mmol) and DMAP (24 mg, 0.556 mmol). After stirring overnight, the mixture was diluted with ethyl acetate, then washed with saturated copper sulfate, water and brine, respectively. The organic layers were dried over $Na_2SO_4$ and filtered. The filtrate was concentrated using a rotary evaporator. The residue was purified by silica gel column chromatography ($CH_2Cl_2$/$CH_3OH$, 15:1) to give the intermediate product 6-1 (48 mg, 0.10 mmol, 73%) as a white solid; $^1H$ NMR (400 MHz, $CDCl_3$) δ 5.08 (s, 1H), 4.67 (s, 2H), 3.83 (d, J=3.1 Hz, 1H), 3.53 (d, J=2.7 Hz, 1H), 3.47 (d, J=5.6 Hz, 1H), 2.68 (d, J=13.1 Hz, 1H), 2.61-1.81 (m, 14H), 1.04 (s, 3H), 0.95 (d, J=7.0 Hz, 3H), 0.84 (d, J=6.9 Hz, 3H); ESI-MS (m z): 497.3 $[M+Na]^+$.

Trichloroacetimidate donor intermediate 2-2 (103 mg, 0.15 mmol) and acid intermediate 6-1 (48 mg, 0.1 mmol) were dissolved in $CH_2Cl_2$ (2 mL) under nitrogen. Powdered freshly activated 5 Å molecular sieves (200 mg) were added. Stirring was continued until TLC indicated the disappearance of the donor (about 8 h). The mixture was filtered through Celite, and the filtrated was concentrated in vacuum. The residue was purified by silica gel column chromatography (petroleum ether/EtOAc, 1:1) to give the intermediate Compound 6

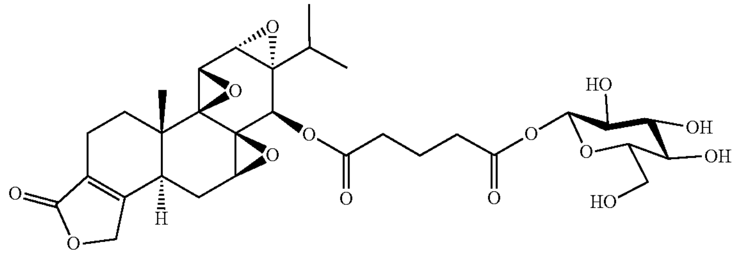

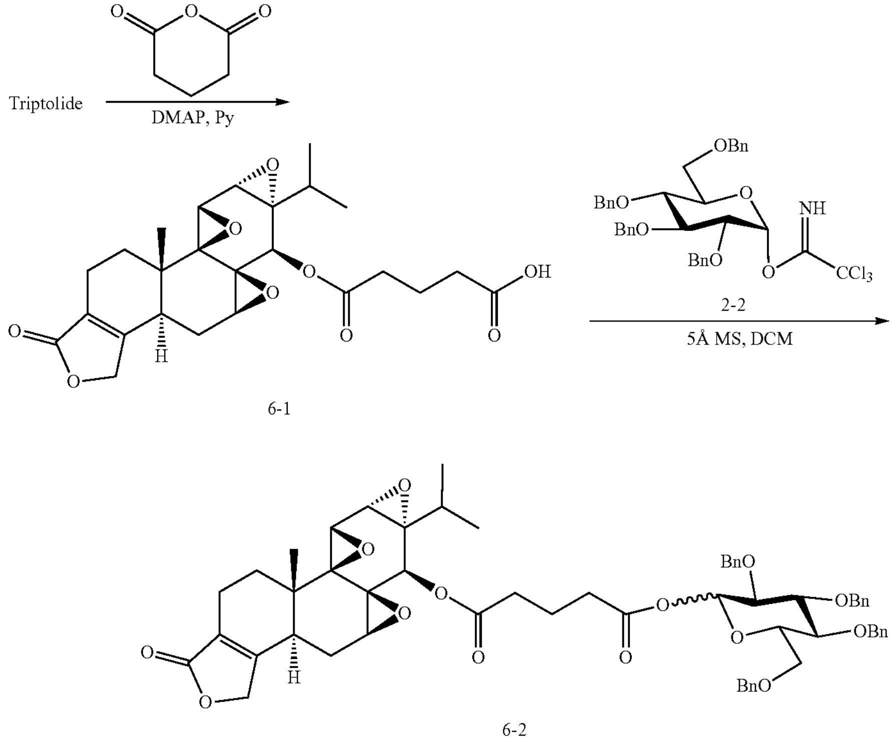

6-1

6-2 products 6-2α (12 mg, 0.012 mmol, 12%) and 6-2β (15 mg, 0.015 mmol, 15%) as a white solid.

Intermediate 6-2α: $^1$H NMR (400 MHz, $CDCl_3$) δ 7.43-7.00 (m, 21H), 6.39 (d, J=3.4 Hz, 1H), 5.08 (s, 1H), 4.96 (d, J=10.9 Hz, 1H), 4.82 (t, J=10.2 Hz, 2H), 4.76-4.41 (m, 7H), 4.02-3.81 (m, 2H), 3.81-3.56 (m, 5H), 3.45 (dd, J=14.9, 4.1 Hz, 2H), 2.63 (d, J=13.1 Hz, 1H), 2.52 (dt, J=17.8, 7.2 Hz, 4H), 2.33-2.17 (m, 1H), 2.17-1.92 (m, 4H), 1.92-1.73 (m, 2H), 1.67-1.44 (m, 2H), 1.34-1.05 (m, 3H), 1.00 (s, 3H), 0.94 (d, J=7.0 Hz, 3H), 0.81 (d, J=6.9 Hz, 3H); ESI-MS m/z calcd for $C_{59}H_{64}O_{14}Na$ $[M+Na]^+$ 1019.4188, found 1019.4183.

Intermediate 6-2β: $^1$H NMR (400 MHz, $CDCl_3$) δ 7.43-7.04 (m, 21H), 5.61 (d, J=8.1 Hz, 1H), 5.08 (s, 1H), 4.79 (d, J=24.9 Hz, 5H), 4.63 (d, J=12.1 Hz, 5H), 3.73 (s, 5H), 3.67-3.52 (m, 2H), 3.48 (d, J=3.0 Hz, 1H), 3.44 (d, J=5.5 Hz, 1H), 2.65 (d, J=13.3 Hz, 1H), 2.59-2.22 (m, 5H), 2.04 (s, 7H), 1.66-1.47 (m, 2H), 1.33-1.12 (m, 3H), 1.01 (s, 3H), 0.94 (d, J=7.0 Hz, 3H), 0.82 (d, J=6.9 Hz, 3H); ESI-MS m/z calcd for $C_{59}H_{64}O_{14}Na$ $[M+Na]^+$ 1019.4188, found 1019.4183.

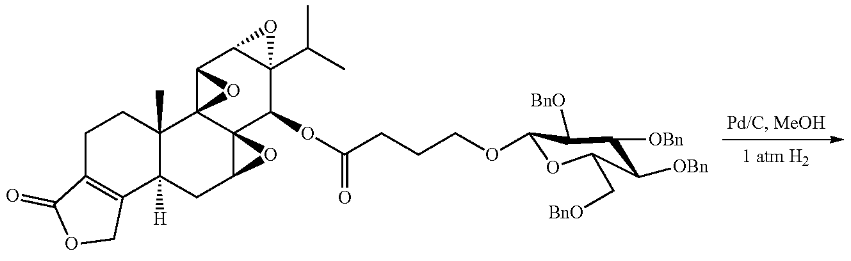

6-2β

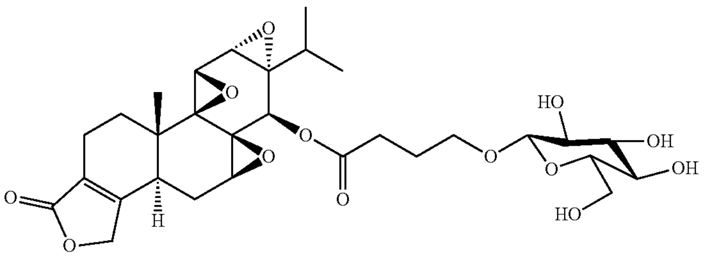

compound 6

Compound 6: Palladium on charcoal (10%, 5 mg) was added to a solution of intermediate compound 6-2β (10 mg, 0.010 mmol) in $CH_3OH$. The mixture was placed under an atmosphere of hydrogen for about 4 h. The mixture was filtered and concentrated. The residue was purified by silica gel column chromatography ($CH_2Cl_2/CH_3OH$, 15:1) to give compound 6 (5 mg, 0.008 mmol, 82%) as a white solid; $^1$H NMR (400 MHz, $CD_3OD$) δ 5.49 (d, J=8.1 Hz, 1H), 5.09 (s, 1H), 4.83-4.78 (m, 1H), 3.96 (d, J=3.2 Hz, 1H), 3.83 (dd, J=12.1, 1.7 Hz, 1H), 3.70-3.57 (m, 2H), 3.48 (d, J=5.6 Hz, 1H), 3.45-3.35 (m, 3H), 2.78 (d, J=15.3 Hz, 1H), 2.60-2.42 (m, 4H), 2.27 (dt, J=15.0, 5.9 Hz, 2H), 2.15-1.81 (m, 5H), 1.51 (dd, J=12.7, 4.5 Hz, 1H), 1.39-1.19 (m, 3H), 1.04 (s, 2H), 0.95 (d, J=7.0 Hz, 2H), 0.85 (d, J=7.0 Hz, 3H); $^{13}$C NMR (100 MHz, $CD_3OD$) δ 176.11, 173.91, 173.68, 163.89, 125.54, 93.47, 75.99, 74.81, 72.77, 72.30, 71.99, 70.98, 64.92, 64.15, 62.84, 62.27, 61.15, 56.79, 56.24, 41.45, 36.83, 34.17, 33.87, 30.79, 29.62, 24.17, 21.28, 17.95, 17.11, 14.25; ESI-MS (m/z): 659.5 $[M+Na]^+$.

Example 7

Synthesis of Compound 7

Scheme 6. Synthesis of compound 7.

Compound 7

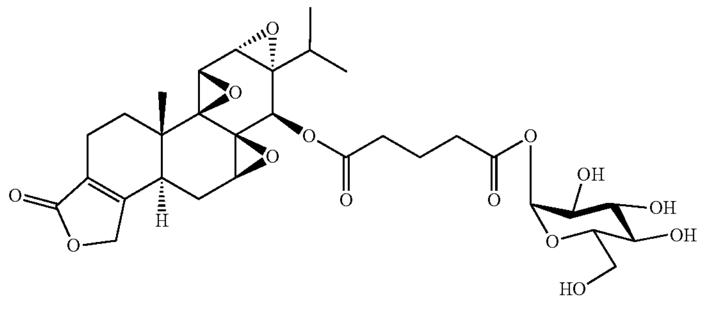

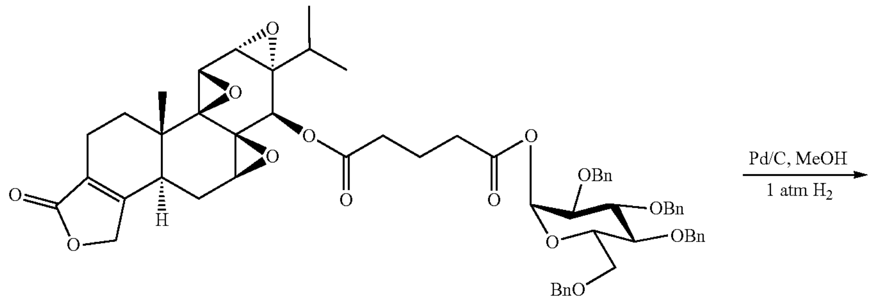

6-2α

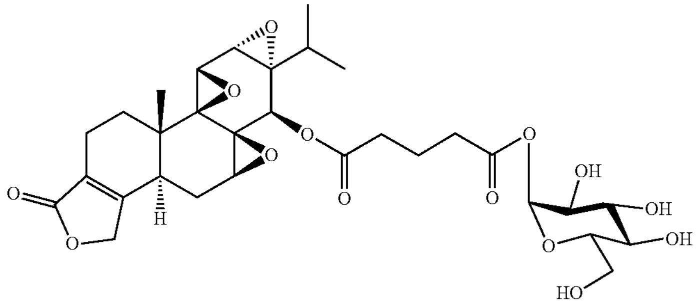

compound 7

Compound 7: Palladium on charcoal (10%, 5 mg) was added to a solution of intermediate compound 6-2α (10 mg, 0.01 mmol) in $CH_3OH$. The mixture was placed under an atmosphere of hydrogen for about 4 h. The mixture was filtered and concentrated. The residue was purified by silica gel column chromatography ($CH_2Cl_2/CH_3OH$, 15:1) to give the product compound 7 (5 mg, 0.008 mmol, 82%) as a white solid; $^1H$ NMR (400 MHz, $CD_3OD$) δ 6.04 (d, J=3.7 Hz, 1H), 4.99 (s, 1H), 4.73-4.68 (m, 2H), 3.86 (d, J=3.1 Hz, 1H), 3.70-3.63 (m, 1H), 3.62-3.51 (m, 4H), 3.45 (dd, J=9.7, 3.8 Hz, 1H), 3.38 (d, J=5.6 Hz, 1H), 3.33-3.24 (m, 2H), 2.76-2.29 (m, 6H), 2.22-2.09 (m, 2H), 2.06-1.72 (m, 6H), 1.46-1.38 (m, 1H), 0.95 (s, 3H), 0.85 (d, J=7.0 Hz, 3H), 0.75 (d, J=7.0 Hz, 3H); $^{13}C$ NMR (100 MHz, $CD_3OD$) δ 176.11, 173.91, 173.68, 163.89, 125.54, 93.47, 75.99, 74.81, 72.77, 72.30, 71.99, 70.98, 64.92, 64.15, 62.84, 62.27, 61.15, 56.79, 56.24, 41.45, 36.83, 34.17, 33.87, 30.79, 29.62, 24.17, 21.28, 17.95, 17.11, 14.25; ESI-MS (m/z): 659.5 $[M+Na]^+$.

Example 8

Synthesis of Compound 8

Scheme 7. Synthesis of compound 8.

Compound 8

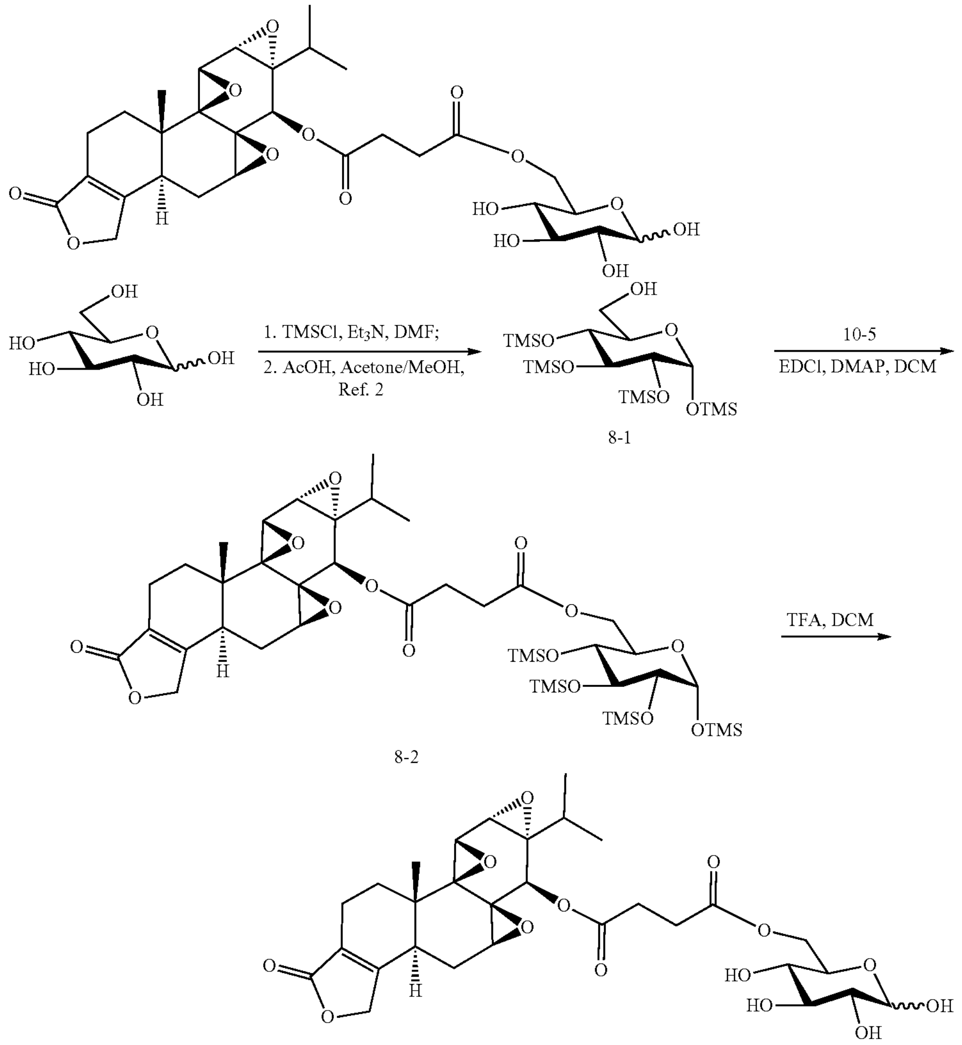

compound 8

A solution of acid intermediate 10-5 (60 mg, 0.13 mmol), intermediate compound 8-1 (92 mg, 0.20 mmol), DMAP (cat.), and EDCI (50 mg, 0.26 mmol) in $CH_2Cl_2$ (4 mL) was stirred for 8 h at RT. The resulting mixture was diluted with $CH_2Cl_2$, then washed with water and brine, respectively. The organic layers were dried over $Na_2SO_4$ and filtered. The filtrate was concentrated in vacuo. The residue was purified by silica gel column chromatography (petroleum ether/EtOAc, 3:2) to give intermediate compound 8-2 (97 mg, 0.11 mmol, 82%) as white solid. $^1$H NMR (500 MHz, $CDCl_3$) δ 5.04 (d, J=0.9 Hz, 1H), 4.96 (d, J=3.0 Hz, 1H), 4.63 (s, 2H), 4.32 (dd, J=11.8, 2.3 Hz, 1H), 4.01 (dd, J=11.8, 5.4 Hz, 1H), 3.86 (ddd, J=9.8, 5.3, 2.2 Hz, 1H), 3.78 (d, J=3.2 Hz, 1H), 3.74 (t, J=8.8 Hz, 1H), 3.49 (dd, J=3.1, 0.9 Hz, 1H), 3.41 (d, J=5.8 Hz, 1H), 3.40-3.36 (m, 1H), 3.32 (dd, J=9.1, 3.0 Hz, 1H), 2.80-2.60 (m, 5H), 2.31-2.02 (m, 4H), 1.93-1.81 (m, 2H), 1.52 (dd, J=11.9, 5.8 Hz, 1H), 1.01 (s, 3H), 0.90 (d, J=6.9 Hz, 3H), 0.79 (d, J=6.9 Hz, 3H), 0.11 (s, 3H), 0.11 (s, 3H), 0.10 (s, 3H), 0.09 (s, 3H); $^{13}$C NMR (125 MHz, $CDCl_3$) δ 173.25, 172.00, 171.70, 160.11, 125.54, 93.91, 73.93, 73.84, 72.38, 71.23, 70.02, 69.91, 64.16, 63.52, 63.35, 61.19, 59.70, 55.36, 55.02, 40.38, 35.69, 29.86, 29.14, 29.00, 27.99, 23.46, 17.53, 17.09, 16.74, 13.79, 1.27, 0.96, 0.48, 0.17; ESI-MS m z calcd for $C_{42}H_{70}O_{14}NaSi$ $[M+Na]^+$ 933.3735, found 933.3740.

Intermediate compound 8-2 (25 mg, 0.027 mmol) was dissolved in DCM (1.5 mL), and cooled to 0° C. Then TFA (0.15 mL) was added. After stirring at this temperature for about 45 min, the reaction mixture was concentrated in vacuo. The residue was chromatographed over silica gel (DCM/Methanol=10:1) to yield the product compound 8 (15 mg, 0.024 mmol, 89%) as a white solid. $^1$H NMR (500 MHz, $CD_3OD$) δ 5.51 (s, 0.37H), 5.11 (d, J=3.7 Hz, 0.66H), 5.09 (d, J=1.1 Hz, 1H), 4.86-4.76 (m, 2H), 4.50 (d, J=7.8 Hz, 0.33H), 4.49-4.43 (m, 0.32H), 4.39 (dd, J=11.7, 2.2 Hz, 0.63H), 4.29-4.17 (m, 1H), 4.03-3.98 (m, 0.57H), 3.98 (dd, J=3.3, 1.2 Hz, 1H), 3.69 (t, J=9.3 Hz, 0.62H), 3.65 (td, J=3.5, 1.0 Hz, 1H), 3.52 (ddd, J=9.5, 6.1, 2.1 Hz, 0.35H), 3.48 (d, J=5.7 Hz, 1H), 3.37 (s, 1H), 3.31-3.26 (m, 1.45H), 3.16 (dd, J=9.0, 7.8 Hz, 032H), 2.84-2.76 (m, 1H), 2.76-2.65 (m, 4H), 2.27 (ddt, J=17.0, 11.0, 5.7 Hz, 2H), 2.16-2.04 (m, 1H), 1.99-1.85 (m, 2H), 1.53 (ddd, J=12.5, 5.6, 1.5 Hz, 1H), 1.34 (ddd, J=21.7, 10.8, 5.2 Hz, 2H), 1.26 (t, J=7.1 Hz, 0H), 1.06 (s, 3H), 0.96 (d, J=7.0 Hz, 3H), 0.85 (d, J=6.9 Hz, 3H); $^{13}C$ NMR (100 MHz, $CD_3OD$) δ 176.10, 173.92, 173.85, 173.35, 173.31, 163.91, 125.50, 98.22, 93.96, 77.93, 76.16, 75.31, 74.73, 73.73, 73.06, 73.05, 72.00, 71.96, 71.71, 70.60, 65.35, 65.27, 64.87, 64.27, 62.70, 61.00, 56.74, 56.18, 41.45, 36.79, 30.82, 30.06, 29.84, 29.82, 29.11, 24.16, 17.91, 17.87, 17.08, 14.21, 14.19; ESI-MS m z calcd for $C_{30}H_{39}O_{14}Na$ $[M+Na]^+$ 645.2154, found 645.2159.

Example 9

Synthesis of Compound 9

A solution of acid intermediate 10-5 (25 mg, 0.054 mmol), intermediate compound 9-1 (50 mg, 0.11 mmol), DMAP (2 mg, 0.011 mmol), and DCC (22 mg, 0.11 mmol) in $CH_2Cl_2$ (2 mL) was stirred for 8 h at RT. The resulting mixture was diluted with $CH_2Cl_2$, then washed with water and brine, respectively. The organic layers were dried over $Na_2SO_4$ and filtered. The filtrate was concentrated in vacuo. The residue was purified by silica gel column chromatography (petroleum ether/EtOAc, 3:2) to give the intermediate product 9-2 (41 mg, 0.045 mmol, 83%) as a white solid: $^1H$ NMR (500 MHz, $CDCl_3$) δ 7.46-7.13 (m, 13H), 5.04 (s, 1H), 4.99 (d, J=10.8 Hz, 1H), 4.86 (d, J=10.8 Hz, 1H), 4.82 (d, J=10.8 Hz, 1H), 4.78 (d, J=12.1 Hz, 1H), 4.70-4.53 (m, 5H), 4.35 (dd, J=11.9, 4.5 Hz, 1H), 4.26 (dd, J=11.9, 2.1 Hz, 1H), 3.99 (t, J=9.2 Hz, 1H), 3.84-3.75 (m, 2H), 3.54 (dd, J=9.6, 3.6 Hz, 1H), 3.51-3.45 (m, 2H), 3.39 (d, J=5.6 Hz, 1H), 3.36 (s, 3H), 2.30 (d, J=15.1 Hz, 1H), 1.54 (dd, J=12.5, 4.7 Hz, 1H), 1.02 (s, 3H), 0.90 (d, J=7.0 Hz, 3H), 0.80 (d, J=6.9 Hz, 3H); $^{13}C$ NMR (125 MHz, $CDCl_3$) δ 173.32, 171.95, Scheme 8. Synthesis of compound 9.

Compound 9

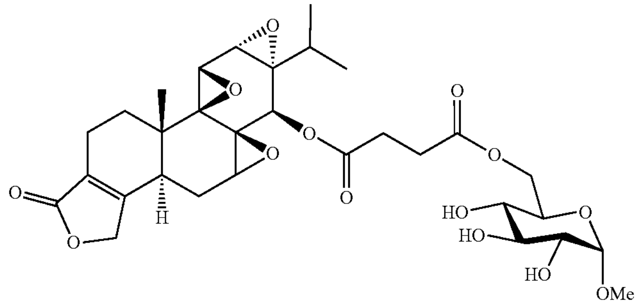

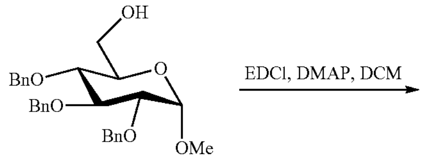

9-1

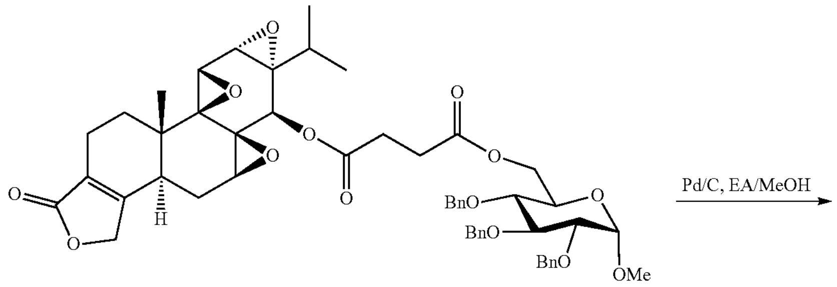

9-2

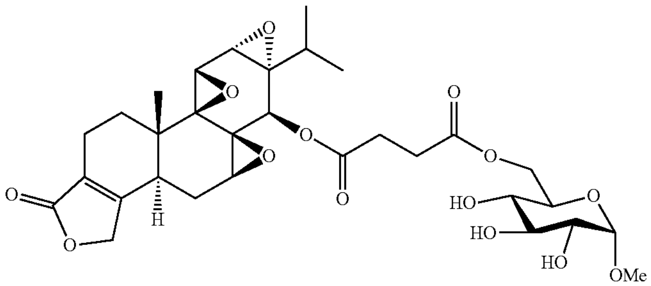

compound 9

171.77, 160.05, 138.75, 138.16, 128.61, 128.55, 128.24, 128.18, 128.12, 128.10, 127.98, 127.80, 125.70, 98.19, 82.16, 80.03, 77.47, 75.95, 75.19, 73.52, 71.34, 70.06, 68.70, 63.62, 63.42, 63.35, 61.30, 59.76, 55.47, 55.38, 55.10, 40.46, 35.77, 29.96, 29.16, 29.03, 28.16, 23.51, 17.58, 17.18, 16.81, 13.88; ESI-MS (m z): 930.4 [M+Na]$^+$.

Palladium on charcoal (10%, 10 mg) was added to a solution of intermediate compound 9-2 (17 mg, 0.019 mmol) in $CH_3OH$. The mixture was placed under an atmosphere of hydrogen for about 14 h. The mixture was filtered and concentrated. The residue was purified by silica gel column chromatography ($CH_2Cl_2$/$CH_3OH$, 15:1) to give compound 9 (7 mg, 0.011 mmol, 60%) as a white solid: $^1$H NMR (400 MHz, $CD_3OD$) δ 5.07 (s, 1H), 4.87-4.72 (m, 2H), 4.65 (d, J=3.7 Hz, 1H), 4.41 (dd, J=11.7, 2.0 Hz, 1H), 4.26-4.14 (m, 1H), 3.96 (d, J=3.2 Hz, 1H), 3.80-3.69 (m, 1H), 3.63 (d, J=3.0 Hz, 1H), 3.60 (d, J=9.2 Hz, 1H), 3.46 (d, J=5.6 Hz, 1H), 3.45-3.38 (m, 4H), 2.71 (t, J=3.6 Hz, 6H), 2.37-1.83 (m, 5H), 1.04 (s, 3H), 0.94 (d, J=7.0 Hz, 3H), 0.83 (d, J=6.9 Hz, 3H); $^{13}$C NMR (100 MHz, $CD_3OD$) δ 176.08, 173.82, 173.27, 163.89, 125.51, 101.25, 75.04, 73.45, 73.07, 71.98, 71.89, 71.02, 65.23, 64.87, 64.27, 62.69, 61.00, 56.73, 56.19, 55.63, 41.46, 36.80, 30.83, 30.09, 29.86, 29.10, 24.17, 17.92, 17.87, 17.08, 14.19; ESI-MS (m z): 659.6 [M+Na]$^+$.

Example 10

Synthesis of Compound 10

Scheme 9. Synthesis of compound 10.

Compound 10

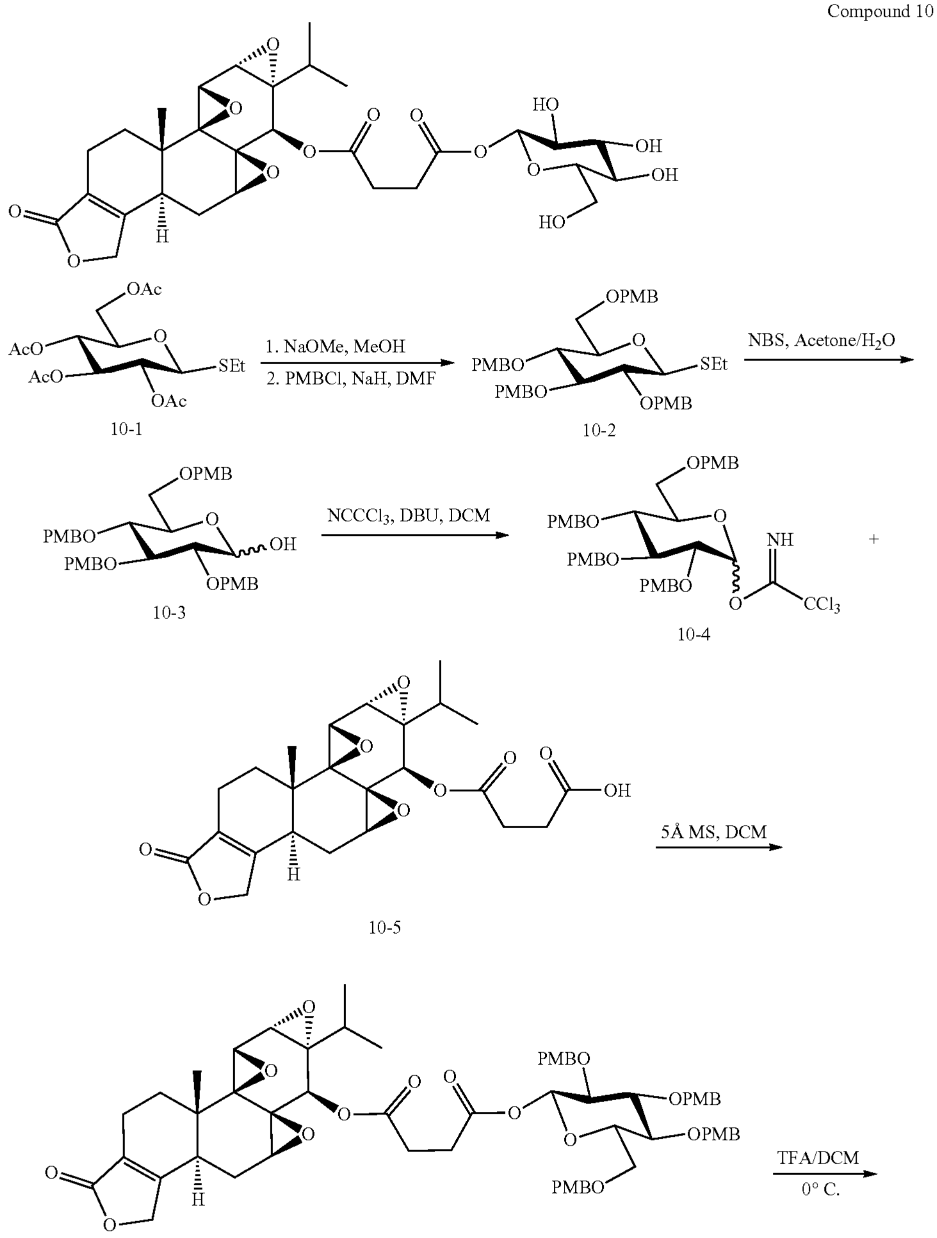

10-1

10-2

10-3

10-4

10-5

10-6

-continued

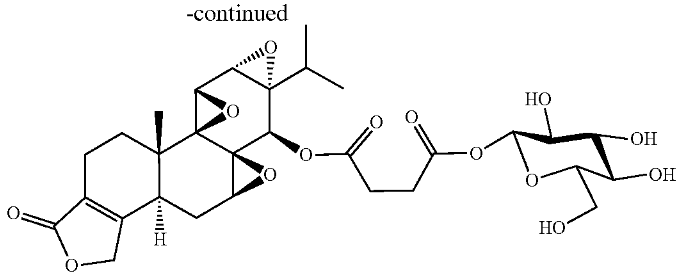

compound 10

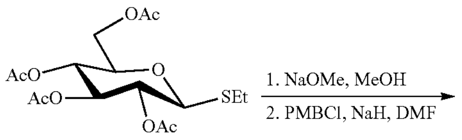

10-1

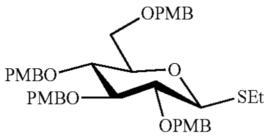

10-2

Intermediate 10-2: To a solution of intermediate 10-1 (see Das et al. (1996) *J. Am. Chem. Soc.* 296:275-77; Barry et al. (2013) *J. Am. Chem. Soc.* 135:16895-903.) (2.1 g, 5.3 mmol) in methanol (20 mL), was added NaOMe (29 mg, 0.5 mmol). Stirring was continued until complete conversion of the starting material (monitored by TLC, about 2 hours). The mixture was neutralized with acidic resin, filtered and concentrated. Then the mixture was coevaporated with toluene three times and dried in vacuo.

The mixture was dissolved in dry DMF (27 mL), and cooled to 0° C. NaH (1.28 g, 60% suspension, 32.1 mmol) was added slowly over 5 min. After 10 min, PMBCl (5.8 mL, 42.8 mmol) was added and the reaction stirred for another 10 min, at which time the temperature was raised to room temperature for 4 h. The reaction was re-cooled to 0° C. and water was added to quench the reaction. The organic layer was diluted with ethyl acetate, and washed twice with water, once with brine, dried over $Na_2SO_4$. Then, the mixture was filtered and concentrated. Column chromatography (Petroleum ether/Ethyl acetate=4/1) afforded the intermediate product 10-2 as a white solid (3.4 g, 4.8 mmol, 91% for two steps); $^1H$ NMR (400 MHz, $CDCl_3$) δ 7.43-7.26 (m, 6H), 7.11-7.03 (m, 2H), 6.91-6.79 (m, 8H), 4.90-4.41 (m, 9H), 3.84-3.78 (m, 13H), 3.72-3.59 (m, 3H), 3.54 (dd, J=10.0, 8.5 Hz, 1H), 3.47-3.36 (m, 2H), 2.87-2.68 (m, 2H), 1.33 (t, J=7.4 Hz, 3H); $^{13}C$ NMR (100 MHz, $CDCl_3$) δ 159.45, 159.39, 159.29, 159.28, 130.93, 130.37, 130.10, 129.75, 129.56, 129.49, 113.96, 113.93, 113.90, 113.85, 86.53, 85.21, 81.63, 79.23, 77.85, 77.37, 75.52, 75.24, 74.79, 73.16, 68.84, 55.39, 25.16, 15.32; ESI-MS m z calcd for $C_{40}H_{48}O_9Na$ $[M+Na]^+$ 727.2911, found 727.2919.

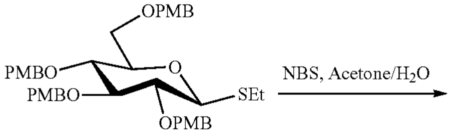

10-2

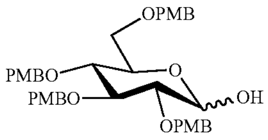

10-3

Intermediate 10-3: The thioglycoside intermediate 10-2 (3.0 g, 4.25 mmol) was dissolved in acetone (50 mL) and water (5 mL), and cooled to 0° C. N-bromosuccinimide (1.9 g, 10.7 mmol) was added which produced a bright orange color. Stirring was continued at 0° C. until TLC indicated disappearance of the starting material (about 1 h). The reaction was concentrated, then dissolved in ethyl acetate and washed with water and brine. The organic layers were dried over $Na_2SO_4$. Then, the mixture was filtered and concentrated. Column chromatography (Petroleum ether/Ethyl acetate=2/1 to 1/1) afforded the intermediate product 10-3 as a white solid (1.95 g, 3.0 mmol, 71%). ESI-MS (m z): 683.6 $[M+Na]^+$.

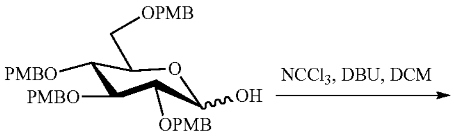

10-3

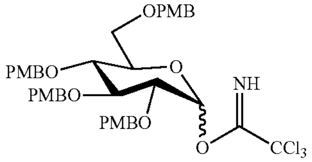

10-4

Intermediate 10-4: The lactol intermediate 10-3 (380 mg, 0.58) was dissolved in $CH_2Cl_2$ (5 mL) and cooled to 0° C. Trichloroacetonitrile (0.3 mL, 2.88 mmol) and DBU (cat.) were added successively. After stirring at room temperature for about 2 h, the reaction mixture was concentrated in vacuo. The residue was chromatographed over silica gel (Petroleum ether/EtOAc=4:1, containing 1% $Et_3N$) to yield imidate intermediate 10-4 (400 mg, 86%) as a colorless oil. $^1H$ NMR (400 MHz, $CDCl_3$) δ 8.57 (s, 1H), 7.42-6.69 (m, 16H), 6.47 (d, J=3.4 Hz, 1H), 4.87 (d, J=10.6 Hz, 1H), 4.79-4.71 (m, 2H), 4.66 (d, J=11.3 Hz, 1H), 4.60 (d, J=11.3 Hz, 1H), 4.56 (d, J=11.7 Hz, 1H), 4.40 (d, J=2.9 Hz, 1H), 4.37 (d, J=4.4 Hz, 1H), 4.03-3.89 (m, 2H), 3.80 (s, 3H), 3.79 (s, 3H), 3.78 (s, 3H), 3.76 (s, 3H), 3.75-3.66 (m, 3H), 3.60 (dd, J=10.8, 2.1 Hz, 1H).

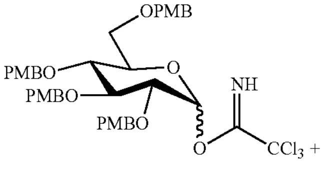

10-4

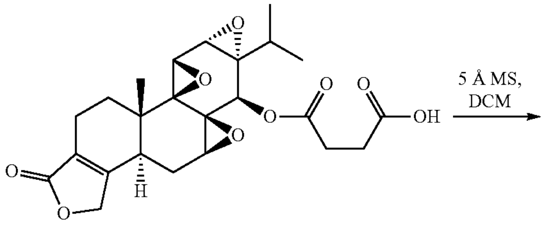

10-5

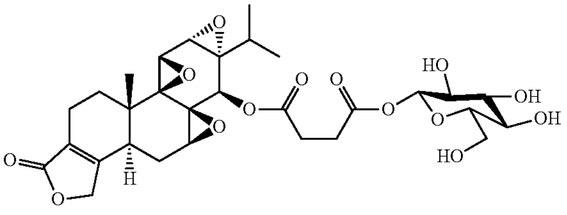

10-6

Intermediate 10-3: Trichloroacetimidate donor intermediate 10-4 (2.7 g, 3.35 mmol) and acid intermediate 10-5 (1.03 g, 2.24 mmol) were dissolved in $CH_2Cl_2$ (100 mL) under nitrogen. Powdered freshly activated 5 Å molecular sieves (200 mg) were added. Stirring was continued until TLC indicated the disappearance of the donor (about 8 h). The mixture was filtered through Celite, and the filtrated was concentrated in vacuum. The residue was purified by silica gel column chromatography (petroleum ether/EtOAc, 1:1) to give intermediate compound 10-6 (2.43 g, 2.2 mmol, 98%) as a white solid. $^1H$ NMR (400 MHz, $CDCl_3$) δ 7.42-6.71 (m, 16H), 5.58 (d, J=8.0 Hz, 1H), 5.08 (s, 1H), 4.93-4.50 (m, 9H), 4.46-4.26 (m, 2H), 3.74-3.26 (m, 10H), 2.72 (m, 6H), 1.04 (s, 3H), 0.95 (d, J=7.0 Hz, 3H), 0.83 (d, J=6.9 Hz, 3H); $^{13}C$ NMR (100 MHz, $CDCl_3$) δ 173.43, 171.55, 170.70, 160.18, 159.36, 159.29, 130.72, 130.37, 130.27, 130.03, 129.81, 129.67, 129.62, 129.56, 125.66, 113.90, 113.86, 94.49, 84.57, 80.68, 75.60, 75.44, 74.70, 73.17, 71.44, 70.11, 67.65, 63.61, 63.41, 61.28, 59.72, 55.45, 55.37, 55.32, 55.08, 40.44, 35.74, 29.90, 29.22, 28.95, 28.00, 23.50, 17.58, 17.13, 16.79, 13.85; ESI-MS m z calcd for $C_{62}H_{70}O_{18}Na$ $[M+Na]^+$ 1125.4454, found 1125.4471.

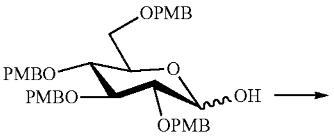

10-7

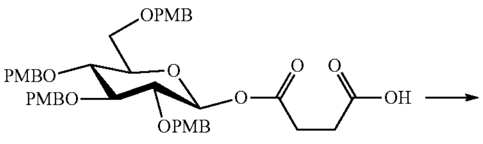

10-8

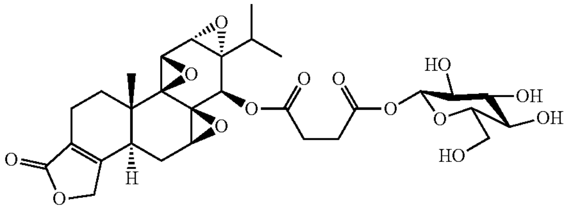

10-6

Alternative route to synthesize intermediate 10-6: Tetra-O-para-methoxybenzyl-glucose intermediate 10-7 (1.32 g, 2.0 mmol) and succinic anhydride (800 mg, 8.0 mmol) were dissolved in toluene (40 mL) under nitrogen. After stirring for 15 min, NaH (120 mg, 3.0 mmol) was added. Stirring was continued until TLC indicated the disappearance of the donor (about 8 h). The mixture was filtered through Celite, and the filtrated was concentrated in vacuum. The residue was purified by silica gel column chromatography (petroleum ether/EtOAc, 1:1) to give intermediate compound 10-8 (1.48 g, 1.96 mmol, 98%) as a white solid.

Acid intermediate 10-8 (1.14 g, 1.5 mmol) and Triptolide (360 mg, 1.0 mmol) were dissolved in $CH_2Cl_2$ (15 mL) under nitrogen. Powdered freshly activated 5 Å molecular sieves (2 g) were added. Stirring was continued until TLC indicated the disappearance of the donor (about 6 h). The mixture was filtered through Celite, and the filtrated was concentrated in vacuum. The residue was purified by silica gel column chromatography (petroleum ether/EtOAc, 1:1) to give intermediate compound 10-6 (938 mg, 0.85 mmol, 85%) as a white solid

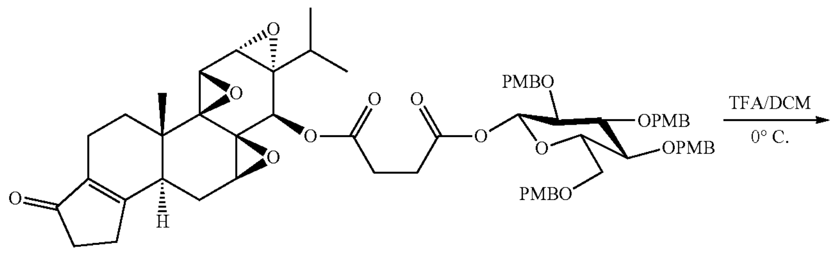

10-6

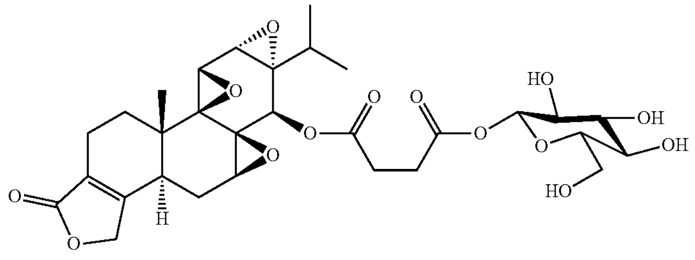

compound 10

Compound 10: Intermediate compound 10-6 (2.0 g, 1.81 mmol) was dissolved in DCM (36.0 mL), and cooled to 0° C. Then TFA (3.6 mL) was added. After stirring at this temperature for about 10 min, the reaction mixture was concentrated in vacuo. The residue was chromatographed over silica gel (DCM/Methanol=10:1) to yield the product compound 10 (1.1 g, 1.77 mmol, 98%) as a white solid. $^1$H NMR (500 MHz, $CD_3OD$) δ 5.54-5.43 (d, J=8.0, 1H), 5.08 (s, 1H), 3.97 (d, J=3.1 Hz, 1H), 3.90-3.77 (m, 1H), 3.68 (dd, J=12.0, 4.4 Hz, 1H), 3.64 (d, J=2.7 Hz, 1H), 3.48 (d, J=5.7 Hz, 1H), 3.46-3.35 (m, 4H), 2.85-2.67 (m, 4H), 2.39-2.18 (m, 2H), 2.07 (m, 1H), 1.91 (m, 2H), 1.50 (dd, J=12.4, 4.9 Hz, 1H), 1.34 (td, J=12.1, 5.8 Hz, 1H), 1.03 (s, 3H), 0.93 (d, J=7.0 Hz, 3H), 0.84 (d, J=6.9 Hz, 3H); $^{13}$C NMR (125 MHz, $CD_3OD$) δ 176.01, 173.23, 172.72, 163.85, 125.46, 111.34, 95.88, 78.72, 77.83, 73.91, 73.05, 71.98, 70.97, 64.90, 64.26, 62.72, 62.28, 61.00, 56.76, 56.15, 41.41, 36.76, 30.79, 29.87, 29.77, 29.16, 24.12, 17.92, 17.13, 14.24; ESI-MS m z calcd for $C_{30}H_{38}O_{14}Na$ $[M+Na]^+$ 645.2154, found 645.2166.

Example 11

Testing of the Glucose-Triptolide Conjugates

Cells and culture conditions. Primary astrocytes (Lonza, Walkersville, MD; ABM™ Basal Media with AGM™ SingleQuots™ Supplement Pack), fibroblast (ATCC; Fibroblast Basal Medium (ATCC© PCS-201-030™) with Fibroblast Growth Kit-Serum-free (ATCC© PCS-201-040™)), airway epithelial cell (ATCC; Airway Epithelial Cell Basal Medium (ATCC© PCS-300-030™) with Bronchial Epithelial Cell Growth Kit (ATCC© PCS-300-040™)), renal proximal tubule (ATCC; Renal Epithelial Cell Basal Medium (ATCC© PCS-400-030™) with Renal Epithelial Cell Growth Kit (ATCC© PCS-400-040™)), prostate epithelial cell (Lonza; PrEGM™ BulletKit™) and mammary epithelial cell (Lonza; MEBM™ BulletKit™) were kept in a humidified incubator at 37° C. adjusted to 5% $CO_2$. Prostate (PC3, LNCaP, DU-145), breast (MDA-MB-231, MDA-MB-453, SK-BR-3), head and neck (A253, Detroit 562, SCC-25), melanoma (SK-Mel-3, SK-Mel-1, RPMI-7951), pancreatic (CfPAC-1, BxPC3, SW1990), lung (A549, NCI-H1299, NCI-H1437) and liver (SNU-475, SK-HEP-1, SNU-387) cancer cell lines were obtained from ATCC and cultured in their respective media (prostate cells: RPMI-1640, MDA-MB-231: RPMI-1640, MDA-MB-453: Leibovitz's L-15, SK-BR-3: McCoy's 5a, A253: McCoy's 5a, Detroit 562: EMEM, SCC-25: DMEM, SK-Mel-3: McCoy's 5a, SK-Mel-1: EMEM, RPMI-7951: EMEM), CfPAC-1: IMDM, BxPC3: RPMI-1640, SW1990: Leibovitz's L-15), A549: F-12K, NCI-H1299: RPMI-1640, NCI-H1437: RPMI-1640, SNU-475: RPMI-1640, SK-HEP-1: EMEM, SNU-387: RPMI-1640. All media were supplemented with 10% (vol/vol) filtered fetal bovine serum (FBS, Invitrogen, Carlsbad, CA), 1% penicillin/streptomycin (Invitrogen) and maintained in a humidified incubator at 37° C. with 5% $CO_2$ except for MDA-MB-453 and SW1990 grown at 37° C. without $CO_2$ control. Wild type (ATCC) and C342T XPB knock-in cells (named T7115) of Human Embryonic Kidney 293T (HEK293T), HeLa (ATCC) were cultured in DMEM (GIBCO) with 10% (vol/vol) filtered fetal bovine serum (FBS, Invitrogen, Carlsbad, CA), 1% penicillin/streptomycin (Invitrogen).

In vivo tumor xenograft assay. Animal experiments were performed following the protocols approved by the Johns Hopkins University Animal Care and Use Committee. The experimental murine model of human prostate cancer metastasis used in this study was generated as previously described. (Bhatnagar et al. (2014) *Cancer Res.* 74:5772-81) Briefly, four- to six-week-old, male NOD/SCID/IL2R$^{\gamma}$null (NSG, purchased from Animal Resources Core, JHU) were injected with a million PC3/ML/fluc cells via tail vein. Tumor formation was confirmed by bioluminescence imaging (BLI) using the IVIS Spectrum Imaging System (Caliper Life Sciences, Hopkinton, MA) three weeks after injection and the mice were given indicated doses of drug once daily (intraperitoneal injection) for 30 days. Tumor progression was then monitored weekly by BLI and survival monitored concurrently.

Reagents. Triptolide and WZB117 were purchased from Sigma while spironolactone was obtained from Acros Organics. Doxorubicin was from APExBio.

Proliferation and viability assays. [$^3$H]-thymidine incorporation. HEK293T cells (10,000 cells/well) were seeded into 96-well plates then cultured in DMEM plus 10% FBS and 1% penicillin/streptomycin at 37° C. with 5% $CO_2$ overnight. Drugs were added at indicated concentrations and incubation was continued for an additional 24 h. For hypoxia, PC3 (5,000 cells/well) were exposed to 1% $O_2$ (Airgas) in a humidified hypoxia chamber (Billups-Rothenberg) in 37° C. for 48 h prior to drug exposure for 48 h. Treated cells were then pulsed using an aliquot of 1 μCi of [$^3$H]-thymidine (Perkin Elmer) per well for an additional 6 h. Radiolabelled cells were harvested onto a printed Filtermat A glass fiber filter (Perkin Elmer) using a Tomtec Harvester 96 Mach III M. Betaplate Scint (Perkin Elmer) scintillation fluid was added to radiolabelled filters followed by scintillation counting on Microbeta2 LumiJET Microplate Counter (Perkin Elmer).

XTT assay. Five thousand cells/well were plated on flat-bottom, transparent 96-well plate in a full growth media and incubated at appropriate culture conditions. Twenty four hours after seeding, cells were treated with indicated drugs and incubated for 47 hrs. Cell viability was measured using the R&D Systemsm TACS XTT Cell Proliferation/Viability Assay (R&D Systems, Minneapolis, MN).

ATPase activity assay. The TFIIH complex was purified and its DNA-dependent ATPase assay was performed as previously described (Titov et al. (2011) *Nat. Chem. Biol.* 7:182-88). Briefly, a 10-μl reaction mixture contained 20 mM Tris (pH 7.9), 4 mM MgCl2, 1 μM of ATP, 0.1 μCi [$^{\gamma\text{-}32}$P]ATP (3000 Ci/mmol), 100 μg/ml BSA, 100 nM RNA Polymerase II promoter positive control DNA, 1 nM TFIIH and indicated concentrations of triptolide or its analogs. The reactions were started by either addition of TFIIH for 2 hr and stopped by addition of 2 μl of 0.5 M EDTA. An aliquot of 1 μl reaction mixture was spotted on PEI-cellulose (sigma) and the chromatogram was developed with 0.5 M LiCi and 1 M HCOOH. The percent of ATP hydrolysis was quantified using a Typhoon FLA 9500 Variable Imager (GE Healthcare).

Stability of glutriptolides in human serum. Human serum (Sigma, 10% in DMEM media) was treated with 10 μM drug (triptolide or glutriptolides) at room temperature for various time points. The incubation was stopped by placing samples on dry ice followed by overnight storage in −80° C. Frozen samples were then lyophilized and reconstituted in DMSO at room temperature for an hour. Samples were centrifuged at 12,000 RPM for 10 minutes and supernatants loaded into an HPLC-MS with the following conditions: (Varian pursuit XR5 Diphenyl 150×4.6 mm; A phase: Millipore water with 0.1% HCOOH; B phase: Acetonitrile with 0.1% HCOOH; 0-6 min: 95% B; 6-24 min: 5% B-100% B; 24-28 min: 100% B; 28-29 min: 100% B5% B; 29-30 min: 5% B).

Western blot analysis. Whole cell lysates were prepared by adding lysis buffer [4% SDS, 20% glycerol, 10% 2-mercaptoethanol, 0.004% bromophenol blue, 0.125 M Tris-HCl (pH 6.8)] to the cell pellets for 30 minutes in ice followed by centrifugation at 12,000×g for 10 minutes then boiling for 5 minutes. For isolation of cytosolic and mitochondrial fractions of cytochrome C, cell pellets were resuspended in CLAMI buffer (250 mM sucrose, 70 mM KCl, 50 mg/ml digitonin in 1×PBS, protease inhibitor cocktail (1 tablet/10 ml CLAMI buffer)) then incubated on ice for 5 minutes. After centrifugation at 12,000×g for 5 minutes at 4° C., supernatant (cytoplasmic fraction) was collected and the pellet resuspended in lysis buffer as described above. Proteins were then separated by SDS-PAGE and transferred to nitrocellulose membranes (Bio-Rad). After blocking at room temperature for 1 h, membranes were incubated at 4'C overnight with the primary antibodies including anti-Rpb1 (Santa Cruz Biotechnology), anti-XPB (Biotechne), anti-Actin (Developmental Studies Hybridoma Bank), anti-GAPDH (Santa Cruz Biotechnology), anti-cytochrome C (Santa Cruz Biotechnology), anti-PARP1 (Santa Cruz Biotechnology), anti-cleaved caspase 3 (Cell Signaling Technology), anti-VDAC (ProteinTech), anti-HIF-1□ (BD sciences), and anti-GLUT1 (Santa Cruz Biotechnology) antibodies followed by incubation with horseradish peroxidase-conjugated anti-mouse or anti-rabbit IgG (GE Healthcare) at room temperature for 2 hours. Antibody-protein complexes were detected using enhanced chemiluminescence (ECL) immunoblotting detection reagent (EMD Millipore).

Immunocytochemistry and cytochemistry. HeLa or PC3 cells (2×10$^5$) were seeded on a MatTek glass bottom culture dish (Fisher Scientific, Pittsburgh, PA, USA) and allowed to adhere for 24 h. Cells were then treated with either DMSO or drugs for 6 or 24 h then fixed with 4% paraformaldehyde, permeabilized using 1×PBS with 0.5% triton X 100 then probed for endogenous RNA Polymerase II catalytic subunit Rpb1 or HIF-1α using anti-RNAPII (Santa Cruz Biotechnology) and anti-HIF-1α (BD sciences) antibodies, respectively. Detection was then done using anti-mouse Alexa Fluor 488 (Invitrogen). For nuclear staining, fixed and permeabilized cells were incubated in DAPI (ThermoFisher) or Hoechst 33258 (Sigma) for 30 minutes prior to imaging. Glucose uptake was monitored by incubating cells in 200 μM 2-NBDG (ThermoFisher) for 6 hours prior to fixation. Fluorescence was observed under the Nikon Eclipse TE200 Inverted microscope (Nikon Instruments Inc., Melville, NY, USA). ImageJ software (NIH, Bethesda, MD, USA; http://imagej.nih.gov/ij/index.html) was used to measure intracellular protein levels in immuno-cytochemistry samples (Li et al. (2015) *Toxicological Sciences: an Official Journal of the Society of Toxicology* 143:196-208). Rpb1 levels were measured using the MEASURE feature of ImageJ where all the background signals were subtracted from the intergrated density of nuclear Rpb1.

Quantification and statistical analysis. Data fitting for dose curves was performed using GraphPad Prism for Mac, GraphPad Softward (www.graphpad.com). Statistical values were reported in the Figures and Tables. Results are presented as mean with SEM unless otherwise specified and statistical significance was determined using two-tailed Student's t-test (unequal variance). Survival curves were estimated using Kaplan-Meier method and chi-square testing was used to determine significant differences among groups as previously described (Sullivan et al. (2017) *Essentials of Biostatistics for Public Health* 3rd Edition, Johnes and Bartlett publishers).

TABLE 3

Anti-proliferative activities of the disclosed compounds against HEK 293T cells.

| Compounds | IC50 ± SEM (nM) |
|---|---|
| TPL | 5.6 ± 0.415 |
| Compound 1 | 71 ± 1.07 |
| Compound 2 | 3305 ± 0.98 |
| Compound 3 | 999 ± 0.217 |
| Compound 4 | 5888 ± 1.19 |
| Compound 5 | 6667 ± 2.03 |
| Compound 6 | 1134 ± 1.15 |
| Compound 7 | 735 ± 1.11 |
| Compound 8 | 244 ± 0.81 |

TABLE 3-continued

Anti-proliferative activities of the disclosed compounds against HEK 293T cells.

| Compounds | IC50 ± SEM (nM) |
|---|---|
| Compound 9 | 395 ± 0.523 |
| Compound 10 | 279 ± 0.611 |

Table 3 shows the anti-proliferative activities against HEK 293T cells for triptolide (TPL) and the disclosed glucose-conjugated triptolides.

Those skilled in the art will recognize, or be able to ascertain, using no more than routine experimentation, numerous equivalents to the specific composition and procedures described herein. Such equivalents are considered to be within the scope of this disclosure, and are covered by the following claims.

What is claimed is:

1. A compound of the structure of Formula (I):

Formula (I)

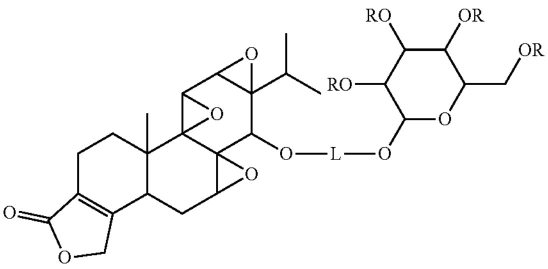

or a pharmaceutically acceptable salt, a stereoisomer, a diastereoisomer or an enantiomer thereof, wherein each R is independently selected from the group consisting of hydrogen, alkyl, and acetyl group;

L is selected from $-CO(CR_1R_2)_n-$,

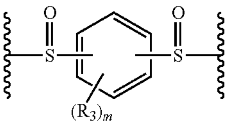,
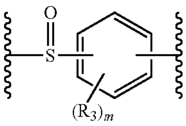,
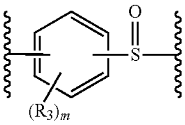,
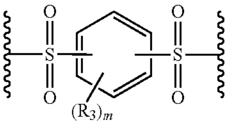,
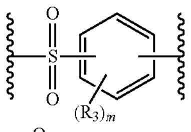,
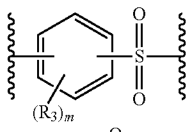,
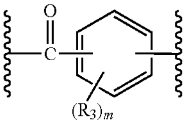,
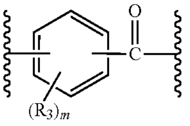, and -continued

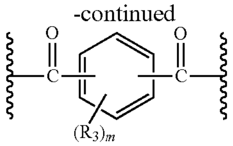;

each n is an integer selected from 0 to 6;

m is an integer selected from 0 to 4; and each $R_1$ and $R_2$ is independently selected from hydrogen, methyl, ethyl, and halogen; and $R_3$ is selected from hydrogen, methyl, ethyl, propyl, amino, nitro, cyano, trifluoromethyl, alkoxy, azido, and halogen.

2. The compound of claim 1 with the following structure:

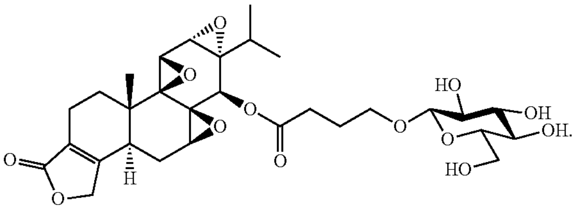

3. A compound of the structure of Formula (II):

Formula (II)

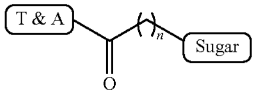

or a pharmaceutically acceptable salt, a stereoisomer, a diastereoisomer or an enantiomer thereof, wherein n is an integer selected from 0 to 10;

T & A moiety is selected from

TA1

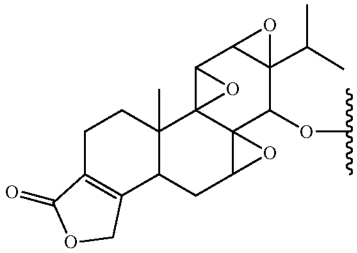,

TA2

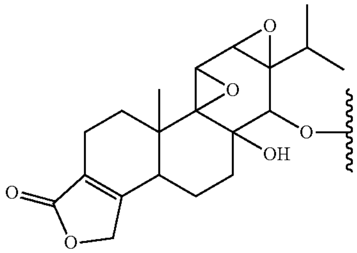,

-continued
TA3
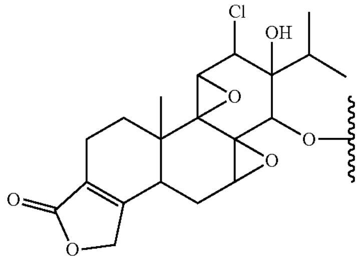
,
TA4
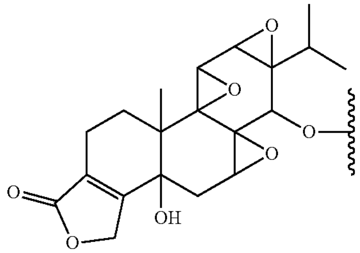
,
TA5
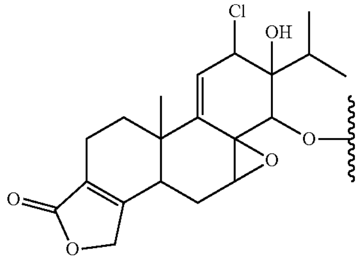
,
TA6
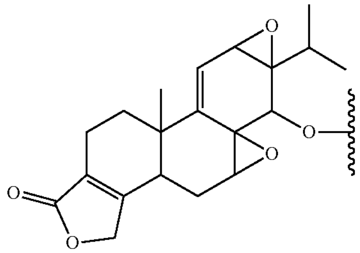
,
TA7
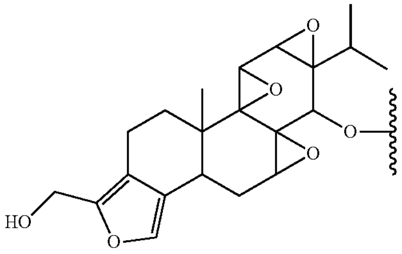
,
TA8
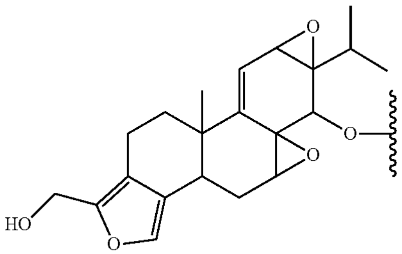
,
-continued
TA9
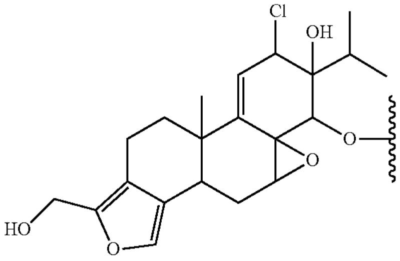
,
TA10
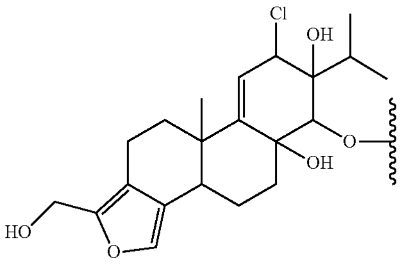
,
TA11
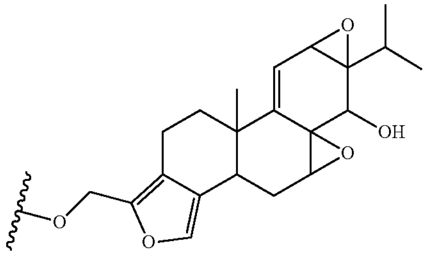
,
TA12
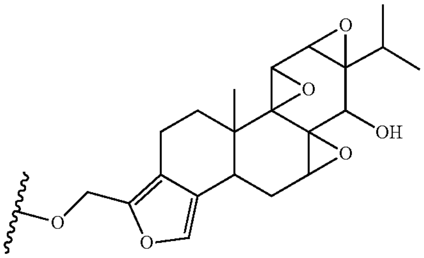
,
TA13
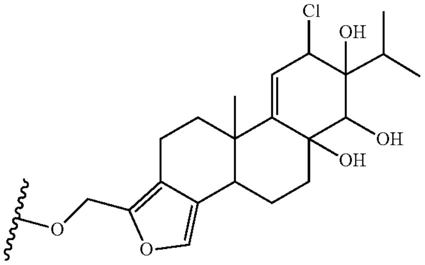
,
TA14
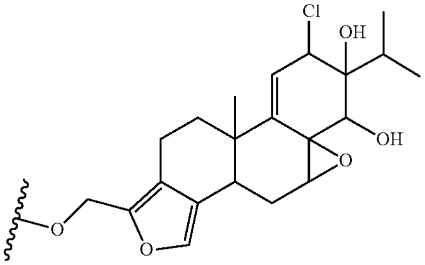
, -continued
TA15
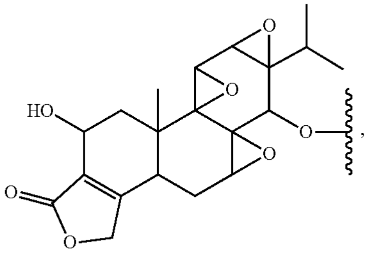
TA16
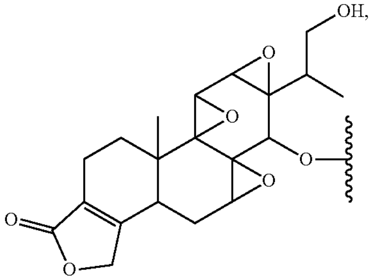
and
TA17
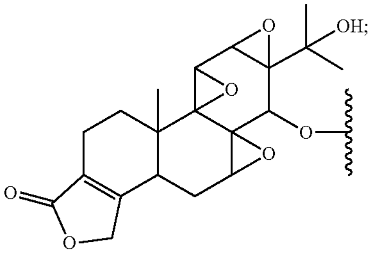
and
Sugar moiety can be selected from
sugar 1
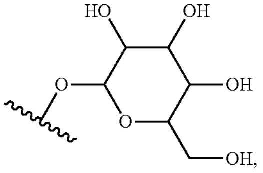
sugar 2
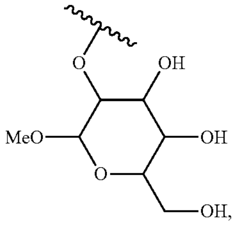
sugar 3
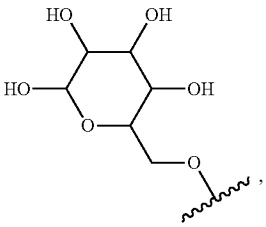
-continued
sugar 4
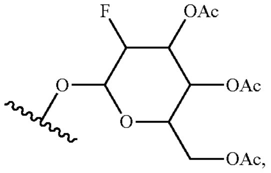
sugar 5
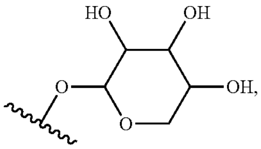
sugar 6
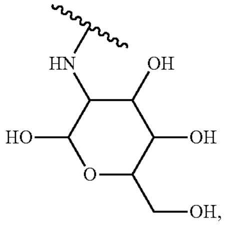
sugar 7
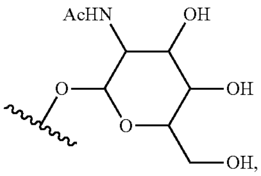
sugar 8
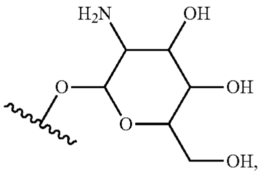
sugar 9
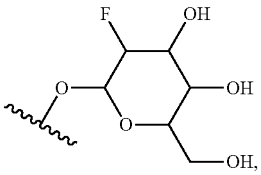
sugar 10
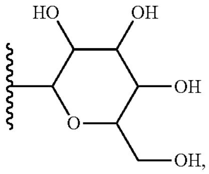
sugar 11
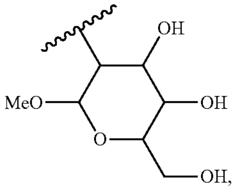

-continued sugar 12

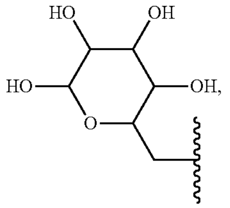

sugar 13

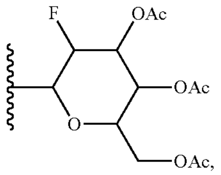

sugar 14

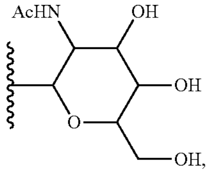

sugar 15

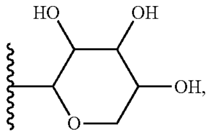

sugar 16

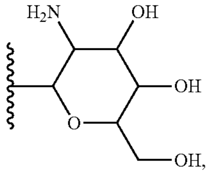

sugar 17

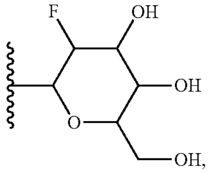

sugar 18

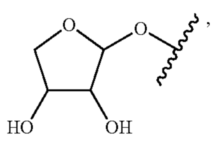

sugar 19

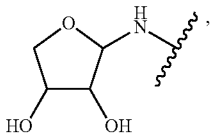

, and sugar 20

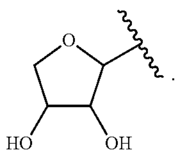

4. The compound of claim 3, wherein n is 3.

5. The compound of claim 3, wherein the T & A moiety is

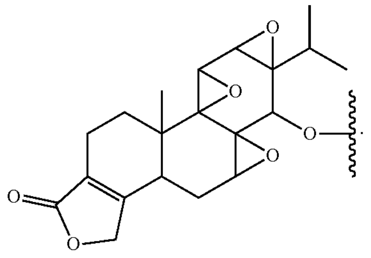

TA1

6. The compound of claim 3, wherein the Sugar moiety is

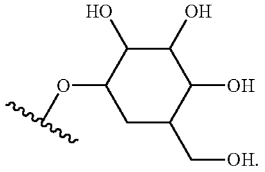

sugar 1

7. A pharmaceutical formulation, comprising the compound according to claim 1, and a pharmaceutically acceptable carrier.

8. A pharmaceutical formulation, comprising the compound according to claim 2, and a pharmaceutically acceptable carrier.

9. A pharmaceutical formulation, comprising the compound according to claim 3, and a pharmaceutically acceptable carrier.

10. A method of treating a disease in a subject, comprising administering to the subject an effective amount of the compound according to claim 1, wherein the disease is cancer.

11. The method of claim 10, wherein the cancer is selected from the group consisting of central nervous system (CNS) cancer, lung cancer, breast cancer, colorectal cancer, prostate cancer, stomach cancer, liver cancer, cervical cancer, esophageal cancer, bladder cancer, Non-Hodgkin lymphoma, leukemia, pancreatic cancer, kidney cancer, endometrial cancer, head and neck cancer, lip cancer, oral cancer, thyroid cancer, brain cancer, ovary cancer, renal cancer, melanoma, gallbladder cancer, laryngeal cancer, multiple myeloma, nasopharyngeal cancer, Hodgkin lymphoma, testis cancer and Kaposi sarcoma.

12. The method of claim 10, comprising further administering a chemotherapeutic agent.

13. The method of claim 12, wherein the compound is administered prior to, simultaneously with or following the administration of the chemotherapeutic agent.

14. The method of claim 10, wherein the compound is administered subcutaneously, intravenously, intramuscularly, intranasally, orally, or topically.

15. The method of claim 10, wherein the compound is formulated in a delayed release preparation, a slow release preparation, an extended release preparation, or a controlled release preparation.

16. The method of claim 10, wherein the compound is provided in a dosage form selected from an injectable dosage form, infusible dosage form, inhalable dosage form, edible dosage form, oral dosage form, topical dosage form, and combinations thereof.

17. A method of synthesizing a compound according to claim 1, or a pharmaceutically acceptable salt, a stereoisomer, a diastereoisomer or an enantiomer thereof, the method comprising:

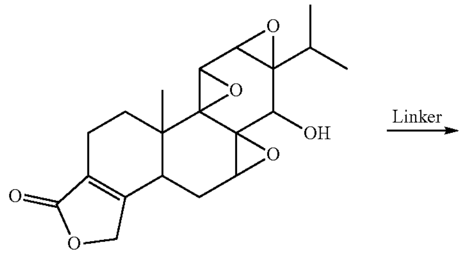

Triptolide

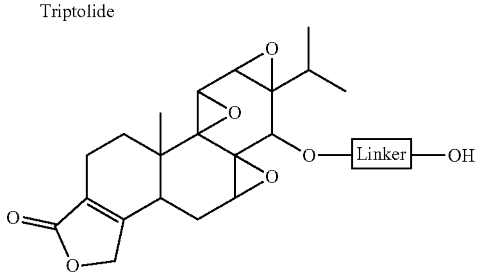

T1

(a) conjugating triptolide with a Linker selected from 4-hydroxybutanoic acid and phthalic acid to form a triptolide Linker derivative T1;

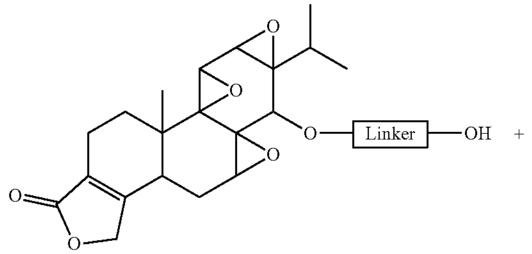

T1

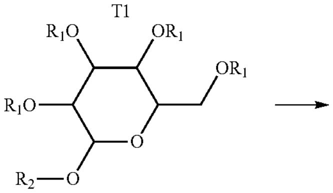

T2

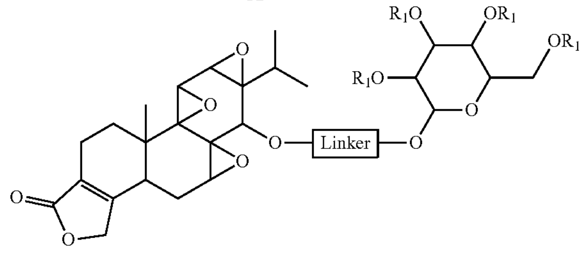

T3

(b) reacting T1 with a sugar intermediate T2 to get intermediate T3, wherein $R_1$ is selected from the group consisting of para-methoxylbenzyl (PMB), 1-chloroacetyl protective group, triethylsilyl, and benzyl; and $R_2$ is hydrogen or CNHCCl3; and

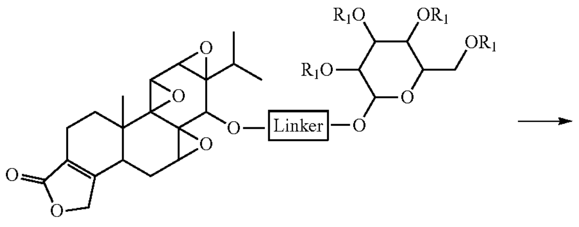

T3

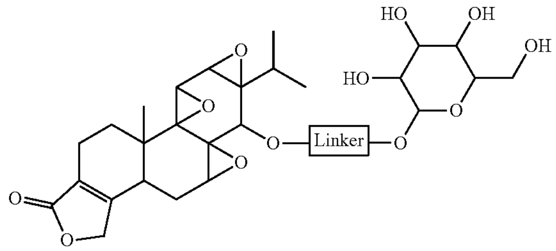

T4

(c) deprotecting the intermediate T3 to obtain glucose-triptolide conjugate T4, or a stereoisomer, a diastereoisomer or an enantiomer thereof.

18. A method of synthesizing a compound according to claim 1, or a pharmaceutically acceptable salt, a stereoisomer, a diastereoisomer or an enantiomer thereof, the method comprising:

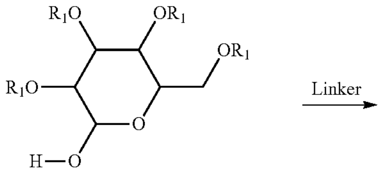

T5

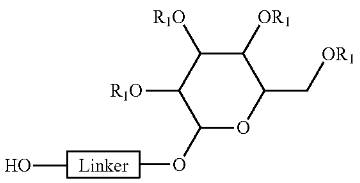

T6

(a) conjugating T5 with a Linker selected from 4-hydroxybutanoic acid and phthalic acid to form Linker derivative T6, wherein X is O, $R_1$ is selected from para-methoxybenzyl (PMB), 1-chloroacetyl protective group, triethylsilyl, and benzyl;

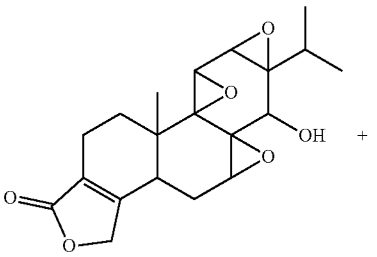

Triptolide

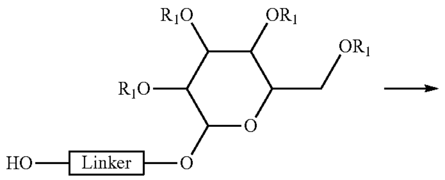

T6

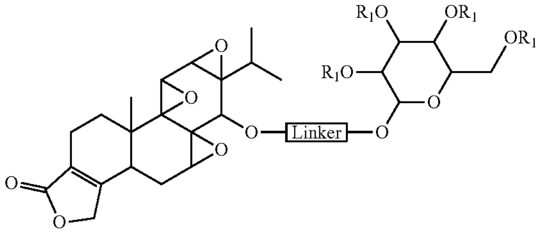

T3

(b) reacting the Linker derivative T6 with triptolide to get an intermediate T3; and

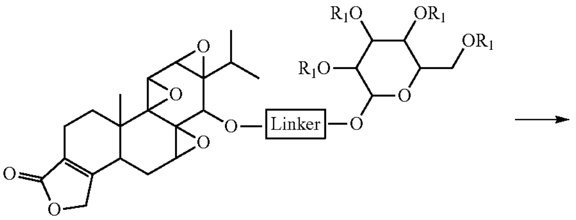

T3

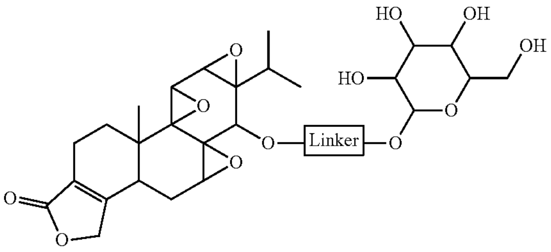

T4

(c) deprotecting the intermediate T3 to obtain glucose-triptolide conjugate T4, or a stereoisomer, a diastereoisomer or an enantiomer thereof.

19. The method according to claim 17, wherein R1 is para-methoxylbenzyl (PMB).

20. The method according to claim 17, wherein R2 is $CNHCCl_3$.

21. The method according to claim 17, wherein the deprotecting reaction at step (c) uses trifluoroacetic acid (TFA).

* * * * *